(12) United States Patent
Shannon et al.

(10) Patent No.: US 8,476,281 B2
(45) Date of Patent: *Jul. 2, 2013

(54) SOLID FORMS OF GYRASE INHIBITOR (R)-1-ETHYL-3-[6-FLUORO-5-[2-(1-HYDROXY-1-METHYL-ETHYL)PYRIMIDIN-5-YL]-7-(TETRAHYDROFURAN-2-YL)-1H-BENZIMIDAZOL-2-YL]UREA

(75) Inventors: Dean Shannon, Milford, MA (US); Brian Luisi, Somerville, MA (US); Mariusz Krawiec, Marlborough, MA (US); Anuj K. Kuldipkumar, Medford, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/349,984

(22) Filed: Jan. 13, 2012

(65) Prior Publication Data
US 2012/0184564 A1    Jul. 19, 2012

Related U.S. Application Data

(60) Provisional application No. 61/433,169, filed on Jan. 14, 2011.

(51) Int. Cl.
*A01N 43/54* (2006.01)
*C07D 239/42* (2006.01)
*C07D 471/04* (2006.01)

(52) U.S. Cl.
USPC .......................................... 514/256; 544/333

(58) Field of Classification Search
USPC ....................................................... 544/333
See application file for complete search history.

(56) References Cited

U.S. PATENT DOCUMENTS

| | | | |
|---|---|---|---|
| 3,856,957 A | 12/1974 | Seng et al. | |
| 4,174,400 A | 11/1979 | Mrozik | |
| 4,512,998 A | 4/1985 | Nafissi-Varchei | |
| 5,529,998 A | 6/1996 | Habich et al. | |
| 5,643,935 A | 7/1997 | Dykstra et al. | |
| 6,632,809 B2 | 10/2003 | Grillot et al. | |
| RE40,245 E | 4/2008 | Grillot et al. | |
| 7,414,046 B2 * | 8/2008 | Grillot et al. ............ | 514/215 |
| 7,495,014 B2 | 2/2009 | Charifson et al. | |
| 7,569,591 B2 | 8/2009 | Charifson et al. | |
| 7,582,641 B2 | 9/2009 | Charifson et al. | |
| 7,618,974 B2 | 11/2009 | Charifson et al. | |
| 7,674,801 B2 | 3/2010 | Basarab et al. | |
| 7,727,992 B2 | 6/2010 | Charifson et al. | |
| 7,977,340 B2 | 7/2011 | Haydon et al. | |
| 8,034,832 B2 | 10/2011 | Charifson et al. | |
| 8,067,606 B2 | 11/2011 | Charifson et al. | |
| 8,188,095 B2 | 5/2012 | Charifson et al. | |
| 8,193,352 B2 | 6/2012 | Charifson et al. | |
| 2004/0043989 A1 | 3/2004 | Grillot et al. | |
| 2004/0235886 A1 | 11/2004 | Charifson et al. | |
| 2005/0038247 A1 | 2/2005 | Charifson et al. | |
| 2005/0256136 A1 | 11/2005 | Charifson et al. | |
| 2006/0025424 A1 | 2/2006 | Charifson et al. | |
| 2006/0122196 A9 | 6/2006 | Charifson et al. | |
| 2008/0132546 A1 | 6/2008 | Basarab et al. | |
| 2009/0176771 A1 | 7/2009 | Charifson et al. | |
| 2009/0197877 A1 | 8/2009 | Haydon et al. | |

(Continued)

FOREIGN PATENT DOCUMENTS

| | | |
|---|---|---|
| EP | 0433648 | 6/1991 |
| EP | 0738726 | 10/1996 |

(Continued)

OTHER PUBLICATIONS

Beers, M. H., and Berkow, R., "The Merck Manual of Diagnosis and Therapy", 7th Edition, Chapter 156—Bacteremia and Septic Shock, Merck Research Laboratories, Whitehouse Station, NJ pp. 1143-1147 (1999).

(Continued)

*Primary Examiner* — James O Wilson
*Assistant Examiner* — Alexander R Pagano
(74) *Attorney, Agent, or Firm* — Brinks Hofer Gilson & Lione; William R. Boudreaux; Bashir M. Ali

(57) ABSTRACT

The present application is directed to solid forms of compounds of formula I:

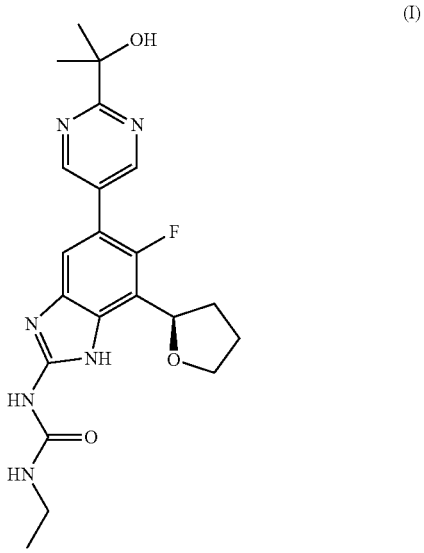

and pharmaceutically acceptable salts thereof, that inhibit bacterial gyrase and/or Topo IV and pharmaceutical compositions comprising said compounds and salts. These compounds and salts are useful in treating bacterial infections.

23 Claims, 10 Drawing Sheets

U.S. PATENT DOCUMENTS

| | | | |
|---|---|---|---|
| 2009/0325935 | A1 | 12/2009 | Charifson et al. |
| 2010/0063069 | A1 | 3/2010 | Charifson et al. |
| 2010/0311766 | A1 | 12/2010 | Haydon et al. |
| 2011/0104207 | A1 | 5/2011 | Charifson et al. |
| 2011/0166088 | A1 | 7/2011 | Sattigeri et al. |
| 2011/0263590 | A1 | 10/2011 | Haydon et al. |
| 2012/0004221 | A1 | 1/2012 | Haydon et al. |
| 2012/0010222 | A1 | 1/2012 | Charifson et al. |
| 2012/0184512 | A1* | 7/2012 | Le Tiran et al. ............... 514/86 |
| 2012/0184564 | A1 | 7/2012 | Shannon et al. |
| 2012/0184741 | A1* | 7/2012 | Shannon et al. ............ 544/333 |
| 2012/0184742 | A1* | 7/2012 | Shannon et al. ............ 544/333 |

FOREIGN PATENT DOCUMENTS

| | | |
|---|---|---|
| EP | 1055668 | 11/2000 |
| WO | WO 99/35155 | 7/1999 |
| WO | WO 00/49015 | 8/2000 |
| WO | WO 00/71522 | 11/2000 |
| WO | WO 02/060879 | 8/2002 |
| WO | WO 03/105846 | 12/2003 |
| WO | WO 2005/012292 | 10/2005 |
| WO | WO 2006/022773 | 3/2006 |
| WO | WO 2007/056330 | 5/2007 |
| WO | WO 2007/148093 | 12/2007 |
| WO | WO 2008/068470 | 6/2008 |
| WO | WO 2009/074810 | 6/2009 |
| WO | WO 2009/074812 | 6/2009 |
| WO | WO 2009/156966 | 12/2009 |
| WO | WO 2011/032050 | 3/2011 |
| WO | WO 2011/047323 | 4/2011 |
| WO | WO 2012/045124 | 4/2012 |

OTHER PUBLICATIONS

Champoux, J.J., Annu. Rev. Biochem., 2001, 70, pp. 369-413.
Charifson et al., J. Med. Chem., 2008, 51, pp. 5243-5263.
Charles W. Stratton, MD. "In Vitro Susceptibility Testing Versus in Vivo-Effectiveness" The Medical Clinics of North America 2006, 90, 1077-1088.
Drlica and Zhao, Microbiology and Molecular Biology Reviews, 1997, 61, pp. 377-392.
Joseph E. Drumm et al., "Facile preparation of fused ring azolylureas," 48 Tetrahedron Lett. 5535-5538 (2007).
Stephen P. East et al., "DNA gyrase (GyrB)/topoisomerase IV (ParE) inhibitors," 19 Bioorg. Med. Chem. Lett. 894-899 (2009).
Eckert et al., "The antifungal activity of . . . " CA 93:39290 (1980).
Gershman in The Medical Reporter, 1997.
Guven et al. "Synthesis and Antimicrobial Activity of Some Novel Furyl and Benzimidazole Substituted Benzyl Ethers" Journal of Heterocyclic Chemistry 2007, 44, 731.
He et al. "Synthesis and biological evaluation of novel benzimidazoles as potential antibacterial agents." Bioorganic & Medicinal Chemistry Letters 2004, 14, 1217-1220.
Hubschwerlen et al., "Pyrimido[1,6-1]benzimidazoles: A New Class of DNA Gyrase Inhibitors" J. Med. Chem, vol. 35, No. 8, pp. 1385-1392, 1992.

International Search Report and Written Opinion of the International Searching Authority, International Patent Application No. PCT/US2012/021270 (Mar. 16, 2012).
International Search Report and Written Opinion of the International Searching Authority, International Patent Application No. PCT/US2012/021281 (May 3, 2012).
International Search Report and Written Opinion of the International Searching Authority, International Patent Application No. PCT/US2012/021280 (Mar. 23, 2012).
International Search Report and Written Opinion of the International Searching Authority, International Patent Application No. PCT/US2012/021275 (Mar. 23, 2012).
Kornberg and Baker, DNA Replication, 2d Ed., Chapter 12, 1992, W. H. Freeman and Co.
Kus, C., "Synthesis and Antimicrobial Activities of 5-fluoro-1, 2, 6-trisubstituted benzimidazole carboxamide and acetamide derivatives," Arch. Pharm. Pharm. Med. Chem. 334(11):361-365 (2001).
Levy, "The Challenge of Antibiotic Resistance", Scientific American, Mar. 1998).
Lewis, "The Rise of Antibiotic-Resistant Infections", FDA Consumer magazine, Sep. 1995.
Maxwell, Mol. Microbiol., 1993, 9, 681.
Maxwell, Trends in Microbiology, 1997, 5, 102.
MayoClinic "Antibiotic associated diarrhea" Mayoclinic.com. (2007).
Nicolaus B.J.R., "Symbiotic Approach to Drug Design," Decision Making in Drug Research, pp. 173-186 (1983).
Pea et al., PubMed Abstract (Clin Pharmacokinet. 44(10):1009-34) 2005.
Singh, S.K., et al., "Studies in antiparastic agents: Part 13—Synthtesis of 4-aryl-2-substitutedamino-thiazoles as potential anthelmintics," Indian J. Chem., 28B (9):786-789 (1989).
Skopenka, V.V., et al., "Organotin Carbamoyldicyanomethanide, nitrosocarbamoylcyanomethanide, and Carbamoylcyanides," retrieved from STN Database accession No. 101:230674, XP002254350 abstract and Dopovidi Akademii Nauk Ukrains'Koi RSR, Seriya B: Geologichni, Khimichni Ta Biologichni Nauki, 7:44-46 (1984).
Snyder et al., PubMed Abstract (J. Med Liban. 48(4):208-14), Jul.-Aug. 2000.
Sun et al., "Synthesis and Evaluation of Terbenzimidazoles as Topoisomerase I Inhibitors" J. Med. Chem., vol. 38, No. 18, pp. 3638-3644, 1995.
Tanitame et al. "Design, synthesis and structure-activity relationship studies of novel indazole analogues as DNA gyrase inhibitors with Gram-positive antibacterial activity" Bioorganic & Medicinal Chemistry Letters 2004, 14, 2857-2862.
Drlica, Molecular Microbiology, 1992, 6, 425.
Wassenaar "Bacteria; more than pathogens" Am. Ins. Biol. Sci. Internet p. 1-7 (2002).
Webster's Dictionary (1984) p. 933.
WHO Report, "Use of Quinolones in Food Animals and Potential Impact on Human Health", 1998.

* cited by examiner

SOLID FORMS OF GYRASE INHIBITOR (R)-1-ETHYL-3-[6-FLUORO-5-[2-(1-HYDROXY-1-METHYL-ETHYL)PYRIMIDIN-5-YL]-7-(TETRAHYDROFURAN-2-YL)-1H-BENZIMI-DAZOL-2-YL]UREA

CROSS REFERENCE TO RELATED APPLICATIONS

This application claims the benefit under 35 U.S.C. §119 of U.S. Provisional Patent Application Ser. No. 61/433,169 filed Jan. 14, 2011, the entire contents of which is incorporated herein by reference.

BACKGROUND OF THE APPLICATION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as Streptococcus pneumoniae (SP), Mycobacterium tuberculosis, and Enterococcus. The appearance of vancomycin resistant enterococcus was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as Staphylococcus aureus, where methicillin resistance is already prevalent (De Clerq, et al., Current Opinion in Anti-infective Investigational Drugs, 1999, 1, 1; Levy, "The Challenge of Antibiotic Resistance", Scientific American, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in The Medical Reporter, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", FDA Consumer magazine, September 1995).

As a result of the need to combat drug-resistant bacteria and the increasing failure of the available drugs, there has been a resurgent interest in discovering new antibiotics. One attractive strategy for developing new antibiotics is to inhibit DNA gyrase and/or topoisomerase IV, bacterial enzymes necessary for DNA replication, and therefore, necessary for bacterial cell growth and division. Gyrase and/or topoisomerase IV activity are also associated with events in DNA transcription, repair and recombination.

Gyrase is one of the topoisomerases, a group of enzymes which catalyze the interconversion of topological isomers of DNA (see generally, Kornberg and Baker, DNA Replication, 2d Ed., Chapter 12, 1992, W. H. Freeman and Co.; Drlica, Molecular Microbiology, 1992, 6, 425; Drlica and Zhao, Microbiology and Molecular Biology Reviews, 1997, 61, pp. 377-392). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase and/or topoisomerase IV would be selective for this enzyme and be relatively inactive against the eukaryotic type II topoisomerases.

Topoisomerase IV primarily resolves linked chromosome dimers at the conclusion of DNA replication.

The widely-used quinolone antibiotics inhibit bacterial DNA gyrase (GyrA) and/or Topoisomerase IV (ParC). Examples of the quinolones include the early compounds such as nalidixic acid and oxolinic acid, as well as the later, more potent fluoroquinolones such as norfloxacin, ciprofloxacin, and trovafloxacin. These compounds bind to GyrA and/or ParC and stabilize the cleaved complex, thus inhibiting overall gyrase function, leading to cell death. The fluoroquinolones inhibit the catalytic subunits of gyrase (GyrA) and/or Topoisomerase IV (Par C) (see Drlica and Zhao, Microbiology and Molecular Biology Reviews, 1997, 61, 377-392). However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

The associated subunits responsible for supplying the energy necessary for catalytic turnover/resetting of the enzymes via ATP hydrolysis are GyrB (gyrase) and ParE (topoisomerase IV), respectively (see, Champoux, J. J., Annu. Rev. Biochem., 2001, 70, pp. 369-413). Compounds that target these same ATP binding sites in the GyrB and ParE subunits would be useful for treating various bacterial infections (see, Charifson et al., J. Med. Chem., 2008, 51, pp. 5243-5263).

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, Trends in Microbiology, 1997, 5, 102).

For coumarin-resistant bacteria, the most prevalent point mutation is at a surface arginine residue that binds to the carbonyl of the coumarin ring (Arg136 in *E. coli* GyrB). While enzymes with this mutation show lower supercoiling and ATPase activity, they are also less sensitive to inhibition by coumarin drugs (Maxwell, Mol. Microbiol., 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, Trends in Microbiology, 1997, 5, 102). It would be desirable to have a new, effective GyrB and ParE inhibitor that overcomes these drawbacks and, preferably does not rely on binding to Arg136 for activity. Such an inhibitor would be an attractive antibiotic candidate, without a history of resistance problems that plague other classes of antibiotics.

As bacterial resistance to antibiotics has become an important public health problem, there is a continuing need to develop newer and more potent antibiotics. More particularly, there is a need for antibiotics that represent a new class of compounds not previously used to treat bacterial infection. Compounds that target the ATP binding sites in both the GyrB (gyrase) and ParE (topoisomerase IV) subunits would be useful for treating various bacterial infections. Such compounds would be particularly useful in treating nosocomial infections in hospitals where the formation and transmission of resistant bacteria are becoming increasingly prevalent.

SUMMARY OF THE APPLICATION

The present application relates to solid forms of (R)-1-ethyl-3-[6-fluoro-5-[2-(1-hydroxy-1-methyl-ethyl)pyrimidin-5-yl]-7-(tetrahydrofuran-2-yl)-1H-benzimidazol-2-yl]urea ("the 6-fluoro benzimidazolyl urea compound"). In one embodiment, the present application provides solid Form I of the 6-fluoro benzimidazolyl urea compound, which is characterized by an X-ray powder diffraction pattern (XPRD) comprising at least three approximate peak positions (degrees 2θ±0.2) when measured using Cu $K_\alpha$ radiation, selected from the group consisting of 9.3, 11.7, 12.1, 12.4, 14.5, 15.9, 16.3, 16.6, 18.5, 19.4, 21.5, 22.3, 22.8, 23.8, 24.5, 25.7, 28.1, 28.4, 30.3, and 33.4, when the XPRD is collected from about 5 to about 38 degrees two theta (2 θ). Solid Form I may also be characterized by an X-ray powder diffraction pattern, as measured using Cu $K_\alpha$ radiation, substantially similar to FIG. 1 and an endothermic peak having an onset temperature at about 318° C. as measured by differential scanning calorimetry in which the temperature is scanned at about 10° C. per minute. The present application also provides a method for preparing crystal Form I of the 6-fluoro benzimidazolyl urea compound by suspending a solid material of the free base in a solvent system comprising an alcohol and an ether and isolating the solid.

Another embodiment of the application provides solid Form II of the hydrochloride salt of the 6-fluoro benzimidazolyl urea compound, characterized by an X-ray powder diffraction pattern (XPRD) comprising at least three approximate peak positions (degrees 2θ±0.2) when measured using Cu $K_\alpha$ radiation, selected from the group consisting of 6.7, 9.2, 16.7, 18.6, 19.5, 20.5, 25.6, and 27.5, when the XPRD is collected from about 5 to about 38 degrees 2 θ. Solid Form II may also be characterized by an X-ray powder diffraction pattern, as measured using Cu $K_\alpha$ radiation, substantially similar to FIG. 4 and by an endothermic peak having an onset temperature at about 252° C. as measured by differential scanning calorimetry in which the temperature is scanned at about 10° C. per minute. Solid Form II of the hydrochloride salt of the 6-fluoro benzimidazolyl urea compound may be prepared by suspending a free base of the 6-fluoro benzimidazolyl urea compound in an acidic solvent mixture comprising one or more ethereal solvents and water.

A further embodiment of the present application is an amorphous Form III of the 6-fluoro benzimidazolyl urea compound (free base), characterized by an X-ray powder diffraction pattern (XPRD) using Cu $K_\alpha$ radiation, characterized by a broad halo with no discernable diffraction peak. A further embodiment of the present application is a method for preparing an amorphous Form III of the 6-fluoro benzimidazolyl urea compound (free base) comprising lyophilizing, spray drying, drum drying, or pulse conversion drying a solution of the 6-fluoro benzimidazolyl urea compound.

Yet another embodiment of the present application is an amorphous Form IV of the mesylate salt of the 6-fluoro benzimidazolyl urea compound characterized by an X-ray powder diffraction pattern (XPRD) using Cu $K_\alpha$ radiation, characterized by a broad halo with no discernable diffraction peak.

DETAILED DESCRIPTION

The present application is directed to novel, substantially pure solid forms of (R)-1-ethyl-3-[6-fluoro-5-[2-(1-hydroxy-1-methyl-ethyl)pyrimidin-5-yl]-7-(tetrahydrofuran-2-yl)-1H-benzimidazol-2-yl]urea ("the 6-fluoro benzimidazolyl urea compound").

The inventors have discovered a free base crystalline form of the compound (Form I), a crystalline form of a pharmaceutically acceptable salt of the 6-fluoro benzimidazolyl urea compound (Form II, corresponding to a hydrochloride salt), an amorphous form of the free base (Form III) as well as an amorphous form of the mesylate salt of the compound (Form IV).

Thus, one aspect of the present application is a novel solid Form I of the 6-fluoro benzimidazolyl urea compound (free base). In one aspect, the present application provides a process for preparing solid Form I of the 6-fluoro benzimidazolyl urea compound.

A substantially pure solid Form I of the 6-fluoro benzimidazolyl urea compound may be prepared from amorphous or crystalline compound by contacting the compound with a solvent system comprising an alcohol and an ether and isolating the solid. The 6-fluoro benzimidazolyl urea compound may be contacted with the solvent either by saturating a solution of the 6-fluoro benzimidazolyl urea compound in the solvent at ambient temperature and allowing the mixture to stand for an extended period of time (for example, overnight). Alternatively, the 6-fluoro benzimidazolyl urea compound may be dissolved in the solvent at elevated temperature, for example, at reflux, followed by cooling the solution to room temperature or below and isolating solid Form I.

In one embodiment of the process, a substantially pure solid Form I of the 6-fluoro benzimidazolyl urea compound may be prepared from amorphous or crystalline form of the compound by preparing a saturated solution of the compound in a suitable solvent at room temperature and isolating Form I which results. In practice this can be accomplished by dissolving a sufficient amount of the 6-fluoro benzimidazolyl urea compound in the solvent at elevated temperature (up to reflux) such that when the solution is allowed to cool to room temperature a saturated solution is obtained, from which Form I precipitates and can be isolated. In other embodiments, the 6-fluoro benzimidazolyl urea compound may be isolated from a reaction mixture by modifying the solubility of the compound in the solvent. For example, removing some or all of the solvent or lowering the mixture temperature may reduce the solubility of the 6-fluoro benzimidazolyl urea compound and solid Form I may precipitate. Alternatively, adding a second solvent to the mixture may precipitate solid Form I of the compound.

In one embodiment, the solvent for the preparation of Form I is a mixture of ethanol and ethyl ether. Isolation of the resulting solid provides Form I.

Figure 1:
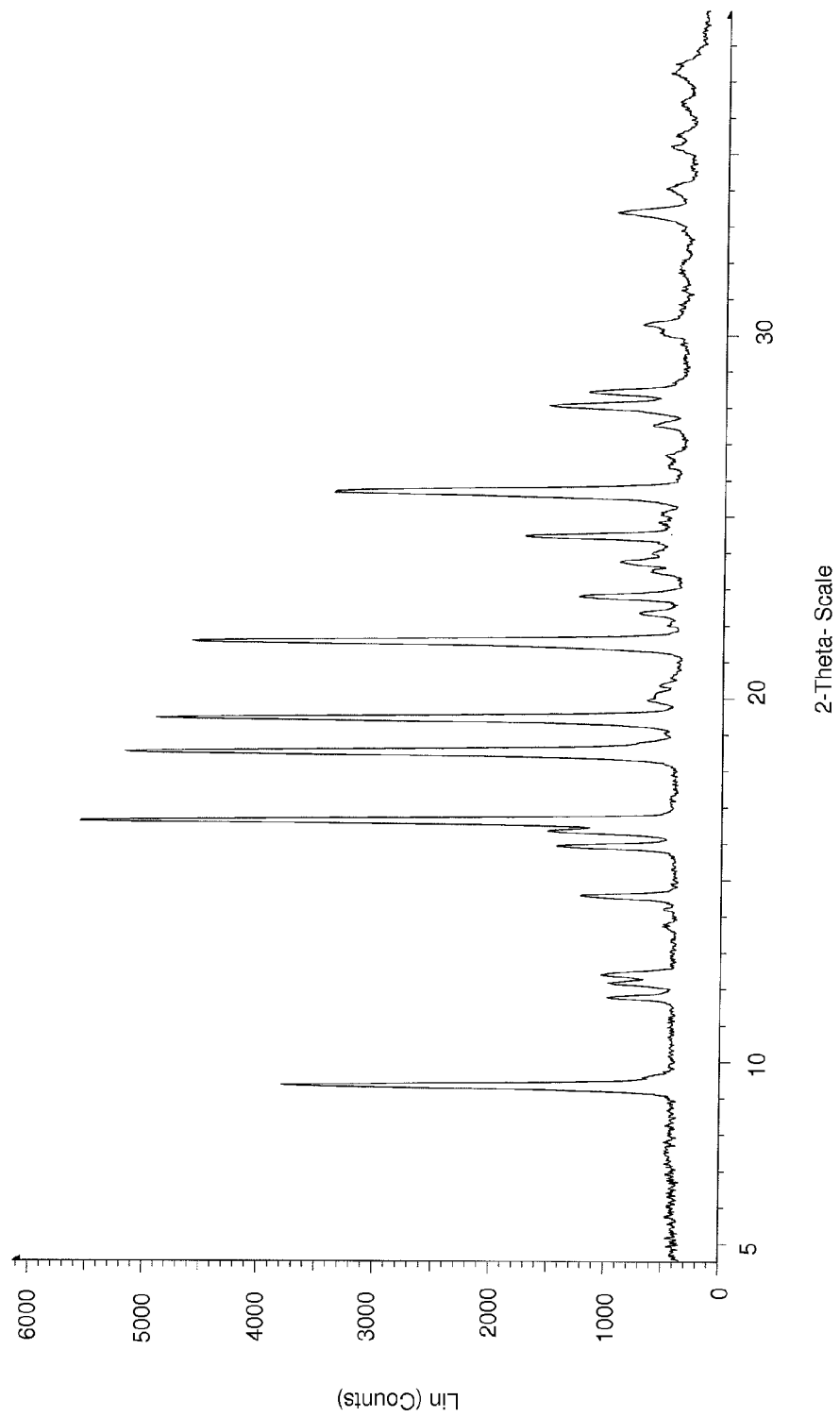
FIG. 1 shows an X-ray powder diffraction pattern of solid Form I of the 6-fluoro benzimidazolyl urea compound (free base) collected from about 5 to about 38 degrees 2 θ.

Solid Form I of the 6-fluoro benzimidazolyl urea compound may be identified by the following characteristics: a broad endotherm at about 250° C., a melt endotherm with an extrapolated onset of about 318° C. as determined by differential scanning calorimetry using 10° C. per minute scan rate; and an X-ray powder diffraction pattern essentially as shown in Table 1 and FIG. 1 wherein the XRPD patterns were measured using a powder diffractometer equipped with a Cu X-ray tube source. The sample was illuminated with Cu $K\alpha_1$ radiation and XRPD data were collected from about 5 to about 40° 2θ. A person skilled in the art would recognize that relative intensities of the XPRD peaks may significantly vary depending on the orientation of the sample under test and on the type and setting of the instrument used, so that the intensities in the XPRD traces included herein are to such extent illustrative and are not intended to be used for absolute comparisons.

FIG. 1 is an X-ray powder diffraction pattern of solid Form I of 6-fluoro benzimidazolyl urea compound (free base) collected from about 5 to about 40 degrees 2 θ. The peaks corresponding to the X-ray powder diffraction pattern having a relative intensity greater than or equal to 5% are listed in Table 1.

Figure 2:
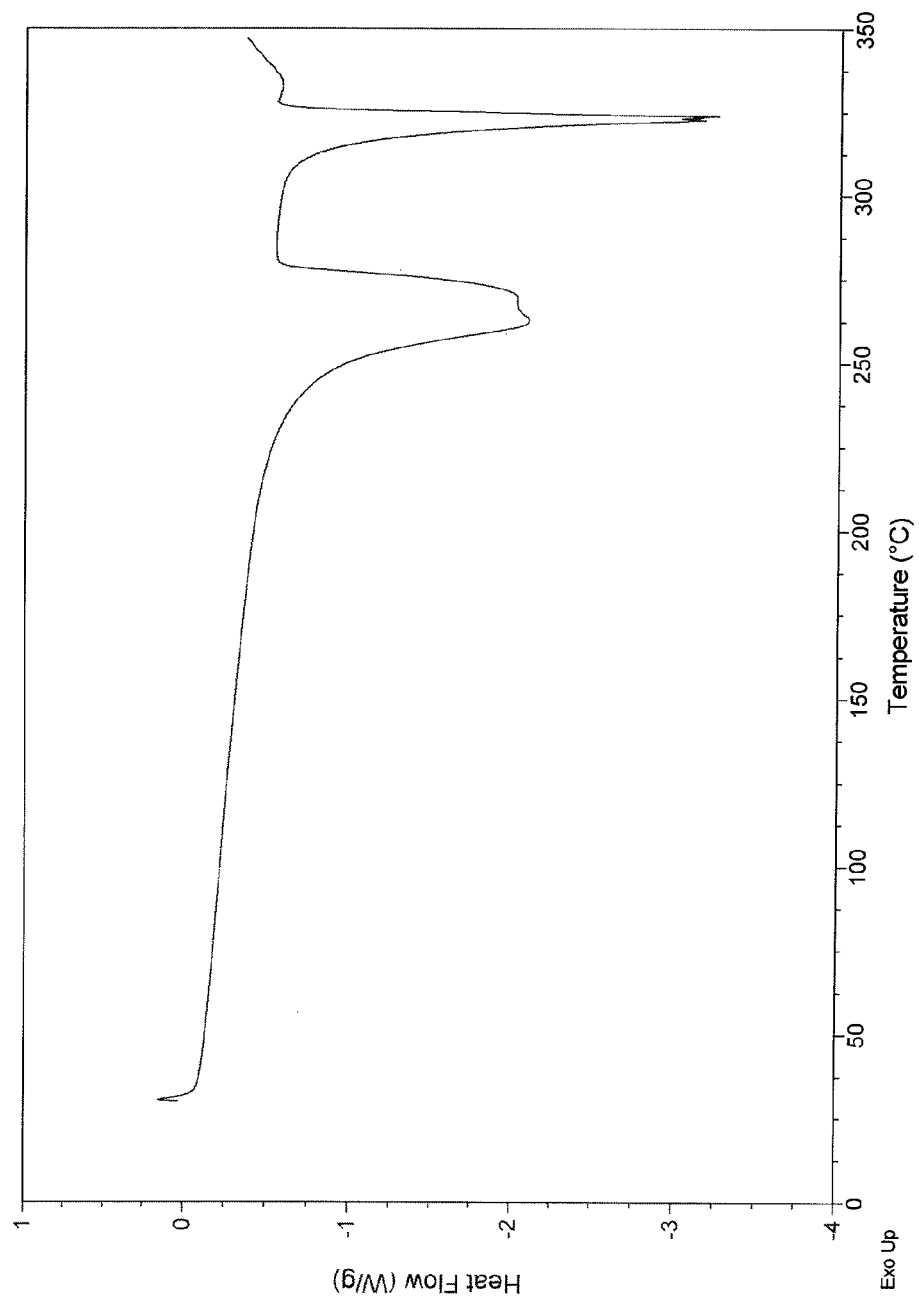
FIG. 2 shows a DSC (Differential Scanning calorimetry) thermogram of solid Form I of the 6-fluoro benzimidazolyl urea compound (free base).

FIG. 2 shows a DSC thermogram of solid Form I of the 6-fluoro benzimidazolyl urea compound exhibiting a broad endotherm with an onset transition at about 250° C. and an endotherm with an onset transition at about 318° C. A person skilled in the art would recognize that the peak and onset temperatures of the endotherms may vary depending on the experimental conditions. Data in FIG. 2 were collected equilibrating a 2.5 mg sample of the solid at about 35° C. for about 10 minutes. During the data collection period, the temperature was increased at a rate of about 10° C. per minute.

Figure 3:
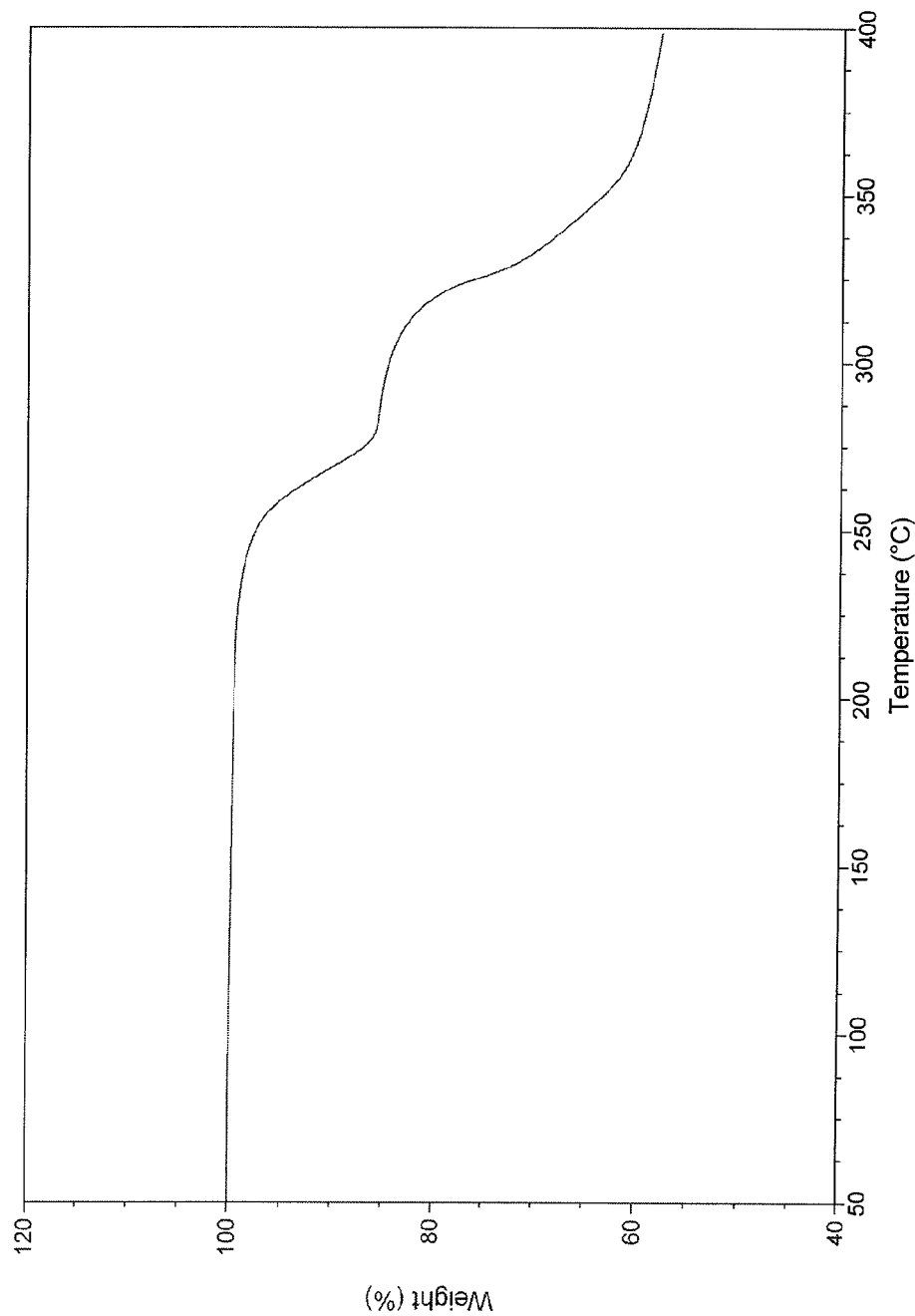
FIG. 3 shows a TGA (thermal gravimetric analysis) thermogram of solid Form I of the 6-fluoro benzimidazolyl urea compound (free base).

FIG. 3 is a TGA (thermal gravimetric analysis) thermogram of solid Form I of the 6-fluoro benzimidazolyl urea compound exhibiting an initial weight loss of about 15% percent in the 50 to 300° C. temperature range with additional weight loss of about 25% between 300 and 400° C.

In one embodiment, the present invention provides a solid Form I of the compound of formula (I):

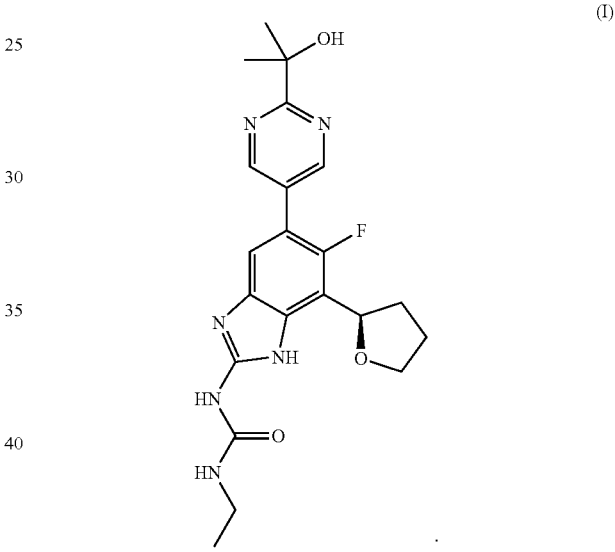

(I)

In another embodiment, the solid Form I is characterized by an X-ray powder diffraction pattern (XPRD) comprising at least three approximate peak positions (degrees 2 θ±0.2) when measured using Cu $K_\alpha$ radiation, selected from the group consisting of 9.3, 11.7, 12.1, 12.4, 14.5, 15.9, 16.3, 16.6, 18.5, 19.4, 21.5, 22.3, 22.8, 23.8, 24.5, 25.7, 28.1, 28.4, 30.3, and 33.4, when the XPRD is collected from about 5 to about 38 degrees 2 θ.

In another embodiment, the solid Form I is characterized by an X-ray powder diffraction pattern (XPRD) comprising at least three approximate peak positions (degrees 2 θ±0.2) when measured using Cu $K_\alpha$ radiation, selected from the group consisting of 9.3, 16.6, 18.5, 19.4, 21.5, and 25.7, when the XPRD is collected from about 5 to about 38 degrees 2 θ.

In another embodiment, the solid Form I is characterized by an X-ray powder diffraction pattern, as measured using Cu $K_\alpha$, radiation, substantially similar to FIG. 1.

In another embodiment, the solid Form I is further characterized by an endothermic peak having an onset temperature at about 318° C. as measured by differential scanning calorimetry in which the temperature is scanned at about 10° C. per minute.

In another embodiment, the present invention provides a method for preparing crystal Form I of the compound of formula (I) comprising suspending a solid material of the free base in solvent system comprising an alcohol and an ether and isolating the solid.

In another embodiment, the solid Form I is stable for at least one month at 40° C. with relative humidity of up to 75%.

TABLE 1

XRPD pattern peaks for solid Form I of the 6-fluoro benzimidazolyl urea compound

| Peak No. | Position [°2θ] | Relative Intensity [%] |
|---|---|---|
| 1 | 9.29 | 66 |
| 2 | 11.74 | 14 |
| 3 | 12.13 | 14 |
| 4 | 12.37 | 15 |
| 5 | 13.71 | 5 |
| 6 | 14.18 | 6 |
| 7 | 14.54 | 19 |
| 8 | 15.90 | 23 |
| 9 | 16.32 | 24 |
| 10 | 16.59 | 100 |
| 11 | 18.49 | 92 |
| 12 | 19.43 | 87 |
| 13 | 19.94 | 9 |
| 14 | 20.36 | 6 |
| 15 | 21.53 | 81 |
| 16 | 22.34 | 10 |
| 17 | 22.80 | 19 |
| 18 | 23.50 | 8 |
| 19 | 23.75 | 13 |
| 20 | 24.45 | 28 |
| 21 | 25.09 | 6 |
| 22 | 25.67 | 58 |
| 23 | 26.39 | 5 |
| 24 | 26.69 | 6 |
| 25 | 27.52 | 8 |
| 26 | 28.05 | 25 |
| 27 | 28.43 | 18 |
| 28 | 30.04 | 6 |
| 29 | 30.31 | 10 |
| 31 | 33.40 | 14 |
| 32 | 34.07 | 6 |
| 33 | 35.22 | 5 |
| 34 | 37.27 | 5 |

In another aspect, the present application provides crystal Form II of the hydrochloric acid addition salt of the 6-fluoro benzimidazolyl urea compound. In one embodiment, the present application provides a process for preparing solid Form II of the 6-fluoro benzimidazolyl urea compound. The pharmaceutically acceptable hydrochloric acid addition salt of the 6-fluoro benzimidazolyl urea compound may be prepared by any method known to those skilled in the art.

In some embodiments, the hydrochloric acid addition salt of the 6-fluoro benzimidazolyl urea compound may precipitate out upon formation from addition of an acid to a solution of the compound. In other embodiments, the acid addition salt may be isolated from the reaction mixture by modifying the solubility of the salt in the solvent. For example, removing some or all of the solvent or lowering the mixture temperature may reduce the solubility of the hydrochloride salt of the 6-fluoro benzimidazolyl urea compound and the salt precipitate. Alternatively, adding a second solvent to the mixture may precipitate the salt.

In further embodiments, gaseous hydrochloric acid may be bubbled through a solution of the 6-fluoro benzimidazolyl urea compound until a mono acid addition salt of the compound is prepared. In certain embodiments, stoichiometric amounts of hydrochloric acid and the 6-fluoro benzimidazolyl urea compound may be mixed together to form a mono acid addition salt of the compound. For example, a solution of the 6-fluoro benzimidazolyl urea compound in a polar solvent may be mixed with a stoichiometric amount of an aqueous solution of hydrochloric acid. Examples of polar solvents that may be suitable for preparing the solid Form II of hydrochloride salt of 6-fluoro benzimidazolyl urea compound include ethers such as diethyl ether and tetrahydrofuran (THF).

In a particular embodiment, stoichiometric amounts of the 6-fluoro benzimidazolyl urea compound in THF and aqueous hydrochloric acid were mixed slowly and the mixture was stirred at room temperature overnight. A solid white hydrochloride salt of the 6-fluoro benzimidazolyl urea compound precipitated out. The solid was isolated, washed with water and dried under vacuum.

Figure 4:
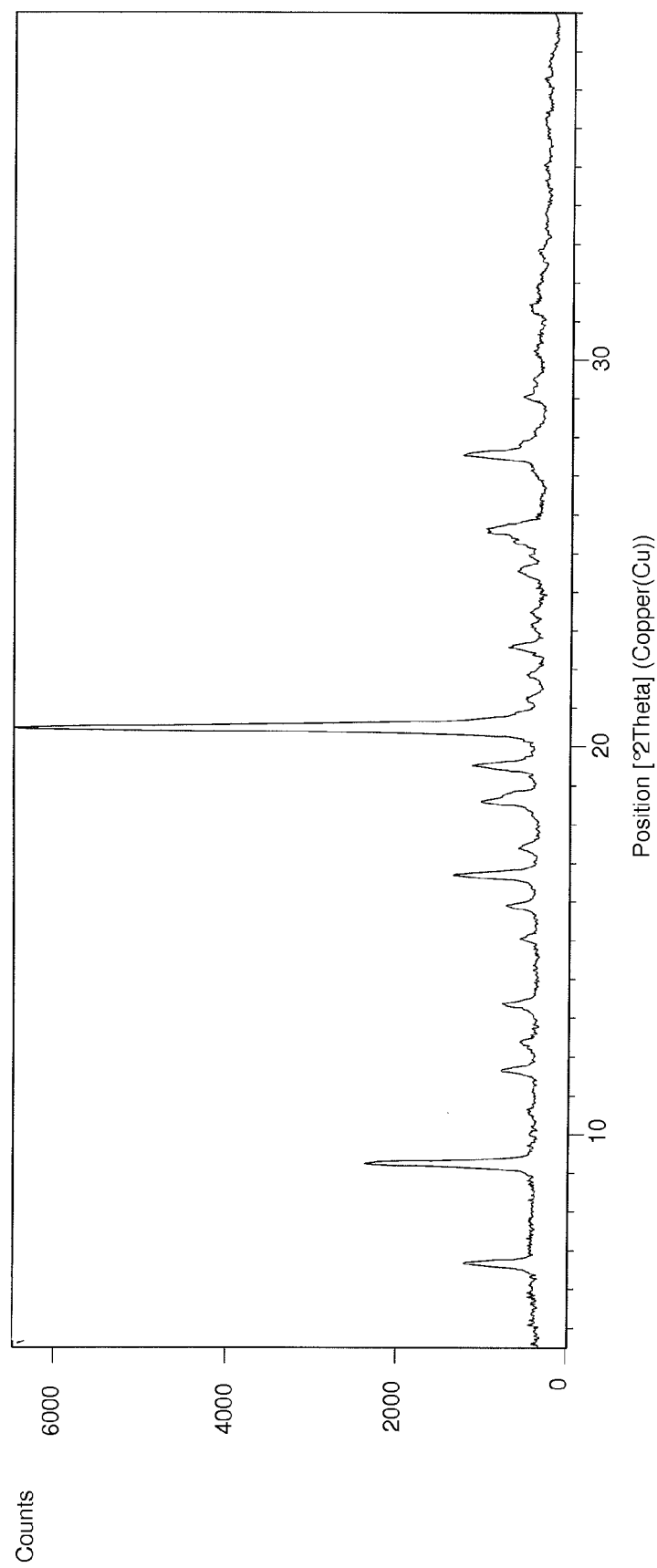
FIG. 4 shows an X-ray powder diffraction pattern of solid Form II of the hydrochloride salt of the 6-fluoro benzimidazolyl urea compound.

Solid Form II of the 6-fluoro benzimidazolyl urea compound may be identified by the following characteristics: a broad endotherm with a peak temperature of about 210° C., a melt endotherm with an extrapolated onset of about 252° C. as determined by differential scanning calorimetry using 10° C. per minute scan rate; and an X-ray powder diffraction pattern essentially as shown in Table 2 and FIG. 4 wherein the XRPD patterns were measured using a powder diffractometer equipped with a Cu X-ray tube source. The sample was illuminated with Cu Kα$_1$ radiation and XRPD data were collected from about 5 to about 40° 2θ. A person skilled in the art would recognize that relative intensities of the XPRD peaks may significantly vary depending on sample orientation.

FIG. 4 is an X-ray powder diffraction pattern of solid Form II of the hydrochloride salt of the 6-fluoro benzimidazolyl urea compound collected from about 5 to about 38 degrees 2θ. The peaks corresponding to X-ray powder diffraction pattern having a relative intensity greater than or equal to 5% are listed in Table 2.

Figure 5:
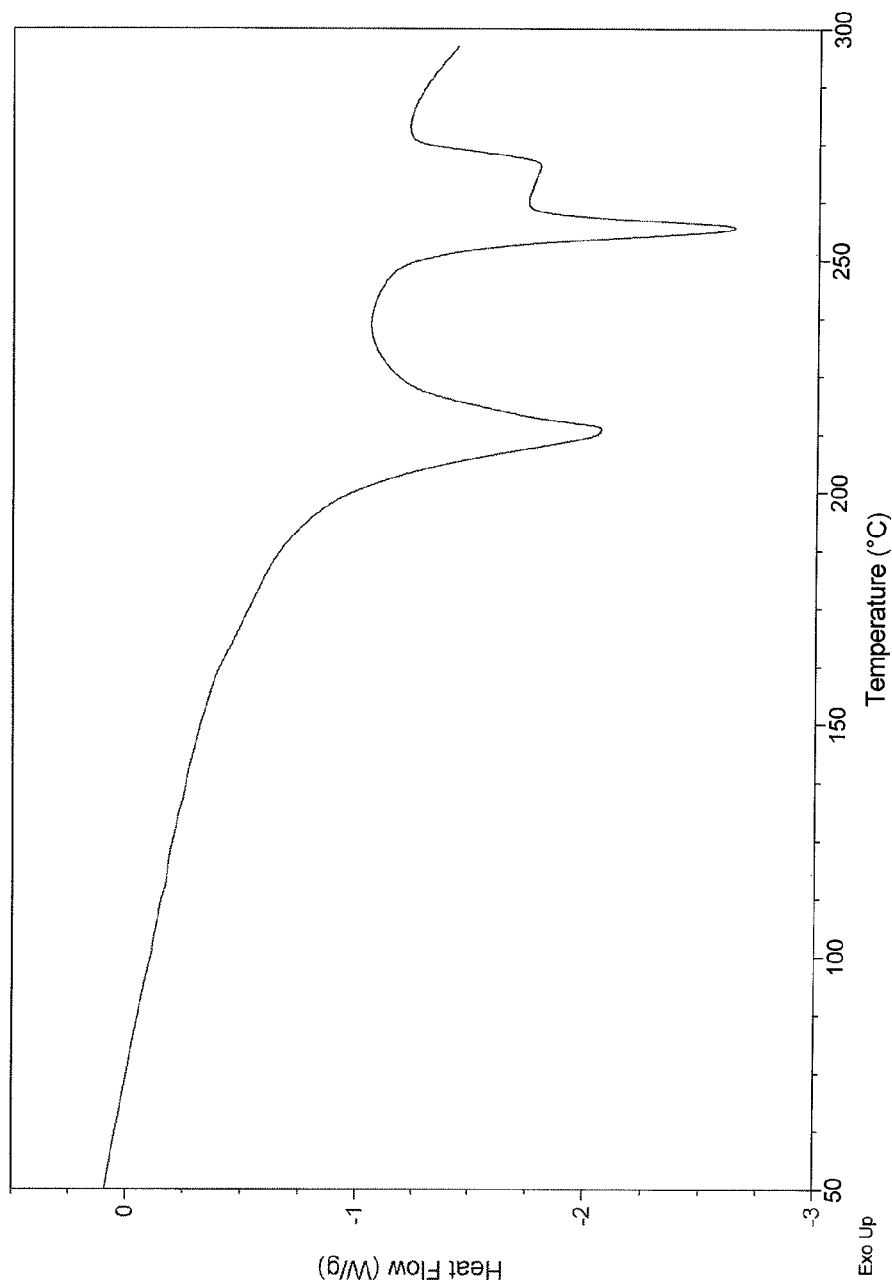
FIG. 5 shows a DSC thermogram of solid Form II of the hydrochloride salt of the 6-fluoro benzimidazolyl urea compound.

FIG. 5 shows a DSC thermogram of solid Form II of the hydrochloride salt of the 6-fluoro benzimidazolyl urea compound exhibiting an endotherm at about 210° C. and an endotherm at about 252° C. A person skilled in the art would recognize that the peak and onset temperatures of the endotherms may vary depending on the experimental conditions. Data in FIG. 5 were collected equilibrating a 1 mg sample of the solid at about 35° C. for about 10 minutes. During the data collection period, the temperature was increased at a rate of about 10° C. per minute.

Figure 6:
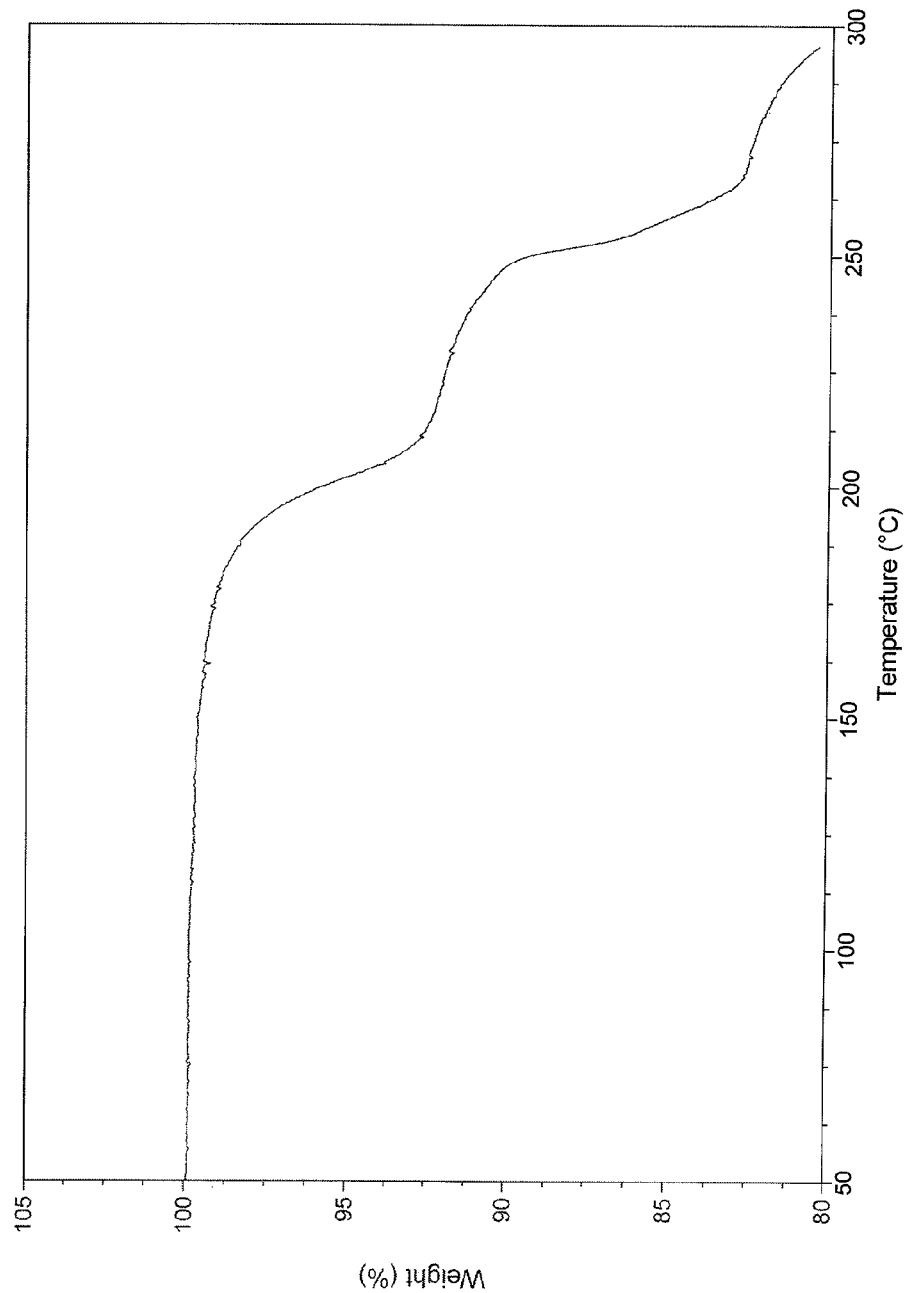
FIG. 6 shows a TGA thermogram of solid Form II of the 6-fluoro benzimidazolyl urea compound.

FIG. 6 is a TGA thermogram of solid Form II of the 6-fluoro benzimidazolyl urea compound exhibiting an initial weight loss of about 8% percent between 100 and 220° C. followed by a second weight loss of about an additional 8% at between about 240 and 270° C. followed by a third weight loss of about 3% between 270 and 300° C. A person skilled in the art would recognize that the onset temperatures of the weight loss may vary depending on the experimental conditions. While applicants do not wish to be held to a particular explanation of the endotherm in the DSC and weight loss in the TGA, it appears that the transition with large peak in the DSC is due to a melting transition coupled with degradation of the material as suggested by the weight loss in the TGA.

In one embodiment, the present invention provides a hydrochloric acid salt of the compound of formula (I):

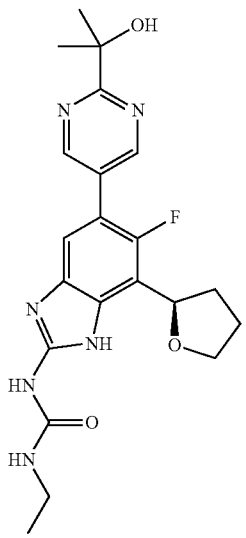

(I)

In another embodiment, the hydrochloric acid salt is Form II solid form.

In another embodiment, the hydrochloric acid salt of Form II solid form is characterized by an X-ray powder diffraction pattern (XPRD) comprising at least three approximate peak positions (degrees 2 θ±0.2) when measured using Cu $K_c$, radiation, selected from the group consisting of 6.7, 9.2, 16.7, 18.6, 19.5, 20.5, 25.6, and 27.5, when the XPRD is collected from about 5 to about 38 degrees 2 θ.

In another embodiment, the hydrochloric acid salt of Form II solid form is characterized by an X-ray powder diffraction pattern, as measured using Cu $K_\alpha$ radiation, substantially similar to FIG. 4.

In another embodiment, the hydrochloric acid salt of Form II solid form is further characterized by an endothermic peak having an onset temperature at about 252° C. as measured by differential scanning calorimetry in which the temperature is scanned at about 10° C. per minute.

In yet another embodiment, the present invention provides a method for preparing solid Form II of the hydrochloride salt of the compound of formula (I) comprising suspending a free base of the 6-fluoro benzimidazolyl urea compound in an acidic solvent mixture comprising one or more ethereal solvents and water.

In another embodiment, the hydrochloric acid salt of Form II solid form is stable for at least one month at 40° C. with relative humidity of up to 75%.

TABLE 2

XRPD pattern peaks for solid Form II of the 6-fluoro benzimidazolyl urea compound

| Peak No. | Position [°2θ] | Relative Intensity [%] |
| --- | --- | --- |
| 1 | 6.67 | 13 |
| 2 | 9.25 | 33 |

TABLE 2-continued

XRPD pattern peaks for solid Form II of the 6-fluoro benzimidazolyl urea compound

| Peak No. | Position [°2θ] | Relative Intensity [%] |
| --- | --- | --- |
| 3 | 11.64 | 7 |
| 4 | 13.36 | 7 |
| 5 | 15.90 | 7 |
| 6 | 16.69 | 17 |
| 7 | 18.59 | 12 |
| 8 | 18.81 | 7 |
| 9 | 19.51 | 14 |
| 10 | 20.48 | 100 |
| 11 | 22.59 | 7 |
| 12 | 24.57 | 5 |
| 13 | 25.61 | 11 |
| 14 | 27.54 | 16 |

Figure 7:
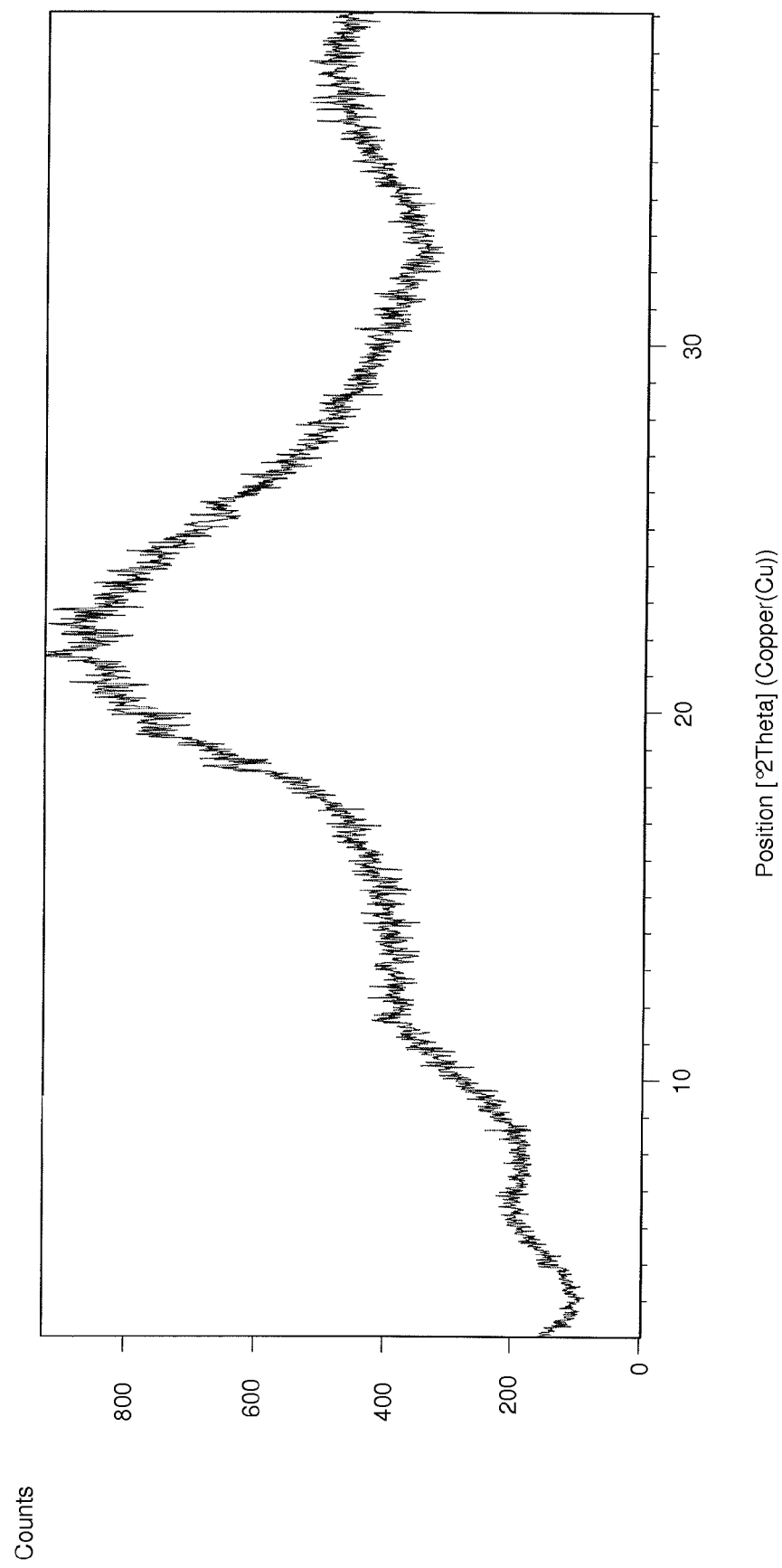
FIG. 7 is an X-ray powder diffraction pattern of an amorphous Form III of the 6-fluoro benzimidazolyl urea compound (free base).

Another aspect of the present application is providing a composition comprising an amorphous 6-fluoro benzimidazolyl urea compound (free base). The term "amorphous" as applied herein to 6-fluoro benzimidazolyl urea compound or its salts refers to a solid state form wherein the 6-fluoro benzimidazolyl urea molecules are generally present in a disordered arrangement and do not form a distinguishable crystal lattice or unit cell. When subjected to X-ray powder diffraction, a completely amorphous compound does not produce a diffraction pattern characteristic of a crystalline form. The X-ray powder diffraction of a partially amorphous material may still lack features characteristic of a crystal form because the diffraction peaks from the crystalline portion of the sample may be too weak to be observable over the noise. FIG. 7 is an X-ray powder diffraction pattern of an amorphous form III of the 6-fluoro benzimidazolyl urea compound (free base).

Figure 8:
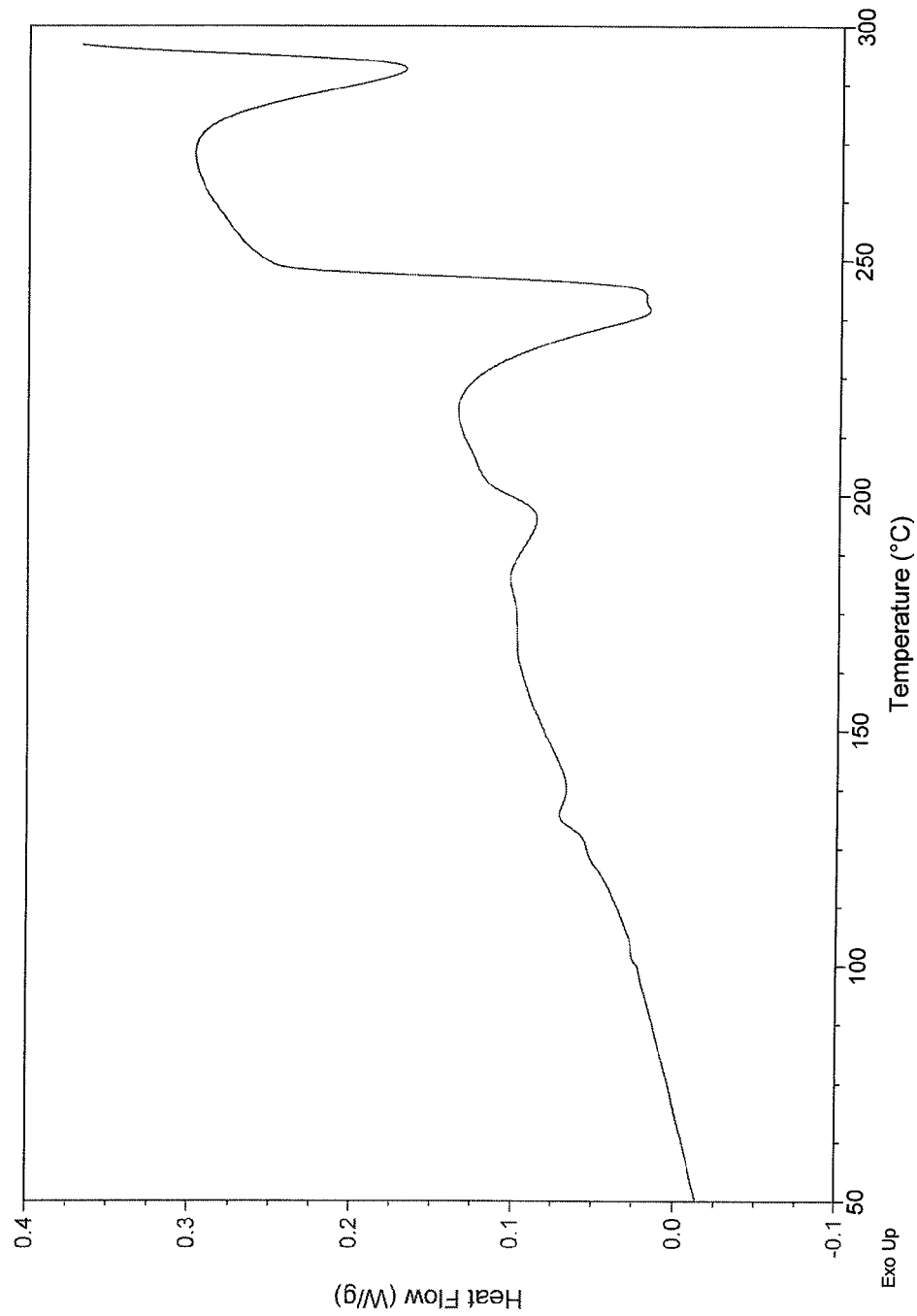
FIG. 8 shows a DSC thermogram of amorphous Form III of 6-fluoro benzimidazolyl urea (free base) exhibiting a small exotherm followed by three larger endotherms.

FIG. 8 shows a DSC thermogram of amorphous Form III of 6-fluoro benzimidazolyl urea (free base) exhibiting a small exotherm followed by three larger endotherms. The small exotherm has an onset temperature of 127° C. whereas the three endotherms have onset temperatures of 183° C., 226° C., and 279° C. A person skilled in the art would recognize that the peak and onset temperatures of the exotherm and the endotherms may vary depending on the experimental conditions. Data in FIG. 8 were collected equilibrating a 2.9 mg sample of the amorphous 6-fluoro benzimidazolyl urea compound at about 35° C. for about 10 minutes. During the data collection period, the temperature was increased at a rate of about 10° C. per minute.

In another embodiment, the present invention provides an amorphous Form III of the fluoro benzimidazolyl urea compound of formula I:

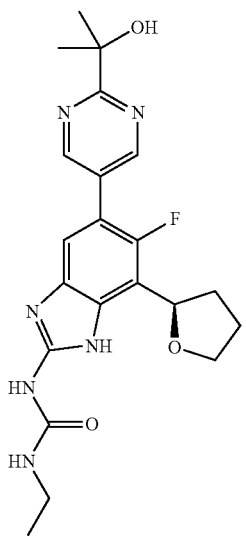

(I)

In another embodiment, the amorphous Form III of the fluoro benzimidazolyl urea compound is characterized by an X-ray powder diffraction pattern (XPRD) using Cu $K_\alpha$ radiation, characterized by a broad halo with no discernable diffraction peak.

In yet another embodiment, the present invention provides a method for preparing amorphous Form III of the 6-fluoro benzimidazolyl urea compound comprising lyophilizing, spray drying, drum drying, or pulse conversion drying a solution of the 6-fluoro benzimidazolyl urea compound.

In another aspect, the present application provides an amorphous solid phase Form IV of the mesylate salt of the 6-fluoro benzimidazolyl urea compound. In one embodiment, the present application provides a process for preparing solid Form IV of the mesylate salt of the 6-fluoro benzimidazolyl urea compound. A pharmaceutically acceptable methanesulphonic acid salt of the 6-fluoro benzimidazolyl urea compound may be prepared by any method known to those skilled in the art. For example, a solution of methanesulphonic acid may be added to a solution of the 6-fluoro benzimidazolyl urea compound until a mono acid addition salt of the compound is prepared. In one embodiment, the mesylate salt of the 6-fluoro benzimidazolyl urea compound may precipitate out upon addition of the acid to a solution of the 6-fluoro benzimidazolyl urea compound. In other embodiments, the acid addition salt may be isolated from the reaction mixture by modifying the solubility of the salt in the solvent. For example, removing some or all of the solvent or lowering the mixture temperature may reduce the solubility of the mesylate salt of the 6-fluoro benzimidazolyl urea compound and the salt precipitate. Thus, in some embodiments, the amorphous material is collected after being precipitated from a solvent or from a solution after concentrating the solution by evaporating some of the solvent, for example, using a rotator evaporator. Alternatively, adding a second solvent to the mixture may precipitate the salt.

Figure 9:
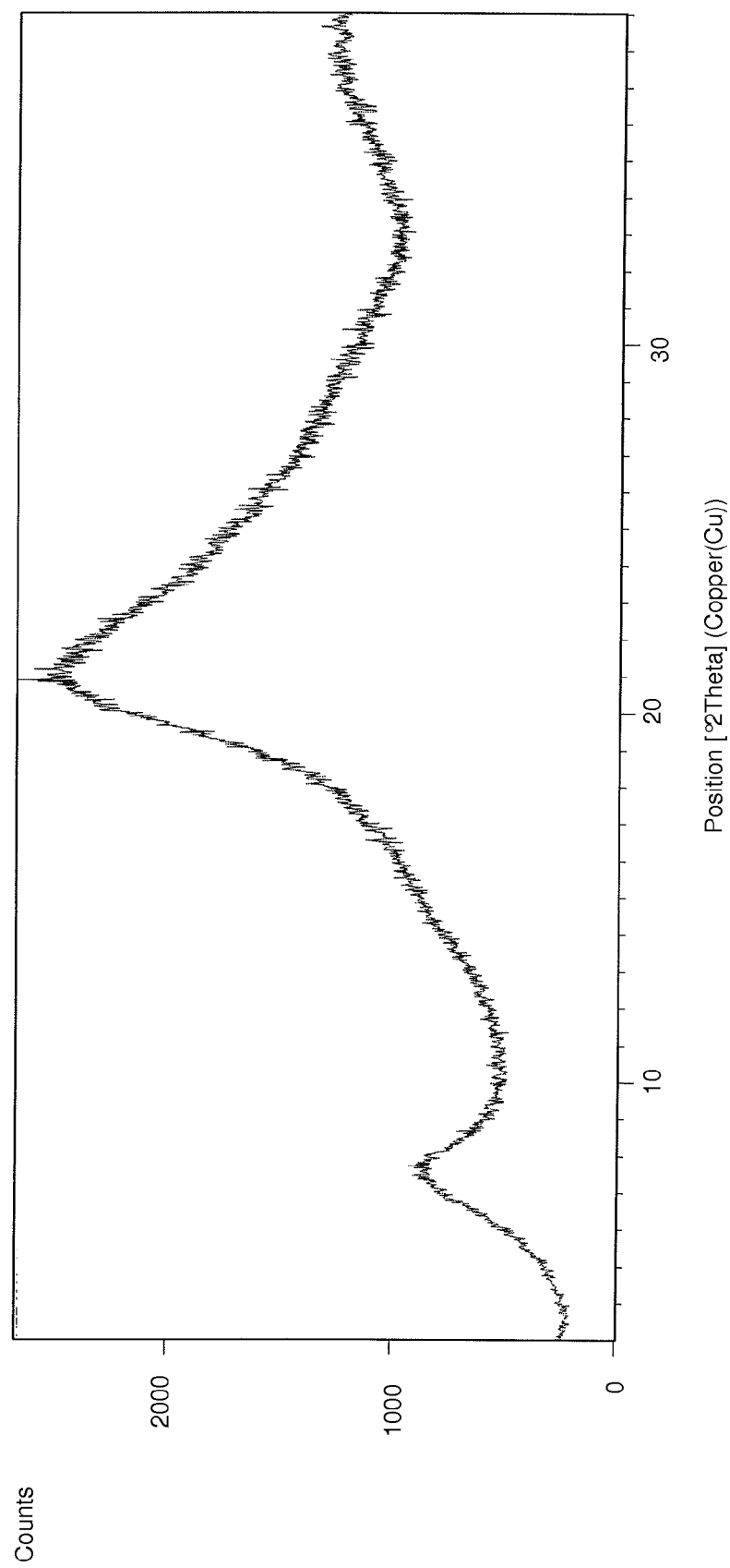
FIG. 9 is an X-ray powder diffraction pattern of an amorphous Form IV of the mesylate salt of the 6-fluoro benzimidazolyl urea compound.
Figure 10:
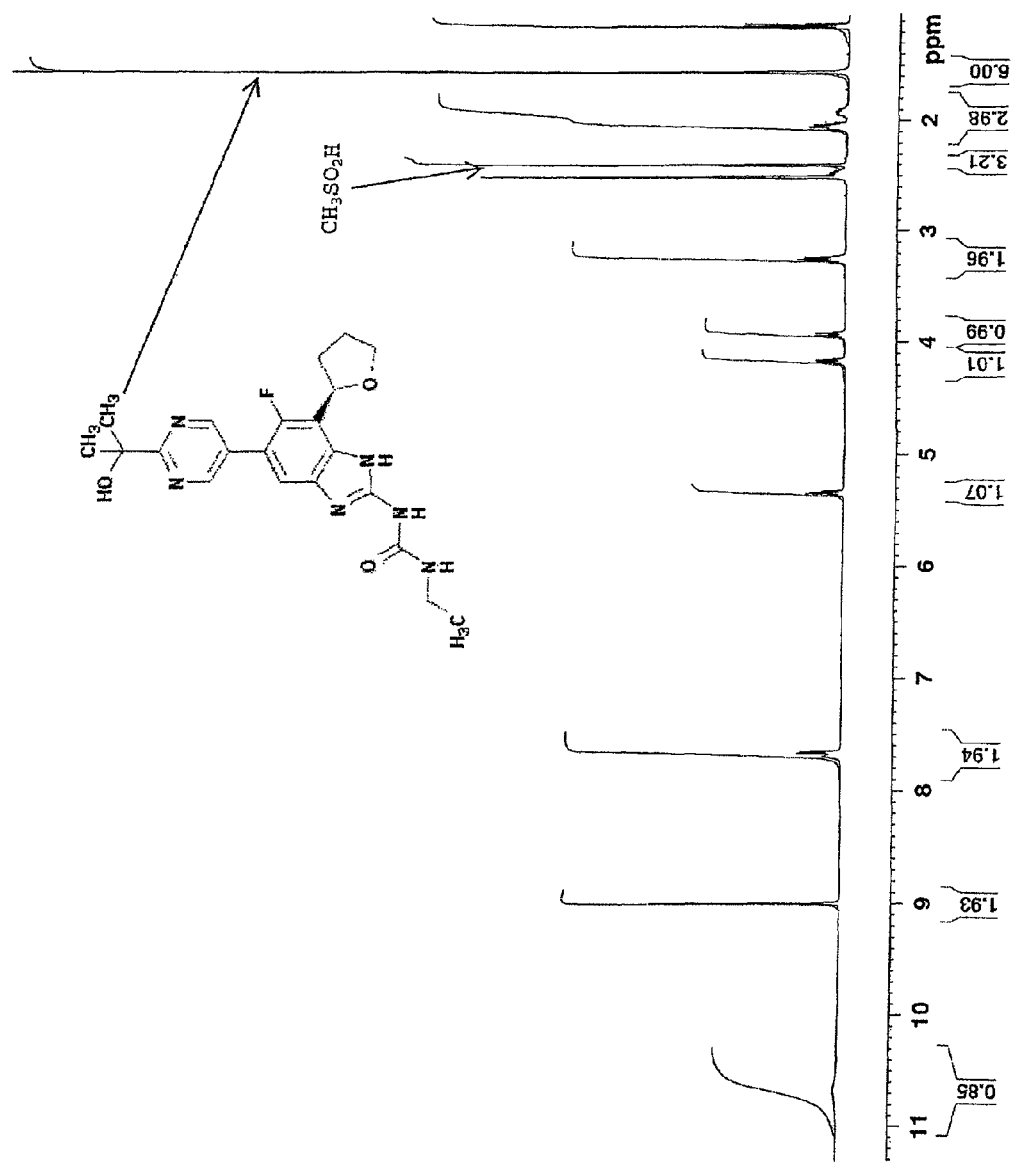
FIG. 10 is a $^1$H-NMR spectrum of the mesylate salt of the 6-fluoro benzimidazolyl urea compound.

The mesylate salt of the 6-fluoro benzimidazolyl urea compound may be converted to an amorphous solid form using any method known to those skilled in the art. The amorphous 6-fluoro benzimidazolyl urea compound mesylate salt may be characterized by the absence of a diffraction pattern characteristic of a crystalline form. The X-ray powder diffraction of a partially amorphous 6-fluoro benzimidazolyl urea compound mesylate salt may still lack features characteristic of a crystal form because the diffraction peaks from the crystalline portion of the sample may be too weak to be observable over the noise. FIG. 9 is an X-ray powder diffraction pattern of an amorphous Form IV of the mesylate salt of the 6-fluoro benzimidazolyl urea compound.

In one embodiment, the amorphous mesylate salt of the 6-fluoro benzimidazolyl urea compound may be prepared by spray drying a solution of the salt in appropriate solvent. Spray drying is well known in the art and is often used to dry thermally-sensitive materials such as pharmaceutical drugs. Spray drying also provides consistent particle distribution that can be reproduced fairly well. Any gas may be used to dry the powder although air is commonly used. If the material is sensitive to air, an inert gas, such nitrogen or argon, may be used. Any method that converts a solution, slurry, suspension or an emulsion of the salt to produce a solid powder may be suitable for preparing the solid amorphous Form IV of the mesylate salt of the 6-fluoro benzimidazolyl urea compound. For example, freeze drying, drum drying, or pulse conversion drying may be used to produce an amorphous mesylate salt of the 6-fluoro benzimidazolyl urea compound.

In one embodiment, a solution of the 6-fluoro benzimidazolyl urea compound in a polar solvent may be spray dried using a nanospray dryer equipped a condenser. The inlet temperature may be kept between 80-120° C.

In another embodiment, the present invention provides an amorphous Form IV of the mesylate salt of the 6-fluoro benzimidazolyl urea compound of formula I:

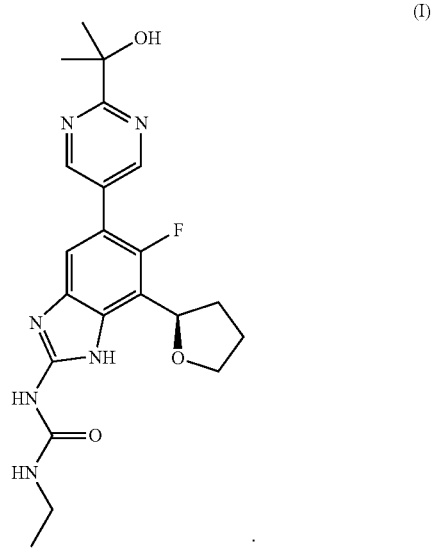 [SMILES: CCNC(=O)Nc1nc2cc(-c3cnc(C(C)(C)O)nc3)c(F)c([C@H]3CCCO3)c2[nH]1]

(I)

In another embodiment, the amorphous Form IV of the mesylate salt of the 6-fluorobenzimidazolyl urea compound is characterized by an X-ray powder diffraction pattern (XPRD) using Cu $K_\alpha$ radiation, characterized by a broad halo with no discernable diffraction peak It is to be understood that solid Forms I and II and amorphous solid Forms III and IV of, respectively, free base and mesylate salt of the 6-fluoro benzimidazolyl urea compound, in addition to having the XRPD, DSC, TGA and other characteristics described herein, may also possess other characteristics not described, such as but not limited to the presence of water or one or more solvent molecules.

X-Ray Powder Diffraction (XRPD): The XRPD pattern of the crystalline forms were recorded at room temperature in reflection mode using a Bruker D8 Discover system equipped with a sealed tube source and a Hi-Star area detector (Bruker AXS, Madison, Wis.). The X-Ray generator was operating at a tension of 40 kV and a current of 35 mA. The powder sample was placed on a Si zero-background wafer. Two frames were registered with an exposure time of 120 s each. The data were subsequently integrated over the range of 3°-41° 2 with a step size of 0.02° and merged into one continuous pattern.

X-Ray Powder Diffraction (XRPD) for amorphous forms: The XRPD pattern of the amorphous solid form was recorded at room temperature in reflection mode using Bruker D8 Advance system equipped with Vantec-1 position sensitive detector (Bruker AXS, Madison, Wis.). The X-Ray generator was operating at a tension of 40 kV and a current of 45 mA. The powder sample was placed on a Si zero-background holder, spinning at 15 rpm during the experiment in a continuous mode using variable slit at the detector. Data was collected from 3 to 40 degrees with 0.0144653 degree increments (0.25 s/step).

Differential Scanning calorimetry (DSC): DSC was performed on a sample of the material using a DSC Q2000 differential scanning calorimeter (TA Instruments, New Castle, Del.). The instrument was calibrated with indium. A sample of approximately 1-2 mg was weighed into an aluminum pan that was crimped using lids with either no pin-hole or pin-hole lids. The DSC samples were scanned from 30° C. to temperatures indicated in the plots at a heating rate of 10° C./min with 50 mL/min nitrogen flow. The samples run under modulated DSC (MDSC) were modulated + and −1° C. every 60 s with ramp rates of 2 or 3° C./min.

Data was collected by Thermal Advantage Q Series™ software and analyzed by Universal Analysis 2000 software (TA Instruments, New Castle, Del.).

Thermogravimetric analysis (TGA): A Model Q5000 Thermogravimetric Analyzer (TA Instruments, New Castle, Del.) was used for TGA measurement. A sample with weight of approximately 3-5 mg was scanned from 30° C. to temperatures indicated on the plots at a heating rate of 10° C./min. Data was collected by Thermal Advantage Q Series™ software and analyzed by Universal Analysis 2000 software (TA Instruments, New Castle, Del.).

The present invention also provides a pharmaceutical composition comprising a compound of formula (I), or a pharmaceutically acceptable salt thereof, and a pharmaceutically acceptable carrier, adjuvant, or vehicle.

The present invention also provides a method of controlling, treating or reducing the advancement, severity or effects of a nosocomial or a non-nosocomial bacterial infection in a patient, comprising administering to said patient a pharmaceutical composition comprising a compound of formula (I), or a pharmaceutically acceptable salt thereof.

In another embodiment, the present invention provides a method of controlling, treating or reducing the advancement, severity or effects of a nosocomial or a non-nosocomial bacterial infection in a patient, comprising administering to said patient a pharmaceutical composition comprising a compound of formula (I), or a pharmaceutically acceptable salt thereof, wherein the bacterial infection is characterized by the presence of one or more of *Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium complex, Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci.

In another embodiment, the present invention provides a method of controlling, treating or reducing the advancement, severity or effects of a nosocomial or a non-nosocomial bacterial infection in a patient, comprising administering to said patient a pharmaceutical composition comprising a compound of formula (I), or a pharmaceutically acceptable salt thereof, wherein the bacterial infection is selected from one or more of the following: upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections, uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial *pneumoniae* (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

In another embodiment, the bacterial infection is selected from one or more of the following: community-acquired bacterial *pneumoniae* (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

According to another embodiment, the invention provides a method of decreasing or inhibiting bacterial quantity in a biological sample. This method comprises contacting said biological sample with a compound of formula (I) or a pharmaceutically acceptable salt thereof.

The term "biological sample", as used herein, includes cell cultures or extracts thereof; biopsied material obtained from a mammal or extracts thereof; and blood, saliva, urine, feces, semen, tears, or other body fluids or extracts thereof. The term "biological sample" also includes living organisms, in which case "contacting a compound of this invention with a biological sample" is synonymous with the term "administering said compound or composition comprising said compound) to a mammal".

The gyrase and/or topoisomerase IV inhibitors of this invention, or pharmaceutical salts thereof, may be formulated into pharmaceutical compositions for administration to animals or humans. These pharmaceutical compositions effective to treat or prevent a bacterial infection which comprise the gyrase and/or topoisomerase IV inhibitor in an amount sufficient to measurably decrease bacterial quantity and a pharmaceutically acceptable carrier, are another embodiment of the present invention. The term "measurably decrease bacterial quantity", as used herein means a measurable change in the number of bacteria between a sample containing said inhibitor and a sample containing only bacteria.

According to another embodiment, the methods of the present invention are useful to treat patients in the veterinarian field including, but not limited to, zoo, laboratory, human companion, and farm animals including primates, rodents, reptiles and birds. Examples of said animals include, but are not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, ostriches, chickens, turkeys, ducks, and geese.

The term "non-nosocomial infections" is also referred to as community acquired infections.

In another embodiment, the bacterial infection is characterized by the presence of one or more of *Streptococcus pneumoniae, Enterococcus faecalis*, or *Staphylococcus aureus*.

In another embodiment, the bacterial infection is characterized by the presence of one or more of *E. coli, Moraxella catarrhalis*, or *Haemophilus influenzae*.

In another embodiment, the bacterial infection is characterized by the presence of one or more of *Clostridium difficile, Neisseria gonorrhoeae, Neisseria meningitidis, Mycobacterium avium complex, Mycobacterium abscessus, Mycobacterium kansasii, Mycobacterium ulcerans, Chlamydophila pneumoniae* and *Chlamydia tracomatis*.

In another embodiment, the bacterial infection is characterized by the presence of one or more of *Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium complex, Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci.

In some embodiments, the bacterial infection is characterized by the presence of one or more of Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant Coagulase negative *staphylococcus*, Fluoroquinolone resistant Coagulase negative *staphylococcus*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, Vancomycin resistant *staphylococcus epidermidis*, Fluoroquinolone resistant *Neisseria gonorrhoeae*, Multidrug Resistant *Pseudomonas aeruginosa* or Cephalosporin resistant *Neisseria gonorrhoeae*.

According to another embodiment, the Methicillin resistant Staphylococci are selected from Methicillin resistant *Staphylococcus aureus*, Methicillin resistant *Staphylococcus epidermidis*, or Methicillin resistant Coagulase negative *staphylococcus*.

In some embodiments, a form of a compound of formula (I), or a pharmaceutically acceptable salt thereof, is used to treat community acquired MRSA (i.e., cMRSA).

In other embodiments, a form of a compound of formula (I), or a pharmaceutically acceptable salt thereof, is used to treat daptomycin resistant organism including, but not limited to, Daptomycin resistant *Enterococcus faecium* and Daptomycin resistant *Staphylococcus aureus*.

According to another embodiment, the Fluoroquinolone resistant Staphylococci are selected from Fluoroquinolone resistant *Staphylococcus aureus*, Fluoroquinolone resistant *Staphylococcus epidermidis*, or Fluoroquinolone resistant Coagulase negative *staphylococcus*.

According to another embodiment, the Glycopeptide resistant Staphylococci are selected from Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, or Hetero vancomycin resistant *Staphylococcus aureus*.

According to another embodiment, the Macrolide-Lincosamide-Streptogramin resistant Staphylococci is Macrolide-Lincosamide-Streptogramin resistant *Staphylococcus aureus*.

According to another embodiment, the Linezolid resistant Enterococci are selected from Linezolid resistant *Enterococcus faecalis*, or Linezolid resistant *Enterococcus faecium*.

According to another embodiment, the Glycopeptide resistant Enterococci are selected from Vancomycin resistant *Enterococcus faecium* or Vancomycin resistant *Enterococcus faecalis*.

According to another embodiment, the β-lactam resistant *Enterococcus faecalis* is β-lactam resistant *Enterococcus faecium*.

According to another embodiment, the Penicillin resistant Streptococci is Penicillin resistant *Streptococcus pneumoniae*.

According to another embodiment, the Macrolide resistant Streptococci is Macrolide resistant *Streptococcus pneumonia*.

According to another embodiment, the Ketolide resistant Streptococci are selected from Macrolide resistant *Streptococcus pneumoniae* and Ketolide resistant *Streptococcus pyogenes*.

According to another embodiment, the Fluoroquinolone resistant Streptococci is Fluoroquinolone resistant *Streptococcus pneumoniae*.

According to another embodiment, the β-lactam resistant *Haemophilus* is β-lactam resistant *Haemophilus influenzae*.

According to another embodiment, the Fluoroquinolone resistant *Haemophilus* is Fluoroquinolone resistant *Haemophilus influenzae*.

According to another embodiment, the Macrolide resistant *Haemophilus* is Macrolide resistant *Haemophilus influenzae*.

According to another embodiment, the Macrolide resistant *Mycoplasma* is Macrolide resistant *Mycoplasma pneumoniae*.

According to another embodiment, the Isoniazid resistant *Mycobacterium* is Isoniazid resistant *Mycobacterium tuberculosis*.

According to another embodiment, the Rifampin resistant *Mycobacterium* is Rifampin resistant *Mycobacterium tuberculosis*.

According to another embodiment, the β-lactam resistant *Moraxella* is β-lactam resistant *Moraxella catarrhalis*.

According to another embodiment, the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Fluoroquinolone resistant *Neisseria gonorrhoeae* or Cephalosporin resistant *Neisseria gonorrhoeae*.

According to another embodiment, the bacterial infection is characterized by the presence of one or more of the following: Methicillin resistant *Staphylococcus aureus*, Methicillin resistant *Staphylococcus epidermidis*, Methicillin resistant Coagulase negative *staphylococcus*, Fluoroquinolone resistant *Staphylococcus aureus*, Fluoroquinolone resistant *Staphylococcus epidermidis*, Fluoroquinolone resistant Coagulase negative *staphylococcus*, Vancomycin resistant *Staphylococcus aureus*, Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Vancomycin resistant *Enterococcus faecium*, Vancomycin resistant *Enterococcus faecalis*, Penicillin resistant *Streptococcus pneumoniae*, Macrolide resistant *Streptococcus pneumoniae*, Fluoroquinolone resistant *Streptococcus pneumoniae*, Macrolide resistant *Streptococcus pyogenes*, or β-lactam resistant *Haemophilus influenzae*.

According to another embodiment, the bacterial infection is characterized by the presence of one or more of the following: Methicillin resistant *Staphylococcus aureus*, Vancomycin resistant *Enterococcus faecium*, Vancomycin resistant *Enterococcus faecalis*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Multidrug Resistant *Pseudomonas aeruginosa*, Isoniazid resistant *Mycobacterium tuberculosis*, and Rifampin resistant *Mycobacterium tuberculosis*.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

Pharmaceutical compositions of this invention comprise a compound of formula (I) or a pharmaceutically acceptable salt thereof and a pharmaceutically acceptable carrier. Such compositions may optionally comprise an additional therapeutic agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an antiviral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as alpha-tocopherol, polyethyleneglycol 1000 succinate, or other similar polymeric delivery matrices.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

Depending upon the particular condition, or disease state, to be treated or prevented, additional therapeutic agents, which are normally administered to treat or prevent that condition, may be administered together with the inhibitors of this invention. Such therapeutic agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. In one embodiment, the compounds of this invention may be used in compositions and methods for treating or protecting individuals against bacterial infections or diseases over a 1-2 week period. In another embodiment, the compounds of this invention may be used in compositions and methods for treating or protecting individuals against bacterial infections or diseases over a 4-8 week period (for example, in the treatment of patients with or at risk for developing endocarditis or osteomyelitis). In another embodiment, the compounds of this invention may be used in compositions and methods for treating or protecting individuals against bacterial infections or diseases over an 8-12 week period. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

In some embodiments, compounds of formula (I), or a pharmaceutically acceptable salt thereof, may be used prophylactically to prevent a bacterial infection. In some embodiments, compounds of formula (I), or a pharmaceutically acceptable salt thereof, may be used before, during or after a dental or surgical procedure to prevent opportunistic infections such as those encountered in bacterial endocarditis. In other embodiments, compounds of formula (I), or a pharmaceutically acceptable salt thereof, may be used prophylactically in dental procedures, including but not limited to extractions, periodontal procedures, dental implant placements and endodontic surgery. In other embodiments, compounds of formula (I), or a pharmaceutically acceptable salt thereof, may be used prophylactically in surgical procedures including but not limited to general surgery, respiratory surgery (tonsillectomy/adenoidectomy), gastrointestinal surgery (upper GI and elective small bowel surgery, esophageal sclerotherapy and dilation, large bowel resections, acute appendectomy), trauma surgery (penetrating abdominal surgery), genito-urinary tract surgery (prostatectomy, urethral dilation, cystoscopy, vaginal or abdominal hysterectomy, cesarean section), transplant surgery (kidney, liver, pancreas or kidney transplantation), head and neck surgery (skin excisions, neck dissections, laryngectomy, head and neck cancer surgeries, mandibular fractures), orthopaedic surgery (total joint replacement, traumatic open fractures), vascular surgery (peripheral vascular procedures), cardiothoracic surgery, coronary bypass surgery, pulmonary resection and neurosurgery.

The term "prevent a bacterial infection" as used herein, unless otherwise indicated, means the prophylactic use of an antibiotic, such as a gyrase and/or topoisomerase IV inhibitor of the present invention, to prevent a bacterial infection. Treatment with a gyrase and/or topoisomerase IV inhibitor could be done prophylactically to prevent an infection caused by an organism that is susceptible to the gyrase and/or topoisomerase IV inhibitor. One general set of conditions where prophylactic treatment could be considered is when an individual is more vulnerable to infection due to, for example, weakened immunity, surgery, trauma, presence of an artificial device in the body (temporary or permanent), an anatomical defect, exposure to high levels of bacteria or possible exposure to a disease-causing pathogen. Examples of factors that could lead to weakened immunity include chemotherapy, radiation therapy, diabetes, advanced age, HIV infection, and transplantation. An example of an anatomical defect would be a defect in the heart valve that increases the risk of bacterial endocarditis. Examples of artificial devices include artificial joints, surgical pins, catheters, etc. Another set of situations where prophylactic use of a gyrase and/or topoisomerase IV inhibitor might be appropriate would be to prevent the spread of a pathogen between individuals (direct or indirect). A specific example of prophylactic use to prevent the spread of a pathogen is the use of a gyrase and/or topoisomerase IV inhibitor by individuals in a healthcare institution (for example a hospital or nursing home).

The compounds of formula (I), or a pharmaceutically acceptable salt thereof, may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula (I), or a pharmaceutically acceptable salt thereof, and another therapeutic or prophylactic agent.

In some embodiments, the additional therapeutic agent or agents is an antibiotic selected from a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide.

In some embodiments, the additional therapeutic agent or agents is an antibiotic selected from a penicillin, a cephalosporin, a quinolone, an aminoglycoside or an oxazolidinone.

In other embodiments, the additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, Ceftaroline and Ceftobiprole, from a Cephamycin including Cefotetan and Cefoxitin, from a carbapenem including Doripenem, Imipenem and Meropenem, from a monobactam including Aztreonam, from a quinolone including Cinoxacin, Nalidixic acid, Oxolininc acid and Pipemidic acid, from a fluoroquinolone including Besifloxacin, Ciprofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Dalbavancin, Televancin, Teicoplanin and Vancomycin, from a streptogramin including Dalfopristin/quinupristin, from an oxazolidone including Linezolid, from a Rifamycin including Rifabutin and Rifampin and from other antibiotics including bactitracin, colistin, Tygacil, Daptomycin, chloramphenicol, clindamycin, isoniazid, metronidazole, mupirocin, polymyxin B, pyrazinamide, trimethoprim/sulfamethoxazole and sulfisoxazole.

In other embodiments, the additional therapeutic agents are selected from a natural penicillin including Penicillin G, from a penicillinase-resistant penicillin including Nafcillin and Oxacillin, from an antipseudomonal penicillin including Pipercillin/tazobactam, from an aminopenicillin including Amoxicillin, from a first generation cephalosporin including Cephalexin, from a second generation cephalosporin including Cefaclor, Cefaclor-CD and Cefuroxime, from a third generation cephalosporin including Ceftazidime and Ceftriaxone, from a fourth generation cephalosporin including Cefepime, from a carbapenem including Imepenem, Meropenem, Ertapenem, Doripenem, Panipenem and Biapenem, a fluoroquinolone including Ciprofloxacin, Gatifloxacin, Levofloxacin and Moxifloxacin, from an aminoglycoside including Tobramycin, from a macrolide including Azithromycin and Clarithromycin, from a Tetracycline including Doxycycline, from a glycopeptide including Vancomycin, from a Rifamycin including Rifampin and from other antibiotics including isoniazid, pyrazinamide, Tygacil, Daptomycin or trimethoprim/sulfamethoxazole.

In some embodiments, a solid form of a compound of formula (I), or a pharmaceutically acceptable salt thereof, can be administered for the treatment of a gram positive infection. In some embodiments, the composition is a solid, liquid (e.g., a suspension), or an iv (e.g., a form of the formula (I) compound, or a pharmaceutically acceptable salt thereof, is dissolved into a liquid and administered iv) composition. In some embodiments, the composition including a formula (I) compound, or a pharmaceutically acceptable salt thereof, is administered in combination with an additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide. In some embodiments, the composition including a solid form of a formula (I) compound, or a pharmaceutically acceptable salt thereof, is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a quinolone, a fluoroquinolone, an aminoglycoside, a macrolide, a ketolide, a polymyxin, a tetracycline, a glycopeptide, a streptogramin, an oxazolidinone, a rifamycin, or a sulfonamide is administered iv.

In some embodiments, a solid form of a formula (I) compound, or a pharmaceutically acceptable salt thereof, can be administered for the treatment of a gram negative infection. In some embodiments, the composition is a solid, liquid (e.g., a suspension), or an iv (e.g., a form of a formula (I) compound, or a pharmaceutically acceptable salt thereof, is dissolved into a liquid and administered iv) composition. In some embodiments the composition including a formula (I) compound, or a pharmaceutically acceptable salt thereof, is administered in combination with an additional antibiotic agent, selected from a: natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a polymyxin, tetracycline or a sulfonamide. In some embodiments, the composition including a solid form of a formula (I) compound, or a pharmaceutically acceptable salt thereof, is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a polymyxin, tetracycline or a sulfonamide is administered orally. In some embodiments, the additional therapeutic agent is administered iv.

The additional therapeutic agents described above may be administered separately, as part of a multiple dosage regimen, from the inhibitor-containing composition. Alternatively, these agents may be part of a single dosage form, mixed together with the inhibitor in a single composition.

The pharmaceutical compositions of this invention may be administered orally, parenterally, by inhalation spray, topically, rectally, nasally, buccally, vaginally or via an implanted reservoir. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical, compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

According to another embodiment, compounds of formula (I), or a pharmaceutically acceptable salt thereof, may also be delivered by implantation (e.g., surgically), such as with an implantable or indwelling device. An implantable or indwelling device may be designed to reside either permanently or temporarily in a subject. Examples of implantable and indwelling devices include, but are not limited to, contact lenses, central venous catheters and needleless connectors, endotracheal tubes, intrauterine devices, mechanical heart valves, pacemakers, peritoneal dialysis catheters, prosthetic joints, such as hip and knee replacements, tympanostomy tubes, urinary catheters, voice prostheses, stents, delivery pumps, vascular filters and implantable control release compositions. Biofilms can be detrimental to the health of patients with an implantable or indwelling medical device because they introduce an artificial substratum into the body and can cause persistent infections. Thus, providing compounds of formula (I), or a pharmaceutically acceptable salt thereof, in or on the implantable or indwelling device can prevent or reduce the production of a biofilm. In addition, implantable or indwelling devices may be used as a depot or reservoir of compounds of formula (I), or a pharmaceutically acceptable salt thereof. Any implantable or indwelling device can be used to deliver compounds of formula (I), or a pharmaceutically acceptable salt thereof, provided that a) the device, compounds of formula (I), or a pharmaceutically acceptable salt thereof, and any pharmaceutical composition including compounds of formula (I), or a pharmaceutically acceptable salt thereof, are biocompatible, and b) that the device can deliver or release an effective amount of compounds of formula (I), or a pharmaceutically acceptable salt thereof, to confer a therapeutic effect on the treated patient.

Delivery of therapeutic agents via implantable or indwelling devices is known in the art. See for example, "Recent Developments in Coated Stents" by Hofma et al. published in *Current Interventional Cardiology Reports* 2001, 3:28-36, the entire contents of which, including references cited therein, incorporated herein by reference. Other descriptions of implantable devices can be found in U.S. Pat. Nos. 6,569, 195 and 6,322,847; and U.S. Patent Application Numbers 2004/0044405, 2004/0018228, 2003/0229390, 2003/0225450, 2003/0216699 and 2003/0204168, each of which is incorporated herein by reference in its entirety.

In some embodiments, the implantable device is a stent. In one specific embodiment, a stent can include interlocked meshed cables. Each cable can include metal wires for structural support and polymeric wires for delivering the therapeutic agent. The polymeric wire can be dosed by immersing the polymer in a solution of the therapeutic agent. Alternatively, the therapeutic agent can be embedded in the polymeric wire during the formation of the wire from polymeric precursor solutions.

In other embodiments, implantable or indwelling devices can be coated with polymeric coatings that include the therapeutic agent. The polymeric coating can be designed to control the release rate of the therapeutic agent. Controlled release of therapeutic agents can utilize various technologies. Devices are known that have a monolithic layer or coating incorporating a heterogeneous solution and/or dispersion of an active agent in a polymeric substance, where the diffusion of the agent is rate limiting, as the agent diffuses through the polymer to the polymer-fluid interface and is released into the surrounding fluid. In some devices, a soluble substance is also dissolved or dispersed in the polymeric material, such that additional pores or channels are left after the material dissolves. A matrix device is generally diffusion limited as well, but with the channels or other internal geometry of the device also playing a role in releasing the agent to the fluid. The channels can be pre-existing channels or channels left behind by released agent or other soluble substances.

Erodible or degradable devices typically have the active agent physically immobilized in the polymer. The active agent can be dissolved and/or dispersed throughout the polymeric material. The polymeric material is often hydrolytically degraded over time through hydrolysis of labile bonds, allowing the polymer to erode into the fluid, releasing the active agent into the fluid. Hydrophilic polymers have a generally faster rate of erosion relative to hydrophobic polymers. Hydrophobic polymers are believed to have almost purely surface diffusion of active agent, having erosion from the surface inwards. Hydrophilic polymers are believed to allow water to penetrate the surface of the polymer, allowing hydrolysis of labile bonds beneath the surface, which can lead to homogeneous or bulk erosion of polymer.

The implantable or indwelling device coating can include a blend of polymers each having a different release rate of the therapeutic agent. For instance, the coating can include a polylactic acid/polyethylene oxide (PLA-PEO) copolymer and a polylactic acid/polycaprolactone (PLA-PCL) copolymer. The polylactic acid/polyethylene oxide (PLA-PEO) copolymer can exhibit a higher release rate of therapeutic agent relative to the polylactic acid/polycaprolactone (PLA-PCL) copolymer. The relative amounts and dosage rates of therapeutic agent delivered over time can be controlled by controlling the relative amounts of the faster releasing polymers relative to the slower releasing polymers. For higher initial release rates the proportion of faster releasing polymer can be increased relative to the slower releasing polymer. If most of the dosage is desired to be released over a long time period, most of the polymer can be the slower releasing polymer. The device can be coated by spraying the device with a solution or dispersion of polymer, active agent, and solvent. The solvent can be evaporated, leaving a coating of polymer and active agent. The active agent can be dissolved and/or dispersed in the polymer. In some embodiments, the co-polymers can be extruded over the device.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections.

Typically, the pharmaceutical compositions of this invention will be administered from about 1 to 5 times per day or alternatively, as a continuous infusion. Alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula (I), or a pharmaceutically acceptable salt thereof, and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

According to another embodiment, the invention provides methods for treating or preventing a bacterial infection, or disease state, comprising the step of administering to a patient any compound, pharmaceutical composition, or combination described herein. The term "patient", as used herein, means an animal, preferably a mammal, and most preferably a human.

The compounds of this invention are also useful as commercial reagents which effectively bind to the gyrase B and/or topoisomerase IV enzymes. As commercial reagents, the compounds of this invention, and their derivatives, may be used to block gyrase B and/or topoisomerase IV activity in biochemical or cellular assays for bacterial gyrase B and/or topoisomerase IV or their homologs or may be derivatized to bind to a stable resin as a tethered substrate for affinity chromatography applications. These and other uses which characterize commercial gyrase B and/or topoisomerase IV inhibitors will be evident to those of ordinary skill in the art.

In order that this invention be more fully understood, the following schemes and examples are set forth. These examples are for the purpose of illustration only and are not to be construed as limiting the scope of the invention in any way.

The following definitions describe terms and abbreviations used herein:

Ac acetyl
Bu butyl
Et ethyl
Ph phenyl
Me methyl
THF tetrahydrofuran
DCM dichloromethane
$CH_2Cl_2$ dichloromethane
EtOAc ethyl acetate
$CH_3CN$ acetonitrile
EtOH ethanol
$Et_2O$ diethyl ether
MeOH methanol
MTBE methyl tert-butyl ether
DMF N,N-dimethylformamide
DMA N,N-dimethylacetamide
DMSO dimethyl sulfoxide
HOAc acetic acid
TEA triethylamine
TFA trifluoroacetic acid
TFAA trifluoroacetic anhydride
$Et_3N$ triethylamine
DIPEA diisopropylethylamine
DIEA diisopropylethylamine
$K_2CO_3$ potassium carbonate
$Na_2CO_3$ sodium carbonate
$Na_2S_2O_3$ sodium thiosulfate
$Cs_2CO_3$ cesium carbonate
$NaHCO_3$ sodium bicarbonate NaOH sodium hydroxide
Na$_2$SO$_4$ sodium sulfate
MgSO$_4$ magnesium sulfate
K$_3$PO$_4$ potassium phosphate
NH$_4$Cl ammonium chloride
LC/MS liquid chromatography/mass spectra
GCMS gas chromatography mass spectra
HPLC high performance liquid chromatography
GC gas chromatography
LC liquid chromatography
IC ion chromatography
IM intramuscular
CFU/cfu colony forming units
MIC minimum inhibitory concentration
Hr or h hours
atm atmospheres
rt or RT room temperature
TLC thin layer chromatography
HCl hydrochloric acid
H$_2$O water
EtNCO ethyl isocyanate
Pd/C palladium on carbon
NaOAc sodium acetate
H$_2$SO$_4$ sulfuric acid
N$_2$ nitrogen gas
H$_2$ hydrogen gas
n-BuLi n-butyl lithium
DI de-ionized
Pd(OAc)$_2$ palladium(II)acetate
PPh$_3$ triphenylphosphine
i-PrOH isopropyl alcohol
NBS N-bromosuccinimide
Pd[(Ph$_3$)P]$_4$ tetrakis(triphenylphosphine)palladium(0)
PTFE polytetrafluoroethylene
rpm revolutions per minute
SM starting material
Equiv. equivalents
$^1$H-NMR proton nuclear magnetic resonance
Synthesis of the Compounds

EXAMPLES

The 6-Fluoro Benzimidazolyl Urea Compound

Synthesis of (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea Scheme 3 provides a method for preparing the 6-fluoro benzoimidazolyl urea compound.

Scheme 3

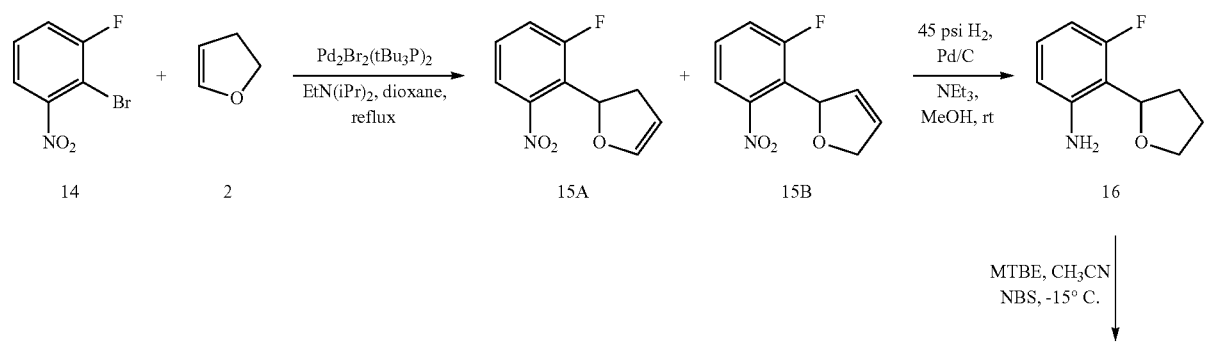

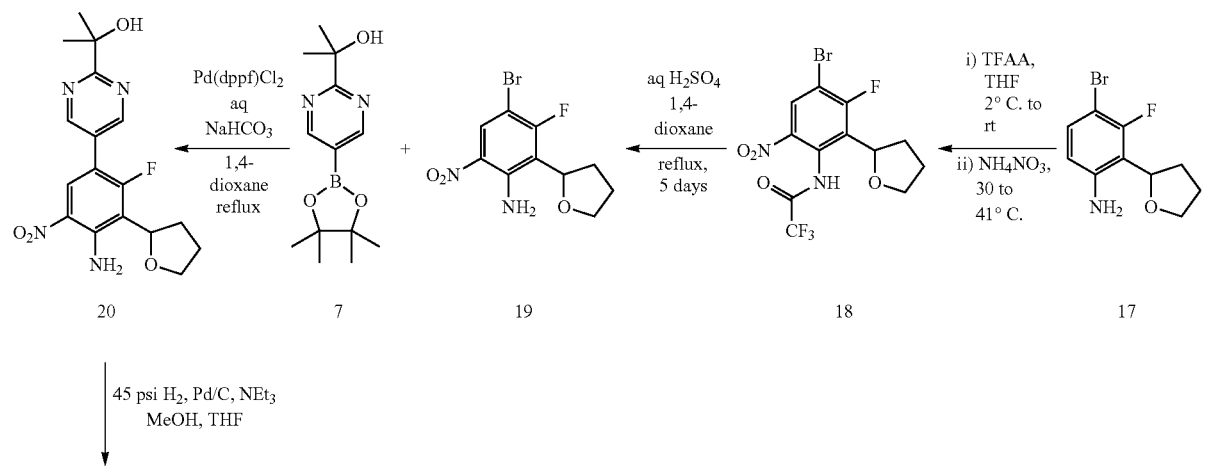

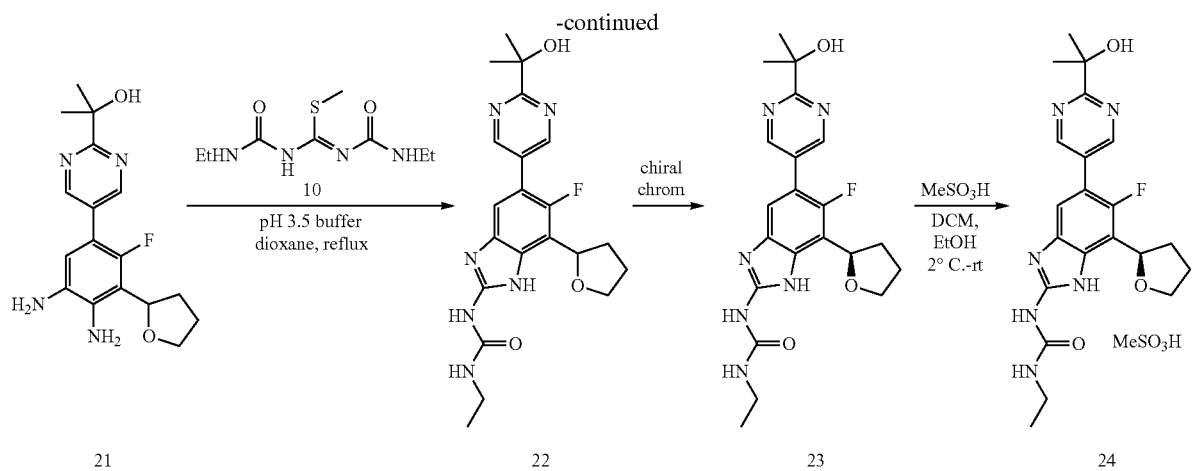

Example 1.a

Preparation of 2-(2-fluoro-6-nitro-phenyl)-2,3-dihydrofuran (15A) and 2-(2-fluoro-6-nitro-phenyl)-2,5-dihydrofuran (15B)

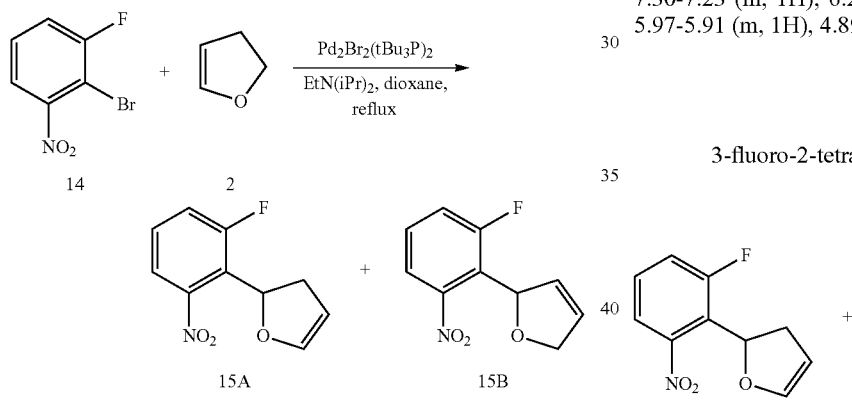

2-Bromo-1-fluoro-3-nitro-benzene (14) (200.3 g, 98%, 892.3 mmol, Bosche F6657), 1,4-dioxane (981.5 mL, Sigma-Aldrich 360481), and 2,3-dihydrofuran (2) (341.1 mL, 99%, 4.462 mol, Aldrich 200018) were charged in a reaction flask, followed by N,N-diisopropylethylamine (155.4 mL, 892.3 mmol, Sigma-Aldrich 550043) and bromo(tri-tert-butylphosphine)palladium(I) dimer (6.936 g, 8.923 mmol, Johnson Matthey C4099). The mixture was stirred at reflux for 2 hrs (HPLC showed 98% consumption of starting arylbromide). The reaction mixture was allowed to cool; the precipitate was removed by filtration, rinsed with EtOAc, and the filtrate concentrated in vacuo to a dark reddish brown semi-solid oil. The semi-solid oil was dissolved in CH$_2$Cl$_2$, eluted through a plug of silica with CH$_2$Cl$_2$, and concentrated in vacuo giving a mixture of 15A and 15B as a dark amber oil (291.3 g). The crude product was carried forward without further purification. The major product was 2-(2-fluoro-6-nitro-phenyl)-2,3-dihydrofuran (15A) (96%): LCMS (C18 column eluting with 10-90% CH$_3$CN/water gradient over 5 minutes with formic acid modifier) M+1: 210.23 (3.13 min); $^1$H NMR (300 MHz, CDCl$_3$) δ 7.54 (dt, J=8.0, 1.2 Hz, 1H), 7.43 (td, J=8.2, 5.2 Hz, 1H), 7.32 (ddd, J=9.7, 8.3, 1.3 Hz, 1H), 6.33 (dd, J=4.9, 2.4 Hz, 1H), 5.80 (t, J=10.9 Hz, 1H), 5.06 (q, J=2.4 Hz, 1H), 3.18-3.07 (m, 1H), 2.94-2.82 (m, 1H) ppm. The minor product was 2-(2-fluoro-6-nitro-phenyl)-2,5-dihydrofuran (15B) (4%): GCMS (Agilent HP-5MS 30 m×250 µm×0.25 µm column heating at 60° C. for 2 min to 300° C. over 15 min with a 1 mL/min flow rate) M+1: 210 (11.95 min). $^1$H NMR (300 MHz, CDCl$_3$) δ 7.47 (d, J=8.0 Hz, 1H), 7.43-7.34 (m, 1H), 7.30-7.23 (m, 1H), 6.21-6.15 (m, 1H), 6.11-6.06 (m, 1H), 5.97-5.91 (m, 1H), 4.89-4.73 (m, 2H) ppm.

Example 1.b

Preparation of 3-fluoro-2-tetrahydrofuran-2-yl-aniline (16)

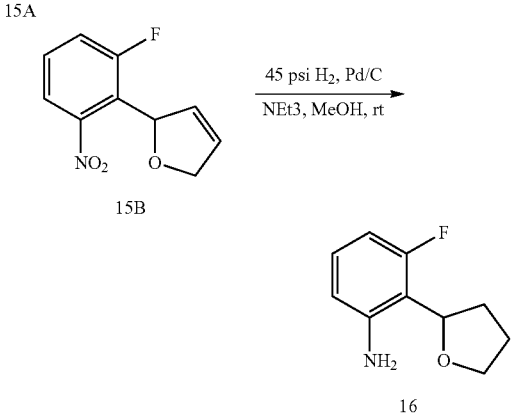

5% Palladium on carbon (37.3 g, 50% wet, 8.76 mmol, Aldrich 330116) was placed in a Parr bottle under nitrogen, followed by MeOH (70 mL, JT-Baker 909333). The crude mixture of 2-(2-fluoro-6-nitro-phenyl)-2,3-dihydrofuran and 2-(2-fluoro-6-nitro-phenyl)-2,5-dihydrofuran (15A&15B) (186.6 g, 892.1 mmol) dissolved in MeOH (117 mL) was added to the Parr bottle, followed by NEt₃ (124.3 mL, 892.1 mmol, Sigma-Aldrich 471283). The bottle was placed on a Parr shaker and saturated with H₂. After adding 45 psi H₂, the reaction mixture was shaken until consumption of the starting material was complete (HPLC and LCMS showed complete reaction). The reaction mixture was purged with nitrogen, filtered through Celite™ and rinsed with EtOAc. The filtrate was concentrated on a rotary evaporator giving brown oil, which was dissolved in Et₂O and washed with water (2×). The ether phase was extracted with aqueous 1 N HCl (5×250 mL), which was washed with Et₂O (3×) and then basified with aqueous 6 N NaOH to pH 12-14. The basic aqueous phase was extracted with dichloromethane (CH₂Cl₂, 4×), and the combined organic extract was washed with saturated aqueous NH₄Cl, dried over MgSO₄, and filtered through a pad of silica eluting with CH₂Cl₂ to 25% EtOAc/hexane. The desired filtrate was concentrated under reduced pressure giving 16 as a light brown oil (121.8 g, 84% GCMS plus NMR purity). GCMS (Agilent HP-5MS 30 m×250 μm×0.25 μm column heating at 60° C. for 2 min to 300° C. over 15 min with a 1 mL/min flow rate) M+1: 182.0 (11.44 min). LCMS (C18 column eluting with 10-90% CH₃CN/water gradient over 5 minutes with formic acid modifier) M+1: 182.10 (2.61 min). ¹H NMR (300 MHz, CDCl₃) δ 6.97 (td, J=8.1, 6.3 Hz, 1H), 6.43-6.35 (m, 2H), 5.21-5.13 (m, 1H), 4.54 (s, 2H), 4.16-4.07 (m, 1H), 3.90-3.81 (m, 1H), 2.23-2.00 (m, 4H) ppm. Additional crops were obtained as follows: the combined ether phase was washed with saturated aqueous NaHCO₃, brine, dried over Na₂SO₄, decanted, and concentrated under reduced pressure. The oil was vacuum distilled (ca. 15 ton) collecting the distillate at 101-108° C. To a stirring solution of the distilled oil in EtOH (1 volume) at 2° C. was slowly added 5 M HCl (1 eq) in iPrOH. The resulting suspension was brought to room temperature, diluted with EtOAc (3 volumes, vol/vol), and stirred for 2 hrs. A white solid was collected by filtration, washed with EtOAc, and dried under reduced pressure giving a second crop of product as the HCl salt. The mother liquor was concentrated to a slurry, diluted with EtOAc and the solid collected by filtration, washed with EtOAc, and dried in vacuo giving the HCl salt as a third crop of the product. LCMS (C18 column eluting with 10-90% CH₃CN/water gradient over 5 minutes with formic acid modifier) M+1: 182.10 (2.58 min). ¹H NMR (300 MHz, CDCl₃) δ 10.73 (br.s, 3H), 7.66 (d, J=8.1 Hz, 1H), 7.33 (td, J=8.2, 5.9 Hz, 1H), 7.13-7.05 (m, 1H), 5.26 (dd, J=9.0, 6.5 Hz, 1H), 4.38-4.28 (m, 1H), 4.00-3.91 (m, 1H), 2.59-2.46 (m, 1H), 2.30-1.95 (m, 3H) ppm. The overall yield from the three crops was 76%.

Example 1.c

Preparation of 4-bromo-3-fluoro-2-tetrahydrofuran-2-yl-aniline (17)

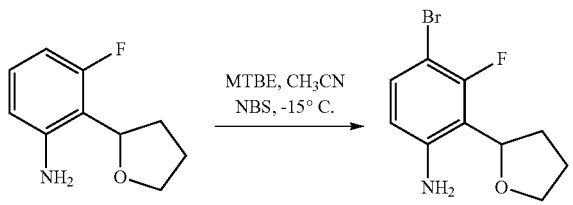

To a stirring solution of 3-fluoro-2-tetrahydrofuran-2-yl-aniline (16) (131.9 g, 92%, 669.7 mmol) in methyl tert-butyl ether (1.456 L) and acetonitrile (485 mL) cooled to −20° C. was added N-bromosuccinimide (120.4 g, 99%, 669.7 mmol, Aldrich B81255) in 3 portions maintaining a reaction temperature below about −15° C. After complete addition, stirring was continued at −15 to −10° C. for 30 minutes. ¹H NMR of a worked-up aliquot showed 96% consumption of starting aniline. Another 4.82 g NBS was added to the reaction mixture and stirred at −10° C. for additional 30 minutes. Aqueous 1 N Na₂S₂O₃ (670 mL) was added to the reaction mixture. The cold bath was removed, the mixture stirred for 20 minutes, then diluted with EtOAc. The layers were separated. The organic phase was washed with saturated aqueous NaHCO₃ (2×), water, and brine, dried over Na₂SO₄, decanted, and concentrated under reduced pressure giving a dark amber oil. The residue was diluted with hexane and eluted through a short plug of silica with 25% EtOAc/hexane to 50% EtOAc/hexane. The desired filtrate was concentrated in vacuo giving 17 as a dark amber oil (182.9 g, 90% yield; 86% NMR purity). LCMS (C18 column eluting with 10-90% AcN/water gradient over 5 minutes with formic acid modifier) M+1: 260.12 (3.20 min). ¹H NMR (300 MHz, CDCl₃) δ 7.15 (dd, J=8.6, 7.6 Hz, 1H), 6.30 (dd, J=8.7, 1.3 Hz, 1H), 5.19-5.12 (m, 1H), 4.58 (s, 2H), 4.16-4.07 (m, 1H), 3.90-3.81 (m, 1H), 2.23-1.99 (m, 4H) ppm.

Example 1.d

Preparation of N-(4-bromo-3-fluoro-6-nitro-2-tetrahydrofuran-2-yl-phenyl)-2,2,2-trifluoro-acetamide (18)

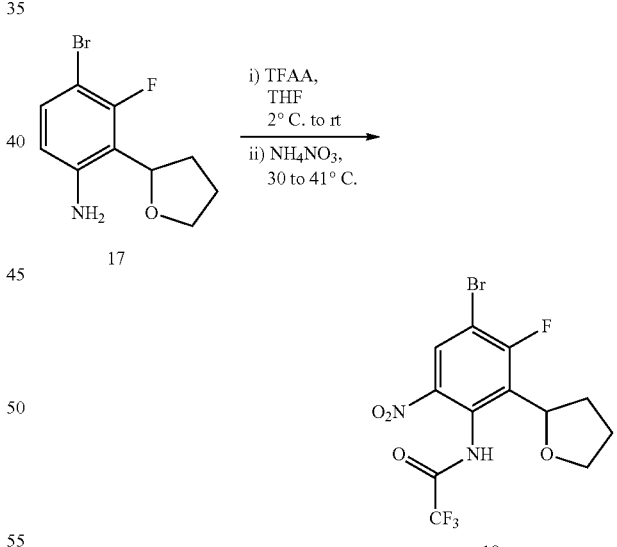

To trifluoroacetic anhydride (565.3 mL, 4.067 mol, Sigma-Aldrich 106232) stirring at 2° C. was slowly added neat 4-bromo-3-fluoro-2-tetrahydrofuran-2-yl-aniline (17) (123.0 g, 86%, 406.7 mmol) as a thick oil via addition funnel over about 20 minutes (reaction temperature rose to 13° C.). The remaining oil was rinsed into the reaction mixture with anhydrous THF (35 mL). The cold bath was removed and the reaction was heated to 35° C., followed by portion-wise addition of NH₄NO₃ (4.88 g×20 portions, 1.22 mol, Sigma-Aldrich A7455) over 2.5 hrs maintaining the reaction temperature between 30 and 41° C. using an ice-water bath only as needed to control the exotherm. After complete addition the reaction mixture was stirred for another 10 minutes (HPLC showed reaction 99% complete). It was slowly poured into crushed ice (1.23 kg) and stirred for 1 hr to allow formation of a filterable solid precipitate, which was collected and washed with water, sparingly with saturated aqueous NaHCO$_3$, and water again (to pH 7). The product was dried in a convection oven overnight at 40° C. and then under reduced pressure in an oven at 50° C. overnight giving 18 as a beige solid (152.5 g, 90% yield; 96% HPLC purity). LCMS (C18 column eluting with 10-90% CH$_3$CN/water gradient over 5 minutes with formic acid modifier) M+1: 401.30 (3.41 min). $^1$H NMR (300 MHz, CDCl$_3$) δ 10.56 (s, 1H), 8.19 (d, J=6.6 Hz, 1H), 5.22 (dd, J=10.3, 6.4 Hz, 1H), 4.22 (dd, J=15.8, 7.2 Hz, 1H), 3.99 (dd, J=16.1, 7.5 Hz, 1H), 2.50-2.38 (m, 1H), 2.22-2.11 (m, 2H), 1.86-1.71 (m, 1H) ppm.

Example 1.e

Preparation of 4-bromo-3-fluoro-6-nitro-2-tetrahydrofuran-2-yl-aniline (19)

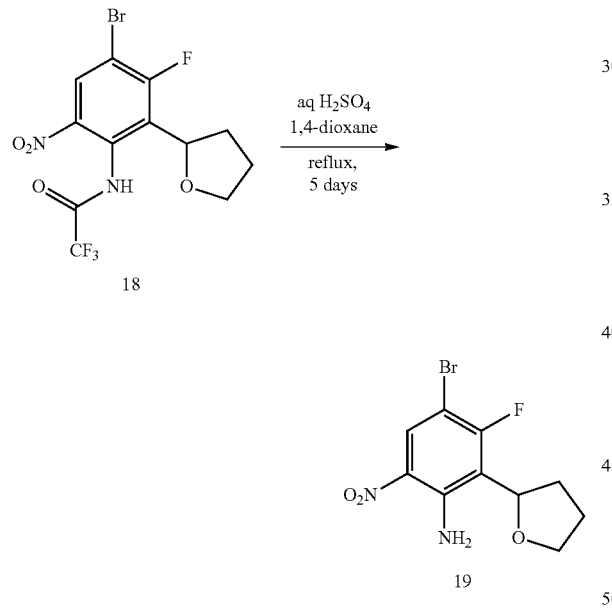

A reaction flask was charged with N-(4-bromo-3-fluoro-6-nitro-2-tetrahydrofuran-2-yl-phenyl)-2,2,2-trifluoro-acetamide (18) (242.3 g, 604.1 mmol), 1,4-dioxane (1.212 L), and aqueous 2 M sulfuric acid (362.4 mL, 724.9 mmol), and stirred at reflux for 5 days (HPLC showed 98% conversion). The reaction mixture was allowed to cool, diluted with EtOAc, neutralized with saturated aqueous NaHCO$_3$, separated the layers, and re-extracted the aqueous phase with EtOAc (2×). The combined organic phase was washed with brine (2×), dried over MgSO$_4$, filtered and concentrated in vacuo giving 19 as a greenish brown solid (181.7 g, 94% yield; 95% HPLC purity). The product was carried to the next step without further purification. LCMS (C18 column eluting with 10-90% CH$_3$CN/water gradient over 5 minutes with formic acid modifier) M+1: 305.20 (3.63 min). $^1$H NMR (300 MHz, CDCl$_3$) δ 8.35 (d, J=7.3 Hz, 1H), 7.45 (s, 2H), 5.23-5.16 (m, 1H), 4.23-4.14 (m, 1H), 3.93-3.84 (m, 1H), 2.31-1.96 (m, 4H) ppm.

Example 1.f

Preparation of 2-[5-(4-amino-2-fluoro-5-nitro-3-tetrahydrofuran-2-yl-phenyl)pyrimidin-2-yl]propan-2-ol (20)

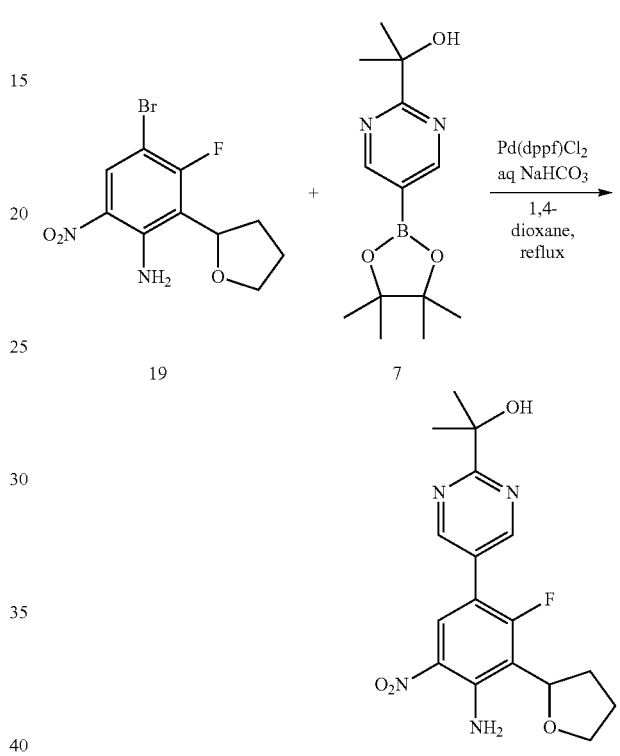

To a stirring solution of 4-bromo-3-fluoro-6-nitro-2-tetrahydrofuran-2-yl-aniline (19) (525.0 g, 1.721 mol, Bridge Organics Co.) in 1,4-dioxane (4.20 L, Sigma-Aldrich 360481) was added a 1.2 M aqueous solution of NaHCO$_3$ (4.302 L, 5.163 mol). A stream of nitrogen was bubbled through the stirring mixture for 2 hrs, followed by addition of 2-[5-(4,4,5,5-tetramethyl-1,3,2-dioxaborolan-2-yl)pyrimidin-2-yl]propan-2-ol (7) (545.4 g, 2.065 mol, Bridge Organics Co.) and 1,1'-bis(diphenylphosphino)ferrocene dichloropalladium dichloromethane adduct (42.16 g, 51.63 mmol, Strem 460450). The reaction mixture was stirred at reflux overnight, allowed to cool, diluted with EtOAc (8.4 L), and the layers were separated. The organic phase was washed with saturated aqueous NH$_4$Cl and then brine. The aqueous phase was re-extracted with EtOAc (4 L) and washed this organic extract with brine. The combined organic phase was dried over MgSO$_4$, filtered through a short plug of Florisil®, eluted with EtOAc, and the filtrate concentrated on a rotary evaporator giving a dark brown wet solid. This was dissolved in CH$_2$Cl$_2$, loaded on a pad of silica gel, eluted with hexane, then 25% EtOAc/hexane, and then 50% EtOAc/hexane. The desired filtrate was concentrated on a rotary evaporator to a thick suspension, and the solid was collected by filtration, triturated with MTBE, and dried in vacuo giving 20 as a bright yellow solid (55.8% yield, 90-97% HPLC purity). The filtrate was concentrated and the above purification was repeated giving a second crop of 20 as a bright yellow solid (19.7% yield). The filtrate was again concentrated giving a dark brown oil and this was loaded on a silica column with toluene and minimal $CH_2Cl_2$. It was eluted with EtOAc/hexane (0% to 50%). The desired fractions were concentrated to a slurry and diluted with MTBE/hexane. The solid was collected by filtration and washed with minimal MTBE giving a third crop of 20 as a bright yellow solid (4.9% yield) with an overall yield of 80% from the three crops. LCMS (C18 column eluting with 10-90% $CH_3CN$/water gradient over 5 minutes with formic acid modifier) M+1: 363.48 (2.95 min). $^1$H NMR (300 MHz, $CDCl_3$) δ 8.84 (d, J=1.6 Hz, 2H), 8.27 (d, J=8.0 Hz, 1H), 7.62 (s, 2H), 5.31-5.24 (m, 1H), 4.63 (s, 1H), 4.27-4.18 (m, 1H), 3.97-3.87 (m, 1H), 2.33-2.05 (m, 4H), 1.64 (s, 6H) ppm.

Example 1.g

Preparation of 2-[5-(4,5-diamino-2-fluoro-3-tetrahydrofuran-2-yl-phenyl)pyrimidin-2-yl]propan-2-ol (21)

and rinsed with EtOAc. It was re-filtered through paper (glass microfibre) and the filtrate concentrated in vacuo. The reaction was repeated three more times on the same scale and the batches were combined giving 21 as a brown solid (447 g, 99% yield; 93% HPLC purity). LCMS (C18 column eluting with 10-90% $CH_3CN$/water gradient over 5 minutes with formic acid modifier) M+1: 333.46 (1.79 min). $^1$H NMR (300 MHz, $CDCl_3$) δ 8.81 (d, J=1.4 Hz, 2H), 6.69 (d, J=7.3 Hz, 1H), 5.27-5.20 (m, 1H), 4.73 (s, 1H), 4.70 (s, 2H), 4.23-4.14 (m, 1H), 3.94-3.86 (m, 1H), 3.22 (s, 2H), 2.32-2.22 (m, 1H), 2.18-1.99 (m, 3H), 1.63 (s, 6H) ppm.

Example 1.h

Preparation of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22)

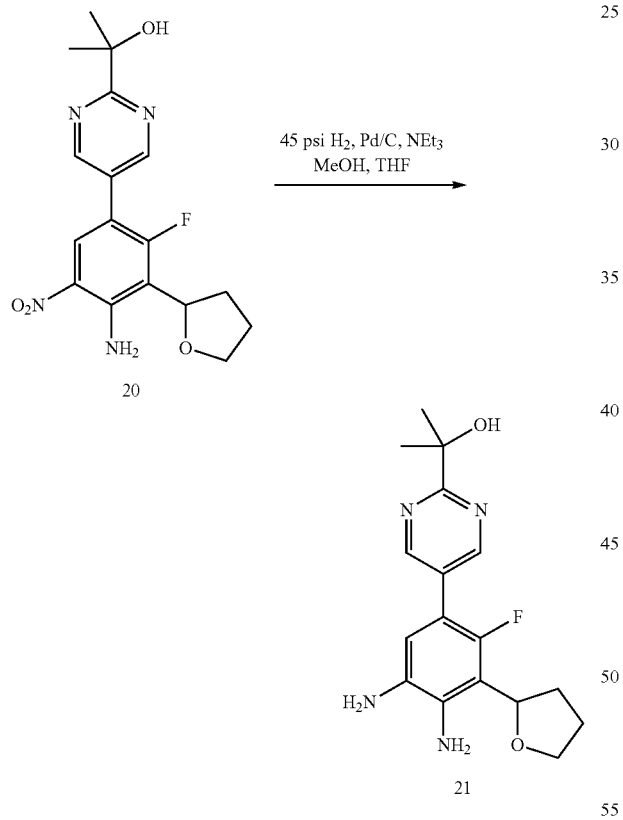

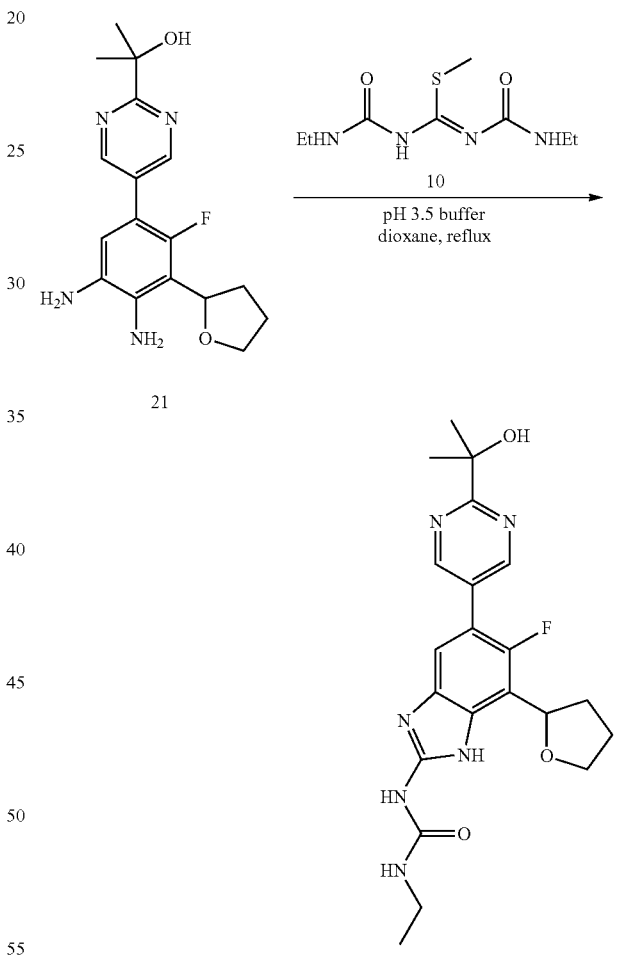

5% Palladium on carbon (14.21 g, 50% wet, 3.339 mmol, Aldrich 330116) was placed in a Parr bottle under nitrogen, followed by MeOH (242 mL, JT-Baker 909333) and $NEt_3$ (46.54 mL, 333.9 mmol, Sigma-Aldrich 471283). 2-[5-(4-Amino-2-fluoro-5-nitro-3-tetrahydrofuran-2-yl-phenyl)pyrimidin-2-yl]propan-2-ol (20) (121.0 g, 333.9 mmol) was dissolved in hot THF (360 mL), allowed to cool, added to the reaction mixture, and rinsed the residual amount of 20 with another portion of THF (124 mL). The bottle was placed on a Parr shaker and saturated with $H_2$. After adding 45 psi $H_2$, the bottle was shaken until consumption of 20 was complete (HPLC and LCMS showed complete reaction). The reaction mixture was purged with nitrogen, filtered through Celite™

To a stirring suspension of 2-[5-(4,5-diamino-2-fluoro-3-tetrahydrofuran-2-yl-phenyl)pyrimidin-2-yl]propan-2-ol (21) (111.3 g, 334.9 mmol) and 1,4-dioxane (556.5 mL, Sigma-Aldrich 360481) was added 1-ethyl-3-(N-(ethylcarbamoyl)-C-methylsulfanyl-carbonimidoyl)urea (10) (93.36 g, 401.9 mmol, CB Research and Development) followed by a pH 3.5 buffer (1.113 L), prepared by dissolving NaOAc trihydrate (158.1 g) in 1N aqueous $H_2SO_4$ (1.100 L). The reaction mixture was stirred at reflux overnight (HPLC showed complete conversion), cooled to room temperature, and poured portion-wise (to minimize frothing) into a stirring solution of aqueous saturated NaHCO$_3$ (2.23 L) giving pH 8-9. The resulting mixture was stirred for 30 minutes, the solid was collected by filtration, washed copiously with water to neutral pH, and then more sparingly with EtOH. The solid was dried under reduced pressure giving 22 as an off-white yellowish solid (135.2 g, 94% yield; 99% HPLC purity). LCMS (C18 column eluting with 10-90% CH$_3$CN/water gradient over 5 minutes with formic acid modifier) M+1: 429.58 (2.03 min). $^1$H NMR (300 MHz, MeOD) δ 8.95 (d, J=1.6 Hz, 2H), 7.45 (d, J=6.5 Hz, 1H), 5.38 (br.s, 1H), 4.27 (dd, J=14.9, 7.1 Hz, 1H), 4.01 (dd, J=15.1, 7.0 Hz, 1H), 3.37-3.29 (m, 2H), 2.55 (br.s, 1H), 2.19-2.07 (m, 2H), 2.02-1.82 (br.s, 1H), 1.63 (s, 6H), 1.21 (t, J=7.2 Hz, 3H) ppm.

Example 1.i

Chiral chromatographic isolation of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23)

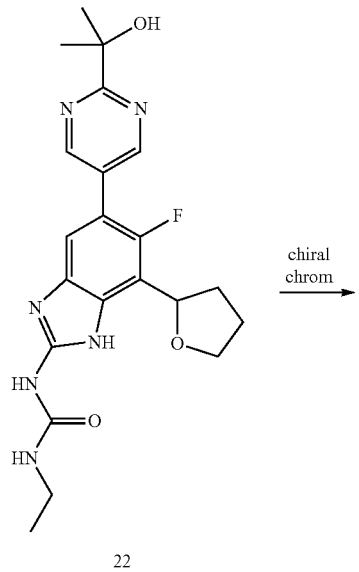

A racemic sample of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22) (133.60 g) was resolved on a CHIRALPAK® IC® column (by Chiral Technologies) eluting with CH$_2$Cl$_2$/MeOH/TEA (60/40/0.1) at 25° C. giving the desired enantiomer 23 as an off-white solid (66.8 g, 45% yield; 99.8% HPLC purity, 99+%ee). Analytical chiral HPLC retention time was 7.7 min (CHIRALPAK® IC® 4.6×250 mm column, 1 mL/min flow rate, 30° C.). The solid was suspended in 2:1 EtOH/Et$_2$O (5 volumes), stirred for 10 minutes, collected by filtration, washed with 2:1 EtOH/Et$_2$O, and dried under reduced pressure giving a white solid (60.6 g).

The structure and absolute stereochemistry of 23 were confirmed by single-crystal x-ray diffraction analysis. Single crystal diffraction data was acquired on a Bruker Apex II diffractometer equipped with sealed tube Cu K-alpha source (Cu Kα radiation, y=1.54178 Å) and an Apex II CCD detector. A crystal with dimensions of 0.15×0.15×0.10 mm was selected, cleaned using mineral oil, mounted on a Micro-Mount and centered on a Bruker APEXII system. Three batches of 40 frames separated in reciprocal space were obtained to provide an orientation matrix and initial cell parameters. Final cell parameters were obtained and refined after data collection was completed based on the full data set. Based on systematic absences and intensities statistics the structure was solved and refined in acentric P2$_1$ space group.

A diffraction data set of reciprocal space was obtained to a resolution of 0.85 Å using 0.5° steps using 30 s exposures for each frame. Data were collected at 100 (2) K. Integration of intensities and refinement of cell parameters were accomplished using APEXII software. Observation of the crystal after data collection showed no signs of decomposition. As shown in FIG. 2, there are two symmetry independent molecules in the structure and both symmetry independent molecules are R isomers.

The data was collected, refined and reduced using the Apex II software. The structure was solved using the SHELXS97 (Sheldrick, 1990); program(s) and the structure refined using the SHELXL97 (Sheldrick, 1997) program. The crystal shows monoclinic cell with P2$_1$ space group. The lattice parameters are a=9.9016(2) Å, b=10.9184(2) Å, c=19.2975 (4) Å, β=102.826(1)°. Volume=2034.19(7) Å$^3$.

Example 1.j

Preparation of the methanesulfonic acid salt 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (24)

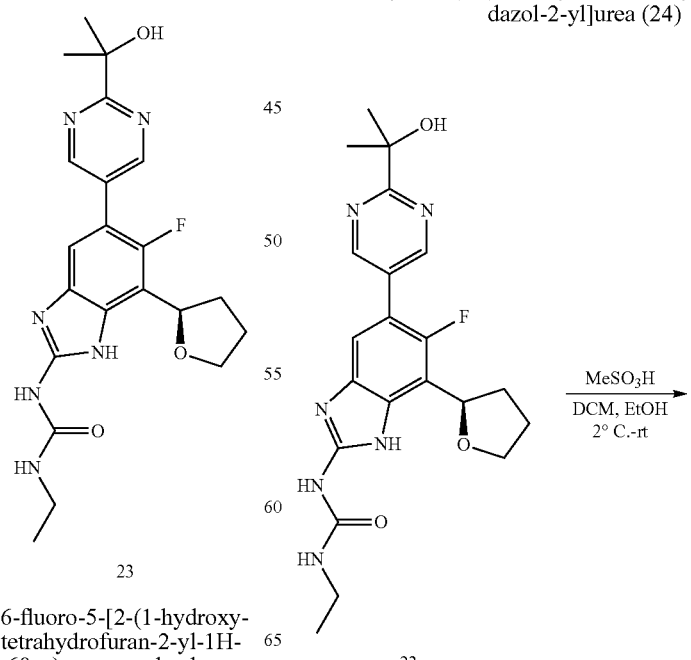

-continued

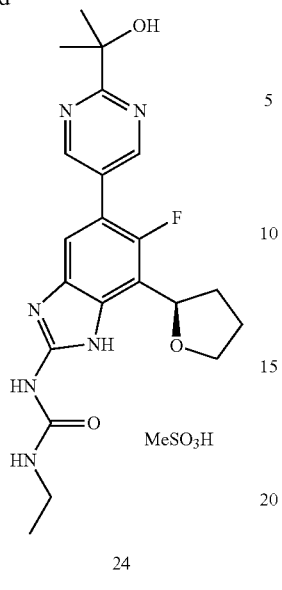

24

To a stirring suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (15.05 g, 35.13 mmol) in dichloromethane (60 mL, J. T. Baker 931533) and absolute ethanol (15 mL, Pharmco-AAPER 111000200) was added methanesulfonic acid (2.392 mL, 36.89 mmol, Sigma-Aldrich 471356). Stirred at room temperature until a clear solution was observed. Added heptane (300 mL) slowly over about 1 hr and collected the solid precipitate by filtration (using a Whatman qualitative #3 paper on top of a Whatman GF/F glass microfibre paper). Dried under reduced pressure in a vacuum oven (desiccated with calcium sulfate and potassium hydroxide) overnight at 40° C. giving 24 as a white solid (13.46 g, 99+% HPLC purity, 99+% ee). Analytical chiral HPLC shows one enantiomer with retention time of 8.6 min eluting with $CH_2Cl_2$/MeOH/TEA (60/40/0.1) on a CHIRALPAK® IC® 4.6×250 mm column with 1 mL/min flow rate at 30° C. A second crop of white solid product 24 (4.36 g, 98% HPLC purity, 99+% ee) was obtained from the filtrate. LCMS (C18 column eluting with 10-90% $CH_3CN$/water gradient over 5 minutes with formic acid modifier) M+1: 429.58 (2.03 min). $^1$H NMR (300 MHz, MeOD) δ 9.00 (d, J=1.6 Hz, 2H), 7.67 (d, J=6.1 Hz, 1H), 5.39 (t, J=7.7 Hz, 1H), 4.30 (dd, J=14.9, 6.9 Hz, 1H), 4.03 (dd, J=14.8, 7.7 Hz, 1H), 3.40-3.31 (m, 2H), 2.72 (s, 3H), 2.70-2.60 (m, 1H), 2.21-2.08 (m, 2H), 1.98-1.84 (m, 1H), 1.65 (s, 6H), 1.22 (t, J=7.2 Hz, 3H) ppm.

Example 1.k

Preparation of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea To a solution of 2-[5-(4,5-diamino-2-fluoro-3-tetrahydrofuran-2-yl-phenyl)pyrimidin-2-yl]propan-2-ol (7.220 g, 21.72 mmol) and 1-ethyl-3-(N-(ethylcarbamoyl)-C-methyl-sulfanyl-carbonimidoyl)urea (6.054 g, 26.06 mmol, CB Research and Development) in 1,4-dioxane (36.1 mL, Sigma-Aldrich 360481) was added a pH 3.5 buffer (72.2 mL), prepared by dissolving NaOAc trihydrate (5.32 g) in 1N aqueous $H_2SO_4$ (37 mL). The reaction mixture was stirred at reflux overnight (HPLC showed complete conversion), cooled to room temperature, and poured portion-wise (frothing) into a stirring solution of aqueous saturated $NaHCO_3$ (144 mL) giving pH 8-9. This was stirred for 20 minutes, the solid was collected by filtration, washed copiously with water to neutral pH, and then more sparingly with EtOH. The solid was dried under reduced pressure giving a beige solid (7.90 g, 99% HPLC purity). LCMS (C18 column eluting with 10-90% $CH_3CN$/water gradient over 5 minutes with formic acid modifier) M+1: 429.45 (2.03 min). HPLC retention time was 3.89 min (YMC ODS-AQ 150×3.0 mm column eluting with 10-90% $CH_3CN$/water gradient over 8 minutes with 0.1% TFA modifier and 1 mL/min flow rate).

Preparation of Form I

Example 1.l

Chiral chromatographic isolation of (R)-1-ethyl-3-[6-fluoro-5-[2-(1-hydroxy-1-methyl-ethyl)pyrimidin-5-yl]-7-(tetrahydrofuran-2-yl)-1H-benzimidazol-2-yl]urea A racemic sample of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (133.60 g) was resolved on a CHIRALPAK® IC® column (by Chiral Technologies) eluting with DCM/MeOH/TEA (60/40/0.1) at 25° C. giving the desired enantiomer as an off-white solid (66.8 g, 99.8% HPLC purity, 99+% ee). Analytical chiral HPLC retention time was 7.7 min (CHIRALPAK® IC® 4.6×250 mm column, 1 mL/min flow rate, 30° C.). The solid was suspended in 2:1 EtOH/Et$_2$O (5 volumes), stirred for 10 minutes, collected by filtration, washed with 2:1 EtOH/Et$_2$O, and dried under reduced pressure giving a white solid (60.6 g). $^1$H NMR (300 MHz, MeOD) δ 8.95 (d, J=1.6 Hz, 2H), 7.45 (d, J=6.5 Hz, 1H), 5.38 (br.s, 1H), 4.27 (dd, J=14.9, 7.1 Hz, 1H), 4.01 (dd, J=15.1, 7.0 Hz, 1H), 3.37-3.29 (m, 2H), 2.55 (br.s, 1H), 2.19-2.07 (m, 2H), 2.02-1.82 (br.s, 1H), 1.63 (s, 6H), 1.21 (t, J=7.2 Hz, 3H) ppm.

Preparation of Form II

Example 1.m

To 100 mg of the 6-fluoro benzimidazolyl urea compound I ml of THF was added. A stoichiometric amount of HCl was added as a 12M aqueous solution. Then 4 mL of MTBE was added and the suspension was allowed to equilibrate overnight with stirring at room temperature. It was then filtered, and the white solid was dried under vacuum for several hours.

Preparation of Form III

Example 1.n 100 mg of 6-fluoro benzimidazolyl urea compound was weighed out and dissolved in 200 mL dichloromethane/methanol 1:1 (v:v) mixture. This solution was spray dried on the Buchi B-90 Nano spray dryer (pump program 2) with a condenser attached at spray rates of 100%. Inlet temperature of 101° C. was used with a nitrogen flow of 10 L/min, a nitrogen maximum pressure of 10 psi and a maximum $CO_2$ pressure of 15 psi. 55 mg of white powder was recovered.

Spray drying was performed on the Buchi B-90 Nano spray dryer with a condenser attached. A solution of the 6-fluoro benzimidazolyl urea compound was prepared in a solvent system comprised of $CH_2Cl_2$:Methanol (1:1) and sprayed according to the parameters listed below.

Preparation of Form IV

Example 1.0

Preparation of the methanesulfonic acid salt (R)-1-ethyl-3-[6-fluoro-5-[2-(1-hydroxy-1-methyl-ethyl) pyrimidin-5-yl]-7-(tetrahydrofuran-2-yl)-1H-benzimidazol-2-yl]urea A stirring suspension of (R)-1-ethyl-3-[6-fluoro-5-[2-(1-hydroxy-1-methyl-ethyl)pyrimidin-5-yl]-7-(tetrahydrofuran-2-yl)-1H-benzimidazol-2-yl]urea (2.530 g, 5.905 mmol) in dichloromethane (22.8 mL, Sigma-Aldrich 270997) and absolute ethanol (2.5 mL) was cooled with an ice-water bath. Methanesulfonic acid (0.402 mL, 6.20 mmol, Sigma-Aldrich 471356) was added, removed the cold bath, and stirred at room temperature for 10 minutes. The mixture was concentrated on a rotary evaporator at 30° C. to a thick oil, then added slowly to stirring $Et_2O$, and rinsed the residual product with $CH_2Cl_2$ into the ether. The gummy precipitate was stirred until it broke up into a pasty solid, which was collected by filtration, washed with $Et_2O$, and dried under reduced pressure giving an off-white solid (2.85 g, 99% HPLC purity, 99+% ee). LCMS (C18 column eluting with 10-90% $CH_3CN$/water gradient over 5 minutes with formic acid modifier) M+1: 429.51 (2.49 min). HPLC retention time was 3.86 min (YMC ODS-AQ 150×3.0 mm column eluting with 10-90% $CH_3CN$/water gradient over 8 minutes with 0.1% TFA modifier and 1 mL/min flow rate). Analytical chiral HPLC shows one enantiomer with retention time of 7.8 min eluting with DCM/MeOH/TEA (60/40/0.1) on a CHIRALPAK® IC® 4.6×250 mm column with 1 mL/min flow rate at 30° C. $^1$H NMR (300 MHz, MeOD) δ 8.99 (d, J=1.6 Hz, 2H), 7.67 (d, J=6.1 Hz, 1H), 5.38 (t, J=7.7 Hz, 1H), 4.30 (dd, J=15.0, 6.9 Hz, 1H), 4.02 (dd, J=14.8, 7.6 Hz, 1H), 3.38-3.30 (m, 2H), 2.73 (s, 3H), 2.70-2.60 (m, 1H), 2.20-2.07 (m, 2H), 1.99-1.84 (m, 1H), 1.64 (s, 6H), 1.22 (t, J=7.2 Hz, 3H) ppm.

Example 1.p

Stability Data

The mesylate salt of the 6-fluorobenzimidazolyl urea compound was found to be chemically and physically unstable at 25° C./60% RH at the one week time point, and chemically unstable at t=2 weeks when stored at 40° C./ambient.

The free base 6-fluoro benzimidazolyl urea compound was chemically and physically stable under all storage conditions (25° C./60% RH, 40° C./ambient, and 40° C./75% RH) at the 1 month timepoint. Small changes were observed in the XRPD pattern, but all were considered to be the same form as at time zero (t=0).

The hydrochloride salt of the 6-fluoro benzimidazolyl urea compound was chemically and physically stable under all storage conditions (25° C./60% RH, 40° C./ambient, and 40° C./75% RH) at the 1 month timepoint.

Example 2

Enzymology Studies

The enzyme inhibition activities of compounds of this invention may be determined in the experiments described below:

DNA Gyrase ATPase Assay

The ATP hydrolysis activity of S. aureus DNA gyrase is measured by coupling the production of ADP through pyruvate kinase/lactate dehydrogenase to the oxidation of NADH. This method has been described previously (Tamura and Gellert, 1990, J. Biol. Chem., 265, 21342).

ATPase assays are carried out at 30° C. in buffered solutions containing 100 mM TRIS pH 7.6, 1.5 mM $MgCl_2$, 150 mM KCl. The coupling system contains final concentrations of 2.5 mM phosphoenol pyruvate, 200 μM nicotinamide adenine dinucleotide (NADH), 1 mM DTT, 30 ug/ml pyruvate kinase, and 10 ug/ml lactate dehydrogenase. The enzyme (90 nM final concentration) and a DMSO solution (3% final concentration) of a compound is added. The reaction mixture is allowed to incubate for 10 minutes at 30° C. The reaction is initiated by the addition of ATP to a final concentration of 0.9 mM, and the rate of NADH disappearance is monitored at 340 nanometers over the course of 10 minutes. The $K_i$ and $IC_{50}$ values are determined from rate versus concentration profiles.

TABLE 3

| Inhibition of S. aureus DNA Gyrase | |
|---|---|
| Selected Compound | $K_i$ (nM) |
| Compound 23* | 9 |

*Compound 23 may be prepared as in Example 1.i, above.

DNA Topo IV ATPase Assay

The conversion of ATP to ADP by S. aureus TopoIV enzyme is coupled to the conversion of NADH to NAD+, and the progress of the reaction is measured by the change in absorbance at 340 nm. TopoIV (64 nM) is incubated with the selected compound (3% DMSO final) in buffer for 10 minutes at 30° C. The buffer consists of 100 mM Tris 7.5, 1.5 mM $MgCl_2$, 200 mM K•Glutamate, 2.5 mM phosphoenol pyruvate, 0.2 mM NADH, 1 mM DTT, 5 μg/mL linearized DNA, 50 μg/mL BSA, 30 μg/mL pyruvate kinase, and 10 μg/mL lactate dehydrogenase (LDH). The reaction is initiated with ATP, and rates are monitored continuously for 20 minutes at 30° C. on a Molecular Devices SpectraMAX plate reader. The inhibition constant, Ki, and the $IC_{50}$ are determined from plots of rate vs. concentration of selected compound fit to the Morrison Equation for tight binding inhibitors.

TABLE 4

| Inhibition of S. aureus DNA Topo IV | |
|---|---|
| Selected Compound | $K_i$ (nM) |
| Compound 23 | 12 |

Example 3

Susceptibility Testing in Liquid Media

Compounds of this invention were tested for antimicrobial activity by susceptibility testing in liquid media. Such assays can be performed within the guidelines of the latest CLSI document governing such practices: "M07-A8 Methods for Dilution Antimicrobial Susceptibility Tests for Bacteria that Grow Aerobically; Approved Standard—Eighth Edition (2009)". Other publications such as "Antibiotics in Laboratory Medicine" (Edited by V. Lorian, Publishers Williams and Wilkins, 1996) provide essential practical techniques in laboratory antibiotic testing. The specific protocols used were as follows:

Protocol #1: Gyrase MIC Determination of Compounds Using Microdilution Broth Method Materials:
Round bottom 96-well microtiter plates (Costar 3788)
Mueller Hinton II agar plates (MHII; BBL premix)
Mueller Hinton II liquid broth (MHII; BBL premix)
BBL Prompt Inoculation System (Fisher B26306)
Test Reading Mirror (Fisher)
Agar plates with bacteria streaked to single colonies, freshly prepared
Sterile DMSO
Human serum (U.S. Biologicals S1010-51)
Laked horse blood (Quad Five 270-100)
Resazurin 0.01%
Sprague Dawley Rat serum (U.S. Biologicals 1011-90B or Valley BioMedical AS3061SD)
Pooled Mouse serum (Valley BioMedical AS3054)

Strains (Media, Broth and Agar):
1. *Staphylococcus aureus* ATCC #29213
   a. MHII
   b. MHII+50% human serum
   c. MHII+50% rat serum
   d. MHII+50% mouse serum
2. *Staphylococcus aureus* ATCC #29213 GyrB T173I (MHII)
3. *Staphylococcus aureus*, JMI collection strains; see table 9 (MHII)
4. *Staphylococcus epidermidis*, JMI collection strains; see table 9 (MHII)
5. *Enterococcus faecalis* ATCC #29212 (MHII+3% laked horse blood)
6. *Enterococcus faecium* ATCC #49624 (MHII+3% laked horse blood)
7. *Enterocous faecalis*, JMI collection strains; see table 9 (MHII+3% laked horse blood)
8. *Enterocous faecium*, JMI collection strains; see table 9 (MHII+3% laked horse blood)
9. *Streptococcus pneumoniae* ATCC #10015 (MHII+3% laked horse blood)
10. *Streptococcus pneumoniae*, JMI collection strains; see table 9 (MHII+3% laked horse blood)
11. β-haemolytic streptococci, Groups A, B, C, G) JMI collection strains; see table 9 (MHII+3% laked horse blood)
12. *Bacillus cereus* ATCC 10987 (MHII)
13. *Bacillus cereus* ATCC 14579 (MHII)
14. *Bacillus subtilis* ATCC 6638 (MHII)
15. *Bacillus subtilis* (168) ATCC 6051 (MHII)

Inoculum Prep (for all Strains Other than *S. aureus*+50% Sera):
1. Using the BBL Prompt kit, picked 5 big or 10 small, well separated colonies from culture grown on the appropriate agar medium as indicated above and inoculated 1 mL of sterile saline provided in the kit.
2. Vortexed the wells for ~30 s to provide a suspension of ~$10^8$ cells/mL. Actual density could be confirmed by plating out dilutions of this suspension.
3. Diluted the suspension 1/100 by transferring 0.15 mL of cells into 15 mL (~$10^6$ cells/mL) sterile broth (or see below) for each plate of compounds tested, then swirled to mix. If more than 1 plate of compounds (>8 compounds), including compound 23 or 24, were tested, volumes were increased accordingly.
   a. For *E. faecalis, E. faecium* and *S. pneumoniae*: 14.1 mL MHII+0.9 mL laked horse blood was used.
4. Used 50 μl cells (~$5 \times 10^4$ cells) to inoculate each microtiter well containing 50 μl of the drug diluted in broth (see below).

Drug Dilutions, Inoculation, MIC Determination:
1. All drug/compound stocks were prepared at 12.8 mg/mL concentration, usually in 100% DMSO.
2. Diluted drug/compound stocks to 200× desired final concentration in 50 μL DMSO. If starting concentration of MICs was 8 μg/mL final concentration, then required 6.25 μL of stock+43.75 μA DMSO. Each 200× stock was placed in a separate row of column 1 of a new 96 well microtiter plate.
3. Added 25 μL of DMSO to columns 2-12 of all rows of the microtiter plate containing 200× compound stocks and serially diluted 25 μL from column 1 through column 11, changed tips after each column. i.e. 25 μA compound+25 μA DMSO=2× dilution. Left "no compound" DMSO well at the end of the series for control.
4. For each strain tested (except *S. aureus*+50% human serum), prepared two microtiter plates with 50 μA of MHII broth using a Matrix pipettor.
5. Transferred 0.5 μL of each dilution (w/Matrix autopipettor) to 50 μL of medium/microtiter well prior to the addition of 50 μl of cells. The usual starting concentration of compound was 8 μg/mL after the 1/200 dilution into medium+cells−compound concentrations decreased in 2× steps across the rows of the microtiter plate. All MICs were done in duplicate.
6. All wells were inoculated with 50 μl of diluted cell suspension (see above) to a final volume of 100 μl.
7. After inoculum was added, mixed each well thoroughly with a manual multichannel pipettor; same tips were used going from low to high concentration of drug in the same microtiter plate.
8. Plates were incubated at 37° C. for at least 18 hours.
9. Plates were viewed with a test reading mirror after 18 hours and the MIC was recorded as the lowest concentration of drug where no growth was observed (optical clarity in the well).

Preparation of *S. aureus*+50% Human Serum, *S. aureus*+50% Rat Serum or *S. aureus*+50% Mouse Serum.
1. Prepared 50% serum media by combining 15 mL of MHII+15 mL human serum—total 30 mL. Increased volume in 30 mL increments when more than 1 compound plate was tested.
2. Used the same BBL Prompt inoculum of *S. aureus* ATCC #29213 as described above, diluted 1/200 by transferring 0.15 mL of cells into 30 mL (~$5 \times 10^5$ cells/mL) of the 50% human serum media prepared above and swirled to mix.
3. Filled all test wells of the desired number of microtiter plates with 100 μL cells in 50% serum media.
4. Transferred 0.5 μL of each compound dilution (w/Matrix auto-pipettor) to 100 μL of cells/media. The usual starting concentration of compound was 8 μg/mL after the 1/200 dilution into medium+cells−compound concentrations decreased in 2× steps across the rows of a microtiter plate. All MICs were done in duplicate.
5. Mixed each well thoroughly with a manual multichannel pipettor; same tips were used going from low to high concentration of drug in the same microtiter plate.

6. Plates were incubated at 37° C. for at least 18 hours. After incubation, added 25 μL of 0.01% Resazurin to each well and continued to incubate at 37° C. for at least 1 additional hour or until the Resazurin color changes.
7. Plates were viewed with a test reading mirror and the MIC was recorded. When using Resazurin, the color of the dye changed from a dark blue to a bright pink in wells with no growth. The lowest concentration of drug that turned the dye pink was the MIC.

Protocol 2: Gyrase MIC Determination of Compounds Against Gram Negatives Using Microdilution Broth Method
Materials:
Round bottom 96-well microtiter plates (Costar 3788)
Mueller Hinton II agar plates (MHII; BBL premix)
Mueller Hinton II liquid broth (MHII; BBL premix)
BBL Prompt Inoculation System (Fisher b26306)
Test Reading Mirror (Fisher)
Agar plates with bacteria streaked to single colonies, freshly prepared
Sterile DMSO
Strains (MHII Media for all; Broth and Agar):
1. *Escherichia coli* ATCC #25922
2. *Escherichia coli*, JMI collection strains, see table 9
3. *Escherichia coli* AG100 WT
4. *Escherichia coli* AG100 tolC
5. *Acinetobacter baumannii* ATCC # BAA-1710
6. *Acinetobacter baumannii* ATCC #19606
7. *Acinetobacter baumannii*, JMI collection strains, see table 9
8. *Klebsiella pneumoniae* ATCC # BAA-1705
9. *Klebsiella pneumoniae* ATCC #700603
10. *Klebsiella pneumoniae*, JMI collection strains, see table 9
11. *Moraxella catarrhalis* ATCC#25238
12. *Moraxella catarrhalis* ATCC#49143
13. *Moraxella catarrhalis*, JMI collection strains, see table 9
14. *Haemophilus influenzae* ATCC 49247
15. *Haemophilus influenzae* (Rd1 KW20) ATCC 51907
16. *Haemophilus influenzae* Rd0894 (AcrA-)
17. *Haemophilus influenzae*, JMI collection strains, see table 9
18. *Pseudomonas aeruginosa* PAO1
19. *Pseudomonas aeruginosa*, JMI collection strains, see table 9
20. *Proteus mirabilis*, JMI collection strains, see table 9
21. *Enterobacter cloacae*, JMI collection strains, see table 9
22. *Stenotrophomonas maltophilia* ATCC BAA-84
*Stenotrophomonas maltophilia* ATCC13637

Inoculum Prep:
1. Using the BBL Prompt kit, picked 5 big or 10 small, well separated colonies from cultures grown on agar medium and inoculated 1 mL sterile saline that came with the kit.
2. Vortexed the wells for ~30 s to give a suspension of ~$10^8$ cells/mL. Actual density could be confirmed by plating out dilutions of this suspension.
3. Diluted the suspension 1/100 by transferring 0.15 mL of cells into 15 mL (~$10^6$ cells/mL) sterile broth (see below) for each plate of compounds tested, swirled to mix. If more than 1 plate of compounds (>8 compounds), including compound 23 or 24, was to be tested, increased volumes accordingly.
4. Used 50 μl cells (~$5 \times 10^4$ cells) to inoculate each microtiter well containing 50 μl of the drug diluted in broth (see below).

Drug Dilutions, Inoculation, MIC Determination:
1. All drug/compound stocks were prepared at 12.8 mg/mL concentration, usually in 100% DMSO.
2. Diluted drug/compound stocks to 200× desired final concentration in 50 μL DMSO. If starting concentration of MICs was 8 μg/mL final concentration, then required 6.25 μl of stock+43.75 μL DMSO. Each 200× stock was placed in a separate row of column 1 of a new 96 well microtiter plate.
3. Added 25 μL of DMSO to columns 2-12 of all rows of the microtiter plate containing 200× compound stocks and serially diluted 25 μL from column 1 through column 11, changed tips after each column. i.e. 25 μL compound+25 μL DMSO=2× dilution. Left "no compound" DMSO well at the end of the series for control.
4. For each strain tested, prepared two microtiter plates with 50 μL of MHII broth using a Matrix pipettor.
5. Transferred 0.5 μL of each dilution (w/Matrix autopipettor) to 50 μL of medium/microtiter well prior to the addition of 50 μl of cells. The usual starting concentration of compound was 8 μg/mL after the 1/200 dilution into medium+cells–compound concentrations decreased in 2× steps across the rows of a microtiter plate. All MICs were done in duplicate.
6. All wells were inoculated with 50 μl of diluted cell suspension (see above) to a final volume of 100
7. After inoculum was added, each well was mixed thoroughly with a manual multichannel pipettor; same tips were used going from low to high concentration of drug in the same microtiter plate.
8. Plates were incubated at 37° C. for at least 18 hours.
9. Plates were viewed with a test reading mirror after 18 hours and the MIC was recorded as the lowest concentration of drug where no growth was observed (optical clarity in the well).

Protocol #3: Gyrase MIC Determination of Compounds Using Agar Dilution Method
Materials:
Petri plates 60×15 mm (Thermo Scientific Cat. #12567100)
Centrifuge tubes, 15 mL (Costar)
BBL Prompt Inoculation System (Fisher b26306)
Agar plates with bacteria streaked to single colonies, freshly prepared Sterile DMSO
GasPak™ incubation containers (BD Cat. #260672)
GasPak™ EZ Anaerobe container system sachets (BD Cat. #260678)
GasPak™ EZ C02 container system sachets (BD Cat. #260679)
GasPak™ EZ Campy container system sachets (BD Cat. #260680)
Strains:
1. *Clostridium difficile* ATCC BAA-1382;
2. *Clostridium difficile*, CMI collection strains, see table 8
3. *Clostriudium perfringens*, CMI collection strains, see table 8
4. *Bacteroides fragilis* and *Bacteroides* spp., CMI collection strains, see table 8
5. *Fusobacterium* spp., CMI collection strains, see table 8
6. *Peptostreptococcus*, spp., CMI collections strains, see table 8
7. *Prevotella* spp., CMI collection strains, see table 8
8. *N. gonorhoeae* ATCC 35541
9. *N. gonorhoeae* ATCC 49226
10. *Neisseria gonorrhoeae*, JMI collection strains, see table 8
11. *Neisseria meningitidis*, JMI collection strains, see table 8

Media Preparation and Growth Conditions:

Growth medium recommended for each microbial species was prepared according to the CLSI publication 'M11-A7 Methods for Antimicrobial Susceptibility Testing of Anaerobic Bacteria; Approved Standard—Seventh Edition (2007)' with the exception of *N. gonorrhoeae* and *N. meningitidis* for which media was prepared according to "M07-A8 Methods for Dilution Antimicrobial Susceptibility Tests for Bacteria that Grow Aerobically; Approved Standard—Eighth Edition (2009)".

Plate Pouring:
1. Prepared 100× drug stocks of each test compound as described in Table 1. Used a 15 mL centrifuge tube, added 100 uL of each drug stock to 10 mL of molten agar (cooled to ~55° C. in water bath). Mixed by inverting tube 2-3× then pour into individually labeled 60×15 mm Petri dish.
2. Routine test concentrations were: 0.002 ug/mL-16 ug/mL (14 plates).
3. Poured 4 drug free plates: 2 as positive control, 2 as aerobic control.
4. Allowed plates to dry. Used same day or stored overnight at RT or stored up to 3 days at 4° C.

Plates were labeled accordingly for drug concentration and strain placement.

Growth of Cells Requiring the Maintenance of an Anaerobic Environment:
1. All work performed with anaerobic bacteria was done as rapidly as possible; work performed in biosafety cabinets (i.e., aerobic environment) was completed in less then 30 minutes before cells were returned to anaerobic chambers.
2. Incubation of anaerobic bacteria was achieved using GasPak™ chambers. The large box style chambers (VWR 90003-636) required 2 anaerobic sachets (VWR 90003-642), while the tall cylinder style chambers (VWR 90003-602) only required 1 sachet.

Plate Inoculation (Performed in Biosafety Cabinet):
1. Streaked each strain onto individual agar plates as described above. Incubated for required time and environmental condition (i.e. anaerobic, microaerophilic, etc).
2. Used direct colony suspension method to suspend loopfuls of freshly streaked cells into ~4 mL 0.9% $NaCl_2$ and vortexed.
3. Adjusted suspension to $O.D._{600}$ 0.05 (5×10e7 cfu/mL). Vortexed to mix.
4. Transferred ~0.2 mL of adjusted, mixed cultures to a 96 well plate. When ≦5 strains were tested, all strains were lined together in a single row. When testing >5 strains, transferred strains into plate with no more that 5 strains in a single row. This was necessary to fit on the small plates.
5. Used multi-channel pipettor, spotted 0.002 mL of each strain from prepared 96 well plates onto each MIC test plate. This resulted in ~1×10e5 cfu/spot. When testing *C. difficile*, strains swarmed when grown, however distance between multi-channel pipettor spots was far enough such that swarming cells did not impair assay results.
    a. Inoculated 2 drug free plates first, while the other 2 drug free plates were inoculated last after the MIC test plates. The former and latter served as growth and inoculation controls. Incubated one plate from each set of drug-free controls under required atmospheric conditions with MIC plates and one set aerobically to test for contamination with aerobic bacteria. Aerobic culture was negative for growth when working with strict anaerobe or microaerophilic strain. Some growth was visible with *N. gonorrhoeae*.
6. Allowed inoculum to dry (for as short a time as necessary), then placed upside down in GasPak with appropriate number of sachets and incubate.
7. *Neisseria* spp. were incubated at 37° C. in a 5% $CO_2$ environment for 24 h.

MIC Determination:

Examined the test plates after the correct incubation time and read the MIC endpoint at the concentration where a marked reduction occurred in the appearance of growth on the test plate as compared to that of growth on the positive control plates.

TABLE 5

Compound dilutions for MIC determination using the agar dilution method.

| Step | Stock (ug/ml) | Source | Volume from stock (uL) | Diluent, DMSO (uL)** | Intermediate Conc. (ug/mL) | Final Conc. At 1:100 (ug/mL) | Volume (uL) added to 10 mL agar |
|---|---|---|---|---|---|---|---|
| 1 | 1,600* | Stock | | | 1,600 | 16 | 100 |
| 2 | 1,600 | Stock | 75 | 75 | 800 | 8 | 100 |
| 3 | 1,600 | Stock | 75 | 225 | 400 | 4 | 100 |
| 4 | 1,600 | Stock | 75 | 525 | 200 | 2 | 100 |
| 5 | 200 | Step 4 | 75 | 75 | 100 | 1 | 100 |
| 6 | 200 | Step 4 | 75 | 225 | 50 | 0.5 | 100 |
| 7 | 200 | Step 4 | 75 | 525 | 25 | 0.25 | 100 |
| 8 | 25 | Step 7 | 75 | 75 | 12.5 | 0.125 | 100 |
| 9 | 25 | Step 7 | 75 | 225 | 6.25 | 0.06 | 100 |
| 10 | 25 | Step 7 | 75 | 525 | 3.1 | 0.03 | 100 |
| 11 | 3 | Step 10 | 75 | 75 | 1.6 | 0.016 | 100 |
| 12 | 3 | Step 10 | 75 | 225 | 0.8 | 0.008 | 100 |
| 13 | 3 | Step 10 | 75 | 525 | 0.4 | 0.004 | 100 |
| 14 | 0.4 | Step 13 | 75 | 75 | 0.2 | 0.002 | 100 |

*1,600 ug/ml = 64 ul (10 mg/ml stock) + 336 ul DMSO; 400 ul total volume to start
**compound dissolved and diluted in 100% DMSO Protocol #4. MIC Determination Procedure for *Mycobacterium* Species Materials Round bottom 96-well microtiter plates (Costar 3788) or similar Film plate seals (PerkinElmer, TopSeal-A #6005250 or similar)

Middlebrook 7H10 broth with 0.2% glycerol

Middlebrook 7H10 agar with 0.2% glycerol

Middlebrook OADC Enrichment

Inoculum Preparation for *M. tuberculosis*:
1. Used prepared frozen *M. tuberculosis* stock stored at −70° C. *M. tuberculosis* was grown in 7H10 broth+10% OADC, then frozen at a concentration of 100 Klett or $5 \times 10^7$ cfu/ml,
2. Prepared a 1:20 dilution by removal of 1 ml of the frozen stock and added it to 19 ml of 7H10 broth+10% OADC (final concentration $2.5 \times 10^6$ cfu/ml).
3. From this dilution prepared a second 1:20 dilution, removed 1 ml and added it to 19 ml of fresh broth. This was the final inoculum to add to the 96-well plates.

Inoculum Preparation for *M. kansasii, M. avium, M. abscessus* and *Nocardia* Spc.:
1. Used prepared frozen stock of culture or a fresh culture grown in 7H10 broth at a concentration of 10 Klett or $5 \times 10^7$/ml.
2. Prepared a 1:20 dilution by removing 1.0 ml of the culture stock and added it to 19 ml of 7H10 broth (final concentration $2.5 \times 10^6$ cfu/ml).
3. From this dilution prepared a 1:20 dilution, removed 1 ml and added it to 19 ml of fresh broth (final suspension).

Plate Preparation:
1. Labeled plates.
2. Added 50 µl of 7H10 broth+10% OADC to all wells being utilized for MIC determination using a multichannel electronic pipettor.
3. Prepared stock solutions of drugs (e.g. 1 mg/ml concentration) to be tested.
4. Thawed and diluted frozen stock solutions using 7H10 broth+10% OADC to obtain a working solution 4× the maximum concentration tested (e.g. final concentration 32 µg/ml, highest concentration tested was 8 µg/ml). Dilutions were made from the stock solution. To start at a concentration of 1 µg/ml, the drugs were prepared at 4 µg/ml, so the starting concentration was 1 µg/ml. Removed 25 µl of the 1 mg/ml stock and added to 6.2 ml of broth. All dilutions of drugs were done in broth.
5. Added 50 µl of the 4× working solution to the first well of the designated row. Continued for all compounds to be tested. Using a multichannel electronic pipettor, mixed 4× and serial diluted compounds through the 11th well. Discarded remaining 50 µl. Used the 12th well as the positive control.
6. Incubated plates at 37° C. *M. tuberculosis* for ~18 days; *M. avium* and *M. kansasii* for ~7 days; *Nocardia* and *M. abcessus* for ~4 days; with film seals.
7. Read visually and recorded the results. The MIC was recorded as the lowest concentration of drug where no growth was observed (optical clarity in the well).

Protocol #5. Protocol for *Mycobacterium tuberculosis* Serum Shift MIC Assay

Materials and Reagents:

Costar #3904 Black-sided, flat-bottom 96-well microtiter plates

Middlebrook 7H9 broth (BD271310) with 0.2% glycerol

Middlebrook OADC Enrichment

Fetal Bovine Serum

Catalase (Sigma C1345)

Dextrose $NaCl_2$

BBL Prompt Inoculation System (Fisher b26306)

Agar plates (Middlebrook 7H11 with 0.2% glycerol and OADC enrichment) with bacteria streaked to single colonies Sterile DMSO Media Prep:
1. For serum shifted MICs, three different media were required which all had a base of 7H9+0.2% glycerol. It was important that all media and supplements were sterilized prior to MICs.
2. Prepared all media below and inoculated as described in next section. Tested all compounds against Mtb using each media.
   a. 7H9+0.2% glycerol+10% OADC ("standard" MIC media).
   b. 7H9+0.2% glycerol+2 g/L dextrose+0.85 g/L NaCl+ 0.003 g/L catalase (0% FBS).
   c. 2×7H9+0.2% glycerol+2 g/L dextrose+0.85 g/L NaCl+0.003 g/L catalase combined with equal volume Fetal Bovine Serum (50% FBS).

Inoculum prep:
1. Using BBL Prompt, picked 5-10 well-separated colonies and inoculated 1 ml sterile saline that came in the kit. Typically plates were two to three weeks of age when used for this assay due to the slow growth of this organism in culture.
2. Vortexed well, then sonicated in water bath for 30 sec providing a suspension of ~$10^8$ cells/ml. Actual density could be confirmed by plating out dilutions of this suspension.
3. Prepared inoculum in each of the three media formulations by diluting the BBL Prompt suspension 1/200 (for example: transferred 0.2 ml of cells to 40 ml of medium) to obtain a starting cell density of ~$10^6$ cells/ml.
4. Used 100 µl cells (~$5 \times 10^4$ cells) to inoculate each microtiter well containing 1 µl of drug in DMSO (see below).

Drug Dilutions, Inoculation, MIC Determination:
1. Control drug stocks Isoniazid and Novobiocin were prepared at 10 mM in 100% DMSO while Ciprofloxacin and Rifampin were prepared at 1 mM in 50% DMSO and 100% DMSO, respectively. Prepared dilutions—dispensed 100 µL of the stock solution into the first column of a 96-well plate. Prepared 11-step, 2-fold serial dilutions across the row for each compound by transferring 50 µl from column 1 into 50 µl of DMSO in column 2. Continued to transfer 50 µL from column 2 through column 11 while mixing and changing tips at each column. Left column 12 with DMSO only as a control.
2. Transferred 1 µl of each dilution into an empty microtiter well prior to the addition of 100 µl of cells. The starting concentration of Isoniazid and Novobiocin was 100 µM after the dilution into medium+ cells; the starting concentration of Ciprofloxacin and Rifampin was 10 µM after the dilution into medium+ cells. Compound concentrations decreased in 2× steps moving across the rows of the microtiter plate. All MICs were done in duplicate at each of the three medium conditions.
3. Test sets of compounds were typically at 10 mM and 50 µL volume.
4. Used a multichannel pipettor, removed all of the volume from each column of the master plate and transferred into the first column of a new 96-well microtiter plate. Repeated for each column of compounds on master plate, transferring into column 1 of a new 96-well plate.

5. As described above for control compounds, generated 2-fold, 11-point dilutions of each compound using DMSO as diluent. In all cases, left column 12 as DMSO only for a control. Once all dilutions were complete, again transferred 1 μl of each dilution into an empty microtiter well prior to the addition of 100 μl of cells as done for the control compounds.
6. All wells were inoculated with 100 μl of diluted cell suspension (see above).
7. After inoculum addition, mixed plates by gently tapping sides of plate.
8. Plates were incubated in a humidified 37° C. chamber for 9 days.
9. At 9 days added 25 μl 0.01% sterile resazurin to each well. Measured background fluorescence at Excitation 492 nm, Emission 595 nm and returned the plate to the incubator for another 24 hours.
10. After 24 hours the fluorescence of each well was measured at Excitation 492 nm, Emission 595 nm.
11. Percent inhibition by a given compound was calculated as follows: Percent inhibition=100−([well fluorescence−average background fluorescence]/[DMSO control−average background fluorescence]×100). MICs were scored for all three medium conditions as the lowest compound concentration that inhibited resazurin reduction ('%-inhibition') signal 70% at a given medium condition.

Table 6 shows the results of the MIC assay for the mesylate salt of the benzimidazolyl urea compound of this invention. In Table 6 and in subsequent Tables and Examples, "Compound 24" is a mesylate salt of "Compound 23" and may be prepared according to Example 1.j, above. This is the same number used to identify said compound as used in the Examples above.

TABLE 6

MIC Values of Compound 24

| Strain/Special Condition | Protocol | Compound 24 |
|---|---|---|
| *Staphylococcus aureus* ATCC 29213 | 1 | 0.021 |
| *Staphylococcus aureus* ATCC 29213 with Human Serum | 1 | 0.15 |
| *Staphylococcus aureus* ATCC 29213 with Rat Serum | 1 | 0.18 |
| *Staphylococcus aureus* ATCC 29213 with Mouse Serum | 1 | 0.5 |
| *Staphylococcus aureus* ATCC 29213 GyrB T173I | 1 | 0.3 |
| *Enterococcus faecalis* ATCC 29212, with Laked Horse Blood | 1 | 0.028 |
| *Enterococcus faecium* ATCC 49624 with Laked Horse Blood | 1 | 0.11 |
| *Enterococcus faecium* ATCC 49624 | 1 | 0.11 |
| *Streptococcus pneumoniae* ATCC 10015, with Laked Horse Blood | 1 | 0.01 |
| *Bacillus cereus* ATCC 10987 | 1 | 0.031 |
| *Bacillus cereus* ATCC 14579 | 1 | 0.031 |
| *Bacillus subtilis* ATCC 6638 | 1 | 2 |
| *Bacillus subtilis* (168) ATCC 6051 | 1 | 4 |
| *Clostridium difficile* ATCC BAA-1382 | 3 | 0.38 |
| *Haemophilus influenzae* ATCC 49247 | 2 | 0.5 |

TABLE 6-continued

MIC Values of Compound 24

| Strain/Special Condition | Protocol | Compound 24 |
|---|---|---|
| *Haemophilus influenzae* (Rd1 KW20) ATCC 51907 | 2 | 1.3 |
| *Haemophilus influenzae* Rd0894 (AcrA-) | 2 | 0.041 |
| *Moraxella catarrhalis* ATCC 25238 | 2 | ≦0.016 |
| *Moraxella catarrhalis* ATCC 49143 | 2 | ≦0.016 |
| *Neisseria gonorrhoeae* ATCC 35541 | 3 | 0.42 |
| *Neisseria gonorrhoeae* ATCC 49226 | 3 | 1 |
| *Escherichia coli* AG100 WT | 2 | 4 |
| *Escherichia coli* AG100 tolC | 2 | 0.063 |
| *Escherichia coli* ATCC 25922 | 2 | 12 |
| *Escherichia coli* CHE30 | 2 | 8 |
| *Escherichia coli* CHE30 tolC | 2 | 0.125 |
| *Escherichia coli* MC4100 | 2 | >16 |
| *Escherichia coli* MC4100 tolC | 2 | 0.25 |
| *Klebsiella pneumoniae* ATCC 700603 | 2 | 16 |
| *Klebsiella pneumoniae* ATCC BAA-1705 | 2 | 12 |
| *Acinetobacter baumannii* ATCC 19606 | 2 | 8 |
| *Acinetobacter baumannii* ATCC BAA-1710 | 2 | 6 |
| *Pseudomonas aeruginosa* PAO1 | 2 | >16 |
| *Pseudomonas aeruginosa* PAO750 | 2 | 0.25 |
| *Stenotrophomonas maltophilia* ATCC BAA-84 | 2 | >8 |
| *Stenotrophomonas maltophilia* ATCC13637 | 2 | >8 |
| *Mycobacterium avium* 103 | 4 | 0.18 |
| *M. avium* Far | 4 | 0.23 |
| *M. avium* 3404.4 | 4 | 0.23 |
| *Nocardia caviae* 2497 | 4 | 0.125 |
| *N. asteroids* 2039 | 4 | 1 |
| *N. nova* 10 | 4 | 1 |
| *M. kansasii* 303 | 4 | 0.03 |
| *M. kansasii* 316 | 4 | 0.06 |
| *M. kansasii* 379 | 4 | <0.015 |
| *M. tuberculosis* H37Rv ATCC 25618 | 4 | 0.015 |
| *M. tuberculosis* Erdman ATCC 35801 | 4 | 0.06 |
| *M. tuberculosis* Erdman ATCC 35801 | 5 | 0.03 |
| *M. tuberculosis* Erdman ATCC 35801 with Mouse Serum | 5 | 0.5 |
| *M. abscessus* BB2 | 4 | 1 |
| *M. abscessus* MC 6005 | 4 | 1 |
| *M. abscessus* MC 5931 | 4 | 0.5 |
| *M. abscessus* MC 5605 | 4 | 1.5 |
| *M. abscessus* MC 6025 | 4 | 0.75 |
| *M. abscessus* MC 5908 | 4 | 1.5 |
| *M. abscessus* BB3 | 4 | 0.5 |
| *M. abscessus* BB4 | 4 | 2 |
| *M. abscessus* BB5 | 4 | 0.5 |
| *M. abscessus* MC 5922 | 4 | 0.25 |
| *M. abscessus* MC 5960 | 4 | 0.5 |
| *M. abscessus* BB1 | 4 | 2 |
| *M. abscessus* MC 5812 | 4 | 1 |
| *M. abscessus* MC 5901 | 4 | 1 |
| *M. abscessus* BB6 | 4 | 0.5 |
| *M. abscessus* BB8 | 4 | 0.5 |
| *M. abscessus* MC 5908 | 4 | 1 |
| *M. abscessus* LT 949 | 4 | 1 |
| *M. abscessus* BB10 | 4 | 0.015 |
| *M. abscessus* MC 6142 | 4 | 0.5 |

TABLE 6-continued

MIC Values of Compound 24

| Strain/Special Condition | Protocol | Compound 24 |
|---|---|---|
| M. abscessus MC 6136 | 4 | 0.5 |
| M. abscessus MC 6111 | 4 | 0.5 |
| M. abscessus MC 6153 | 4 | 1 |

Table 7 shows the results of the MIC90 assay for selected compounds of this invention.

TABLE 7

MIC90 Values of Selected Compounds with Panels of Gram Positive, Gram Negative and Anaerobic Pathogens

| Organism | Number of Isolates Tested | Protocol | Compound 24 Range (µg/ml) | Compound 24 MIC90 (µg/ml) |
|---|---|---|---|---|
| Aerobic Gram-positive | | | | |
| Staphylococcus aureus | 67 | 1 | 0.008-0.06 | 0.03 |
| Staphlococcus epidermidis | 35 | 1 | 0.008-0.03 | 0.03 |
| Enterococcus faecalis | 34 | 1 | 0.015-0.12 | 0.06 |
| Enterococcus faecium | 33 | 1 | 0.003-0.25 | 0.12 |
| Streptococcus pneumoniae | 67 | 1 | 0.008-0.03 | 0.015 |
| β-haemolytic streptococci (Groups A, B, C and G) | 28 | 1 | 0.015-0.12 | 0.12 |
| Aerobic Gram-negative | | | | |
| Haemophilus influenzae | 55 | 2 | 0.06-2 | 1 |
| Moraxella catarrhalis | 26 | 2 | ≦0.004-0.03 | 0.03 |
| Acinetobacter baumannii | 12 | 2 | 4->8 | >8 |
| Pseudomonas aeruginosa | 12 | 2 | >8->8 | >8 |
| Escherichia coli | 12 | 2 | 2->8 | >8 |
| Klebsiella pneumoniae | 12 | 2 | 2->8 | >8 |
| Proteus mirabilis | 12 | 2 | 4->8 | >8 |
| Enterobacter cloacae | 12 | 2 | >8->8 | >8 |
| Neisseria gonorrhoeae | 13 | 3 | 0.12-0.25 | 0.25 |
| Neisseria meningitidis | 12 | 3 | 0.008-0.06 | 0.03 |
| Anaerobes | | | | |
| Bacteroides and Parabacter spp. | 26 | 3 | 0.12-16 | 16 |
| Bacteroides fragilis | 25 | 3 | 1-16 | 16 |
| Clostridium difficile | 16 | 3 | 0.06-4 | 0.25 |
| Clostridium perfringens | 12 | 3 | 0.12-0.5 | 0.5 |
| Fusobacterium spp. | 16 | 3 | 0.015->16 | >16 |
| Peptostreptococcus spp. | 11 | 3 | 0.03->16 | >16 |
| Prevotella spp. | 13 | 3 | 0.06-16 | 16 |

In Table 8 below, the term "CMI" stands for The Clinical Microbiology
Institute located in Wilsonville, Oreg.

TABLE 8

Panels of Anaerobic Organism Used to Generate MIC90 Data

| CMI# | ORGANISM |
|---|---|
| A2380 | B. fragilis |
| A2381 | B. fragilis |
| A2382 | B. fragilis |
| A2486 | B. fragilis |
| A2487 | B. fragilis |
| A2489 | B. fragilis |
| A2527 | B. fragilis |
| A2529 | B. fragilis |
| A2562 | B. fragilis |
| A2627 | B. fragilis |
| A2802 | B. fragilis |
| A2803 | B. fragilis |
| A2804 | B. fragilis |
| A2805 | B. fragilis |
| A2806 | B. fragilis |
| A2807 | B. fragilis |
| A2808 | B. fragilis |
| A2809 | B. fragilis |
| A2810 | B. fragilis |
| A2811 | B. fragilis |
| A2812 | B. fragilis |
| A2813 | B. fragilis |
| A2814 | B. fragilis |
| A2460 | B. thetaiotaomicron |
| A2462 | B. thetaiotaomicron |
| A2463 | B. thetaiotaomicron |
| A2464 | B. thetaiotaomicron |
| A2536 | B. thetaiotaomicron |
| A2591 | B. uniformis |
| A2604 | B. vulgatus |
| A2606 | B. vulgatus |
| A2613 | B. ovatus |
| A2616 | B. ovatus |
| A2815 | Bacteroides tectum |
| A2816 | B. ureolyticus |
| A2817 | Bacteroides capillosus |
| A2818 | B. ureolyticus |
| A2824 | Parabacter distasonis |
| A2825 | B. ovatus |
| A2826 | B. uniformis |
| A2827 | B. uniformis |
| A2828 | B. vulgatus |
| A2829 | B. vulgatus |
| A2830 | B. ovatus |
| A2831 | B. thetaiotaomicron |
| A2832 | Parabacter distasonis |
| A2833 | B. thetaiotaomicron |
| A2767 | C. difficile |
| A2768 | C. difficile |
| A2769 | C. difficile |
| A2770 | C. difficile |
| A2771 | C. difficile |
| A2772 | C. difficile |
| A2773 | C. difficile |
| A2774 | C. difficile |
| A2775 | C. difficile |
| A2776 | C. difficile |
| A2777 | C. difficile |
| A2778 | C. difficile |
| A2779 | C. difficile |
| A2780 | C. difficile |
| A2140 | C. perfringens |
| A2203 | C. perfringens |
| A2204 | C. perfringens |
| A2227 | C. perfringens |
| A2228 | C. perfringens |
| A2229 | C. perfringens |
| A2315 | C. perfringens |
| A2332 | C. perfringens |
| A2333 | C. perfringens |
| A2334 | C. perfringens |
| A2389 | C. perfringens |
| A2390 | C. perfringens |
| A864 | F. necrophorum |
| A871 | F. nucleatum |
| A1667 | F. necrophorum |
| A1666 | F. necrophorum |
| A2249 | F. nucleatum |
| A2716 | Fusobacterium species |
| A2717 | Fusobacterium species |
| A2719 | Fusobacterium species |
| A2721 | Fusobacterium species |
| A2722 | Fusobacterium species |
| A2710 | Fusobacterium species |
| A2711 | Fusobacterium species |
| A2712 | Fusobacterium species |
| A2713 | Fusobacterium species |

TABLE 8-continued

Panels of Anaerobic Organism Used to Generate MIC90 Data

| CMI# | ORGANISM |
|---|---|
| A2714 | Fusobacterium species |
| A2715 | Fusobacterium species |
| A1594 | Peptostreptococcus anaerobius |
| A2158 | Peptostreptococcus magnus |
| A2168 | Peptostreptococcus anaerobius |
| A2170 | Peptostreptococcus magnus |
| A2171 | Peptostreptococcus magnus |
| A2575 | Peptostreptococcus spp. |
| A2579 | Peptostreptococcus asaccharolyticus |
| A2580 | Peptostreptococcus asaccharolyticus |
| A2614 | Peptostreptococcus asaccharolyticus |
| A2620 | Peptostreptococcus asaccharolyticus |
| A2629 | Peptostreptococcus spp. |
| A2739 | Prevotella denticola |
| A2752 | Prevotella bivia |
| A2753 | Prevotella intermedia |
| A2754 | Prevotella intermedia |
| A2756 | Prevotella bivia |
| A2759 | Prevotella bivia |
| A2760 | Prevotella denticola |
| A2761 | Prevotella intermedia |
| A2762 | Prevotella melaninogenica |
| A2765 | Prevotella melaninogenica |
| A2766 | Prevotella melaninogenica |
| A2821 | Prevotella bivia |
| A2822 | Prevotella bivia |
| QCBF | B. fragilis |
| QCBT | B. thetaiotaomicron |
| QCCD | C. difficile |
| QCBF | B. fragilis |
| QCBT | B. thetaiotaomicron |
| QCCD | C. difficile |

In Table 9 below, the term "JMI" stands for The Jones Microbiology Institute located in North Liberty, Iowa.

TABLE 9

Panels of Gram Positive and Gram Negative Organism Used to Generate MIC90 Data

| JMI Isolate # | JMI Organism Code | Organism |
|---|---|---|
| 394 | ACB | Acinetobacter baumannii |
| 2166 | ACB | Acinetobacter baumannii |
| 3060 | ACB | Acinetobacter baumannii |
| 3170 | ACB | Acinetobacter baumannii |
| 9328 | ACB | Acinetobacter baumannii |
| 9922 | ACB | Acinetobacter baumannii |
| 13618 | ACB | Acinetobacter baumannii |
| 14308 | ACB | Acinetobacter baumannii |
| 17086 | ACB | Acinetobacter baumannii |
| 17176 | ACB | Acinetobacter baumannii |
| 30554 | ACB | Acinetobacter baumannii |
| 32007 | ACB | Acinetobacter baumannii |
| 1192 | ECL | Enterobacter cloacae |
| 3096 | ECL | Enterobacter cloacae |
| 5534 | ECL | Enterobacter cloacae |
| 6487 | ECL | Enterobacter cloacae |
| 9592 | ECL | Enterobacter cloacae |
| 11680 | ECL | Enterobacter cloacae |
| 12573 | ECL | Enterobacter cloacae |
| 12735 | ECL | Enterobacter cloacae |
| 13057 | ECL | Enterobacter cloacae |
| 18048 | ECL | Enterobacter cloacae |
| 25173 | ECL | Enterobacter cloacae |
| 29443 | ECL | Enterobacter cloacae |
| 44 | EF | Enterococcus faecalis |
| 355 | EF | Enterococcus faecalis |
| 886 | EF | Enterococcus faecalis |
| 955 | EF | Enterococcus faecalis |
| 1000 | EF | Enterococcus faecalis |
| 1053 | EF | Enterococcus faecalis |
| 1142 | EF | Enterococcus faecalis |
| 1325 | EF | Enterococcus faecalis |
| 1446 | EF | Enterococcus faecalis |
| 2014 | EF | Enterococcus faecalis |
| 2103 | EF | Enterococcus faecalis |
| 2255 | EF | Enterococcus faecalis |
| 2978 | EF | Enterococcus faecalis |
| 2986 | EF | Enterococcus faecalis |
| 5027 | EF | Enterococcus faecalis |
| 5270 | EF | Enterococcus faecalis |
| 5874 | EF | Enterococcus faecalis |
| 7430 | EF | Enterococcus faecalis |
| 7904 | EF | Enterococcus faecalis |
| 8092 | EF | Enterococcus faecalis |
| 8691 | EF | Enterococcus faecalis |
| 9090 | EF | Enterococcus faecalis |
| 10795 | EF | Enterococcus faecalis |
| 14104 | EF | Enterococcus faecalis |
| 16481 | EF | Enterococcus faecalis |
| 18217 | EF | Enterococcus faecalis |
| 22442 | EF | Enterococcus faecalis |
| 25726 | EF | Enterococcus faecalis |
| 26143 | EF | Enterococcus faecalis |
| 28131 | EF | Enterococcus faecalis |
| 29765 | EF | Enterococcus faecalis |
| 30279 | EF | Enterococcus faecalis |
| 31234 | EF | Enterococcus faecalis |
| 31673 | EF | Enterococcus faecalis |
| 115 | EFM | Enterococcus faecium |
| 227 | EFM | Enterococcus faecium |
| 414 | EFM | Enterococcus faecium |
| 712 | EFM | Enterococcus faecium |
| 870 | EFM | Enterococcus faecium |
| 911 | EFM | Enterococcus faecium |
| 2356 | EFM | Enterococcus faecium |
| 2364 | EFM | Enterococcus faecium |
| 2762 | EFM | Enterococcus faecium |
| 3062 | EFM | Enterococcus faecium |
| 4464 | EFM | Enterococcus faecium |
| 4473 | EFM | Enterococcus faecium |
| 4653 | EFM | Enterococcus faecium |
| 4679 | EFM | Enterococcus faecium |
| 6803 | EFM | Enterococcus faecium |
| 6836 | EFM | Enterococcus faecium |
| 8280 | EFM | Enterococcus faecium |
| 8702 | EFM | Enterococcus faecium |
| 9855 | EFM | Enterococcus faecium |
| 10766 | EFM | Enterococcus faecium |
| 12799 | EFM | Enterococcus faecium |
| 13556 | EFM | Enterococcus faecium |
| 13783 | EFM | Enterococcus faecium |
| 14687 | EFM | Enterococcus faecium |
| 15268 | EFM | Enterococcus faecium |
| 15525 | EFM | Enterococcus faecium |
| 15538 | EFM | Enterococcus faecium |
| 18102 | EFM | Enterococcus faecium |
| 18306 | EFM | Enterococcus faecium |
| 19967 | EFM | Enterococcus faecium |
| 22428 | EFM | Enterococcus faecium |
| 23482 | EFM | Enterococcus faecium |
| 29658 | EFM | Enterococcus faecium |
| 597 | EC | Escherichia coli |
| 847 | EC | Escherichia coli |
| 1451 | EC | Escherichia coli |

TABLE 9-continued

Panels of Gram Positive and Gram Negative Organism Used to Generate MIC90 Data

| JMI Isolate # | JMI Organism Code | Organism |
|---|---|---|
| 8682 | EC | *Escherichia coli* |
| 11199 | EC | *Escherichia coli* |
| 12583 | EC | *Escherichia coli* |
| 12792 | EC | *Escherichia coli* |
| 13265 | EC | *Escherichia coli* |
| 14594 | EC | *Escherichia coli* |
| 22148 | EC | *Escherichia coli* |
| 29743 | EC | *Escherichia coli* |
| 30426 | EC | *Escherichia coli* |
| 470 | BSA | Group A *Streptococcus* |
| 2965 | BSA | Group A *Streptococcus* |
| 3112 | BSA | Group A *Streptococcus* |
| 3637 | BSA | Group A *Streptococcus* |
| 4393 | BSA | Group A *Streptococcus* |
| 4546 | BSA | Group A *Streptococcus* |
| 4615 | BSA | Group A *Streptococcus* |
| 5848 | BSA | Group A *Streptococcus* |
| 6194 | BSA | Group A *Streptococcus* |
| 8816 | BSA | Group A *Streptococcus* |
| 11814 | BSA | Group A *Streptococcus* |
| 16977 | BSA | Group A *Streptococcus* |
| 18083 | BSA | Group A *Streptococcus* |
| 18821 | BSA | Group A *Streptococcus* |
| 25178 | BSA | Group A *Streptococcus* |
| 30704 | BSA | Group A *Streptococcus* |
| 12 | BSB | Group B *Streptococcus* |
| 10366 | BSB | Group B *Streptococcus* |
| 10611 | BSB | Group B *Streptococcus* |
| 16786 | BSB | Group B *Streptococcus* |
| 18833 | BSB | Group B *Streptococcus* |
| 30225 | BSB | Group B *Streptococcus* |
| 10422 | BSC | Group C *Streptococcus* |
| 14209 | BSC | Group C *Streptococcus* |
| 29732 | BSC | Group C *Streptococcus* |
| 8544 | BSG | Group G *Streptococcus* |
| 18086 | BSG | Group G *Streptococcus* |
| 29815 | BSG | Group G *Streptococcus* |
| 147 | HI | *Haemophilus influenzae* |
| 180 | HI | *Haemophilus influenzae* |
| 934 | HI | *Haemophilus influenzae* |
| 970 | HI | *Haemophilus influenzae* |
| 1298 | HI | *Haemophilus influenzae* |
| 1819 | HI | *Haemophilus influenzae* |
| 1915 | HI | *Haemophilus influenzae* |
| 2000 | HI | *Haemophilus influenzae* |
| 2562 | HI | *Haemophilus influenzae* |
| 2821 | HI | *Haemophilus influenzae* |
| 3133 | HI | *Haemophilus influenzae* |
| 3140 | HI | *Haemophilus influenzae* |
| 3497 | HI | *Haemophilus influenzae* |
| 3508 | HI | *Haemophilus influenzae* |
| 3535 | HI | *Haemophilus influenzae* |
| 4082 | HI | *Haemophilus influenzae* |
| 4108 | HI | *Haemophilus influenzae* |
| 4422 | HI | *Haemophilus influenzae* |
| 4868 | HI | *Haemophilus influenzae* |
| 4872 | HI | *Haemophilus influenzae* |
| 5858 | HI | *Haemophilus influenzae* |
| 6258 | HI | *Haemophilus influenzae* |
| 6875 | HI | *Haemophilus influenzae* |
| 7063 | HI | *Haemophilus influenzae* |
| 7600 | HI | *Haemophilus influenzae* |
| 8465 | HI | *Haemophilus influenzae* |
| 10280 | HI | *Haemophilus influenzae* |
| 10732 | HI | *Haemophilus influenzae* |
| 10850 | HI | *Haemophilus influenzae* |
| 11366 | HI | *Haemophilus influenzae* |
| 11716 | HI | *Haemophilus influenzae* |
| 11724 | HI | *Haemophilus influenzae* |
| 11908 | HI | *Haemophilus influenzae* |
| 12093 | HI | *Haemophilus influenzae* |
| 12107 | HI | *Haemophilus influenzae* |
| 13424 | HI | *Haemophilus influenzae* |
| 13439 | HI | *Haemophilus influenzae* |
| 13672 | HI | *Haemophilus influenzae* |
| 13687 | HI | *Haemophilus influenzae* |
| 13792 | HI | *Haemophilus influenzae* |
| 13793 | HI | *Haemophilus influenzae* |
| 14440 | HI | *Haemophilus influenzae* |
| 15351 | HI | *Haemophilus influenzae* |
| 15356 | HI | *Haemophilus influenzae* |
| 15678 | HI | *Haemophilus influenzae* |
| 15800 | HI | *Haemophilus influenzae* |
| 17841 | HI | *Haemophilus influenzae* |
| 18614 | HI | *Haemophilus influenzae* |
| 25195 | HI | *Haemophilus influenzae* |
| 27021 | HI | *Haemophilus influenzae* |
| 28326 | HI | *Haemophilus influenzae* |
| 28332 | HI | *Haemophilus influenzae* |
| 29918 | HI | *Haemophilus influenzae* |
| 29923 | HI | *Haemophilus influenzae* |
| 31911 | HI | *Haemophilus influenzae* |
| 428 | KPN | *Klebsiella pneumoniae* |
| 791 | KPN | *Klebsiella pneumoniae* |
| 836 | KPN | *Klebsiella pneumoniae* |
| 1422 | KPN | *Klebsiella pneumoniae* |
| 1674 | KPN | *Klebsiella pneumoniae* |
| 1883 | KPN | *Klebsiella pneumoniae* |
| 6486 | KPN | *Klebsiella pneumoniae* |
| 8789 | KPN | *Klebsiella pneumoniae* |
| 10705 | KPN | *Klebsiella pneumoniae* |
| 11123 | KPN | *Klebsiella pneumoniae* |
| 28148 | KPN | *Klebsiella pneumoniae* |
| 29432 | KPN | *Klebsiella pneumoniae* |
| 937 | MCAT | *Moraxella catarrhalis* |
| 1290 | MCAT | *Moraxella catarrhalis* |
| 1830 | MCAT | *Moraxella catarrhalis* |
| 1903 | MCAT | *Moraxella catarrhalis* |
| 4346 | MCAT | *Moraxella catarrhalis* |
| 4880 | MCAT | *Moraxella catarrhalis* |
| 6241 | MCAT | *Moraxella catarrhalis* |
| 6551 | MCAT | *Moraxella catarrhalis* |
| 7074 | MCAT | *Moraxella catarrhalis* |
| 7259 | MCAT | *Moraxella catarrhalis* |
| 7544 | MCAT | *Moraxella catarrhalis* |
| 8142 | MCAT | *Moraxella catarrhalis* |
| 8451 | MCAT | *Moraxella catarrhalis* |
| 9246 | MCAT | *Moraxella catarrhalis* |
| 9996 | MCAT | *Moraxella catarrhalis* |
| 12158 | MCAT | *Moraxella catarrhalis* |
| 13443 | MCAT | *Moraxella catarrhalis* |
| 13692 | MCAT | *Moraxella catarrhalis* |
| 13817 | MCAT | *Moraxella catarrhalis* |
| 14431 | MCAT | *Moraxella catarrhalis* |
| 14762 | MCAT | *Moraxella catarrhalis* |
| 14842 | MCAT | *Moraxella catarrhalis* |
| 15361 | MCAT | *Moraxella catarrhalis* |
| 15741 | MCAT | *Moraxella catarrhalis* |
| 17843 | MCAT | *Moraxella catarrhalis* |
| 18639 | MCAT | *Moraxella catarrhalis* |
| 241 | GC | *Neisseria gonorrhoeae* |
| 291 | GC | *Neisseria gonorrhoeae* |
| 293 | GC | *Neisseria gonorrhoeae* |
| 344 | GC | *Neisseria gonorrhoeae* |
| 451 | GC | *Neisseria gonorrhoeae* |
| 474 | GC | *Neisseria gonorrhoeae* |
| 491 | GC | *Neisseria gonorrhoeae* |
| 493 | GC | *Neisseria gonorrhoeae* |
| 503 | GC | *Neisseria gonorrhoeae* |
| 521 | GC | *Neisseria gonorrhoeae* |
| 552 | GC | *Neisseria gonorrhoeae* |
| 573 | GC | *Neisseria gonorrhoeae* |
| 592 | GC | *Neisseria gonorrhoeae* |

TABLE 9-continued

Panels of Gram Positive and Gram Negative Organism Used to Generate MIC90 Data

| JMI Isolate # | JMI Organism Code | Organism |
|---|---|---|
| 25 | NM | *Neisseria meningitidis* |
| 813 | NM | *Neisseria meningitidis* |
| 1725 | NM | *Neisseria meningitidis* |
| 2747 | NM | *Neisseria meningitidis* |
| 3201 | NM | *Neisseria meningitidis* |
| 3335 | NM | *Neisseria meningitidis* |
| 7053 | NM | *Neisseria meningitidis* |
| 9407 | NM | *Neisseria meningitidis* |
| 10447 | NM | *Neisseria meningitidis* |
| 12685 | NM | *Neisseria meningitidis* |
| 12841 | NM | *Neisseria meningitidis* |
| 14038 | NM | *Neisseria meningitidis* |
| 1127 | PM | *Proteus mirabilis* |
| 3049 | PM | *Proteus mirabilis* |
| 4471 | PM | *Proteus mirabilis* |
| 8793 | PM | *Proteus mirabilis* |
| 10702 | PM | *Proteus mirabilis* |
| 11218 | PM | *Proteus mirabilis* |
| 14662 | PM | *Proteus mirabilis* |
| 17072 | PM | *Proteus mirabilis* |
| 19059 | PM | *Proteus mirabilis* |
| 23367 | PM | *Proteus mirabilis* |
| 29819 | PM | *Proteus mirabilis* |
| 31419 | PM | *Proteus mirabilis* |
| 1881 | PSA | *Pseudomonas aeruginosa* |
| 5061 | PSA | *Pseudomonas aeruginosa* |
| 7909 | PSA | *Pseudomonas aeruginosa* |
| 8713 | PSA | *Pseudomonas aeruginosa* |
| 14318 | PSA | *Pseudomonas aeruginosa* |
| 14772 | PSA | *Pseudomonas aeruginosa* |
| 15512 | PSA | *Pseudomonas aeruginosa* |
| 17093 | PSA | *Pseudomonas aeruginosa* |
| 17802 | PSA | *Pseudomonas aeruginosa* |
| 19661 | PSA | *Pseudomonas aeruginosa* |
| 29967 | PSA | *Pseudomonas aeruginosa* |
| 31539 | PSA | *Pseudomonas aeruginosa* |
| 82 | SA | *Staphylococcus aureus* |
| 99 | SA | *Staphylococcus aureus* |
| 138 | SA | *Staphylococcus aureus* |
| 139 | SA | *Staphylococcus aureus* |
| 140 | SA | *Staphylococcus aureus* |
| 141 | SA | *Staphylococcus aureus* |
| 142 | SA | *Staphylococcus aureus* |
| 272 | SA | *Staphylococcus aureus* |
| 287 | SA | *Staphylococcus aureus* |
| 354 | SA | *Staphylococcus aureus* |
| 382 | SA | *Staphylococcus aureus* |
| 1112 | SA | *Staphylococcus aureus* |
| 1687 | SA | *Staphylococcus aureus* |
| 1848 | SA | *Staphylococcus aureus* |
| 2031 | SA | *Staphylococcus aureus* |
| 2159 | SA | *Staphylococcus aureus* |
| 2645 | SA | *Staphylococcus aureus* |
| 3256 | SA | *Staphylococcus aureus* |
| 3276 | SA | *Staphylococcus aureus* |
| 4044 | SA | *Staphylococcus aureus* |
| 4214 | SA | *Staphylococcus aureus* |
| 4217 | SA | *Staphylococcus aureus* |
| 4220 | SA | *Staphylococcus aureus* |
| 4231 | SA | *Staphylococcus aureus* |
| 4240 | SA | *Staphylococcus aureus* |
| 4262 | SA | *Staphylococcus aureus* |
| 4370 | SA | *Staphylococcus aureus* |
| 4665 | SA | *Staphylococcus aureus* |
| 4666 | SA | *Staphylococcus aureus* |
| 4667 | SA | *Staphylococcus aureus* |
| 5026 | SA | *Staphylococcus aureus* |
| 5666 | SA | *Staphylococcus aureus* |
| 6792 | SA | *Staphylococcus aureus* |
| 7023 | SA | *Staphylococcus aureus* |
| 7461 | SA | *Staphylococcus aureus* |
| 7899 | SA | *Staphylococcus aureus* |
| 7901 | SA | *Staphylococcus aureus* |
| 8714 | SA | *Staphylococcus aureus* |
| 9374 | SA | *Staphylococcus aureus* |
| 9437 | SA | *Staphylococcus aureus* |
| 10056 | SA | *Staphylococcus aureus* |
| 10110 | SA | *Staphylococcus aureus* |
| 11379 | SA | *Staphylococcus aureus* |
| 11629 | SA | *Staphylococcus aureus* |
| 11659 | SA | *Staphylococcus aureus* |
| 12788 | SA | *Staphylococcus aureus* |
| 12789 | SA | *Staphylococcus aureus* |
| 13043 | SA | *Staphylococcus aureus* |
| 13086 | SA | *Staphylococcus aureus* |
| 13721 | SA | *Staphylococcus aureus* |
| 13742 | SA | *Staphylococcus aureus* |
| 13932 | SA | *Staphylococcus aureus* |
| 14210 | SA | *Staphylococcus aureus* |
| 14384 | SA | *Staphylococcus aureus* |
| 15428 | SA | *Staphylococcus aureus* |
| 15430 | SA | *Staphylococcus aureus* |
| 17721 | SA | *Staphylococcus aureus* |
| 18688 | SA | *Staphylococcus aureus* |
| 19095 | SA | *Staphylococcus aureus* |
| 20195 | SA | *Staphylococcus aureus* |
| 22141 | SA | *Staphylococcus aureus* |
| 22689 | SA | *Staphylococcus aureus* |
| 27398 | SA | *Staphylococcus aureus* |
| 29048 | SA | *Staphylococcus aureus* |
| 29051 | SA | *Staphylococcus aureus* |
| 30491 | SA | *Staphylococcus aureus* |
| 30538 | SA | *Staphylococcus aureus* |
| 25 | SEPI | *Staphylococcus epidermidis* |
| 53 | SEPI | *Staphylococcus epidermidis* |
| 385 | SEPI | *Staphylococcus epidermidis* |
| 398 | SEPI | *Staphylococcus epidermidis* |
| 701 | SEPI | *Staphylococcus epidermidis* |
| 713 | SEPI | *Staphylococcus epidermidis* |
| 1381 | SEPI | *Staphylococcus epidermidis* |
| 2174 | SEPI | *Staphylococcus epidermidis* |
| 2286 | SEPI | *Staphylococcus epidermidis* |
| 2969 | SEPI | *Staphylococcus epidermidis* |
| 3417 | SEPI | *Staphylococcus epidermidis* |
| 3447 | SEPI | *Staphylococcus epidermidis* |
| 4753 | SEPI | *Staphylococcus epidermidis* |
| 7241 | SEPI | *Staphylococcus epidermidis* |
| 9366 | SEPI | *Staphylococcus epidermidis* |
| 10665 | SEPI | *Staphylococcus epidermidis* |
| 11792 | SEPI | *Staphylococcus epidermidis* |
| 12311 | SEPI | *Staphylococcus epidermidis* |
| 13036 | SEPI | *Staphylococcus epidermidis* |
| 13227 | SEPI | *Staphylococcus epidermidis* |
| 13243 | SEPI | *Staphylococcus epidermidis* |
| 13621 | SEPI | *Staphylococcus epidermidis* |
| 13638 | SEPI | *Staphylococcus epidermidis* |
| 13800 | SEPI | *Staphylococcus epidermidis* |
| 14078 | SEPI | *Staphylococcus epidermidis* |
| 14392 | SEPI | *Staphylococcus epidermidis* |
| 15007 | SEPI | *Staphylococcus epidermidis* |
| 16733 | SEPI | *Staphylococcus epidermidis* |
| 18871 | SEPI | *Staphylococcus epidermidis* |
| 23285 | SEPI | *Staphylococcus epidermidis* |
| 27805 | SEPI | *Staphylococcus epidermidis* |
| 29679 | SEPI | *Staphylococcus epidermidis* |
| 29985 | SEPI | *Staphylococcus epidermidis* |
| 30259 | SEPI | *Staphylococcus epidermidis* |
| 31444 | SEPI | *Staphylococcus epidermidis* |
| 268 | SPN | *Streptococcus pneumoniae* |
| 1264 | SPN | *Streptococcus pneumoniae* |

TABLE 9-continued

Panels of Gram Positive and Gram Negative Organism Used to Generate MIC90 Data

| JMI Isolate # | JMI Organism Code | Organism |
|---|---|---|
| 2482 | SPN | Streptococcus pneumoniae |
| 2653 | SPN | Streptococcus pneumoniae |
| 2994 | SPN | Streptococcus pneumoniae |
| 3123 | SPN | Streptococcus pneumoniae |
| 3124 | SPN | Streptococcus pneumoniae |
| 4336 | SPN | Streptococcus pneumoniae |
| 4858 | SPN | Streptococcus pneumoniae |
| 5606 | SPN | Streptococcus pneumoniae |
| 5881 | SPN | Streptococcus pneumoniae |
| 5897 | SPN | Streptococcus pneumoniae |
| 5900 | SPN | Streptococcus pneumoniae |
| 6051 | SPN | Streptococcus pneumoniae |
| 6216 | SPN | Streptococcus pneumoniae |
| 6556 | SPN | Streptococcus pneumoniae |
| 7270 | SPN | Streptococcus pneumoniae |
| 7584 | SPN | Streptococcus pneumoniae |
| 8479 | SPN | Streptococcus pneumoniae |
| 8501 | SPN | Streptococcus pneumoniae |
| 9256 | SPN | Streptococcus pneumoniae |
| 9257 | SPN | Streptococcus pneumoniae |
| 10246 | SPN | Streptococcus pneumoniae |
| 10467 | SPN | Streptococcus pneumoniae |
| 10886 | SPN | Streptococcus pneumoniae |
| 11217 | SPN | Streptococcus pneumoniae |
| 11228 | SPN | Streptococcus pneumoniae |
| 11238 | SPN | Streptococcus pneumoniae |
| 11757 | SPN | Streptococcus pneumoniae |
| 11768 | SPN | Streptococcus pneumoniae |
| 12121 | SPN | Streptococcus pneumoniae |
| 12124 | SPN | Streptococcus pneumoniae |
| 12149 | SPN | Streptococcus pneumoniae |
| 12767 | SPN | Streptococcus pneumoniae |
| 12988 | SPN | Streptococcus pneumoniae |
| 13321 | SPN | Streptococcus pneumoniae |
| 13393 | SPN | Streptococcus pneumoniae |
| 13521 | SPN | Streptococcus pneumoniae |
| 13544 | SPN | Streptococcus pneumoniae |
| 13700 | SPN | Streptococcus pneumoniae |
| 13704 | SPN | Streptococcus pneumoniae |
| 13822 | SPN | Streptococcus pneumoniae |
| 13838 | SPN | Streptococcus pneumoniae |
| 14131 | SPN | Streptococcus pneumoniae |
| 14413 | SPN | Streptococcus pneumoniae |
| 14744 | SPN | Streptococcus pneumoniae |
| 14808 | SPN | Streptococcus pneumoniae |
| 14827 | SPN | Streptococcus pneumoniae |
| 14835 | SPN | Streptococcus pneumoniae |
| 14836 | SPN | Streptococcus pneumoniae |
| 15832 | SPN | Streptococcus pneumoniae |
| 17336 | SPN | Streptococcus pneumoniae |
| 17343 | SPN | Streptococcus pneumoniae |
| 17349 | SPN | Streptococcus pneumoniae |
| 17735 | SPN | Streptococcus pneumoniae |
| 18060 | SPN | Streptococcus pneumoniae |
| 18567 | SPN | Streptococcus pneumoniae |
| 18595 | SPN | Streptococcus pneumoniae |
| 19082 | SPN | Streptococcus pneumoniae |
| 19826 | SPN | Streptococcus pneumoniae |
| 22174 | SPN | Streptococcus pneumoniae |
| 22175 | SPN | Streptococcus pneumoniae |
| 27003 | SPN | Streptococcus pneumoniae |
| 28310 | SPN | Streptococcus pneumoniae |
| 28312 | SPN | Streptococcus pneumoniae |
| 29890 | SPN | Streptococcus pneumoniae |
| 29910 | SPN | Streptococcus pneumoniae |

What is claimed is:

1. A solid Form I of the compound of formula (I):

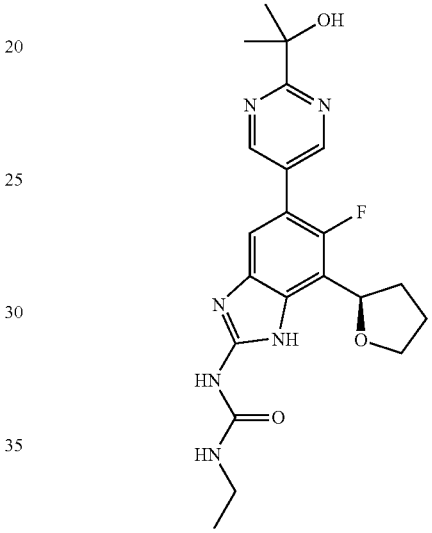

2. The solid Form I of claim 1, which is characterized by an X-ray powder diffraction pattern (XPRD) comprising at least three approximate peak positions (degrees 2 θ±0.2) when measured using Cu Kα radiation, selected from the group consisting of 9.3, 11.7, 12.1, 12.4, 14.5, 15.9, 16.3, 16.6, 18.5, 19.4, 21.5, 22.3, 22.8, 23.8, 24.5, 25.7, 28.1, 28.4, 30.3, and 33.4, when the XPRD is collected from about 5 to about 38 degrees 2 θ.

3. The solid Form I of claim 1, which is characterized by an X-ray powder diffraction pattern (XPRD) comprising at least three approximate peak positions (degrees 2 θ±0.2) when measured using Cu Kα radiation, selected from the group consisting of 9.3, 16.6, 18.5, 19.4, 21.5, and 25.7, when the XPRD is collected from about 5 to about 38 degrees 2 θ.

4. The solid Form I of claim 3, characterized by an X-ray powder diffraction pattern, as measured using Cu Kα radiation, substantially similar to FIG. 1.

5. The solid Form I of claim 4, further characterized by an endothermic peak having an onset temperature at about 318° C. as measured by differential scanning calorimetry in which the temperature is scanned at about 10° C. per minute.

6. A method for preparing crystal Form I of the compound of formula (I) according to claim 1 comprising suspending a solid material of the free base in a solvent system comprising an alcohol and an ether and isolating the solid.

7. A hydrochloric acid salt of the compound of formula (I):

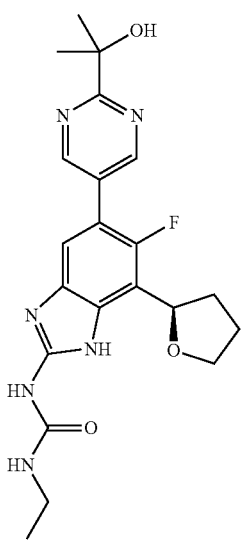

(I)

8. The hydrochloric acid salt of claim 7, wherein said salt is Form II solid form.

9. The hydrochloric acid salt of claim 8, wherein said Form II solid form is characterized by an X-ray powder diffraction pattern (XPRD) comprising at least three approximate peak positions (degrees 2 θ±0.2) when measured using Cu Kα radiation, selected from the group consisting of 6.7, 9.2, 16.7, 18.6, 19.5, 20.5, 25.6, and 27.5, when the XPRD is collected from about 5 to about 38 degrees 2 θ.

10. The hydrochloric acid salt of claim 8, wherein said Form II solid form is characterized by an X-ray powder diffraction pattern, as measured using Cu Kα radiation, substantially similar to FIG. 4.

11. The hydrochloric acid salt of claim 9, wherein said Form II solid form is further characterized by an endothermic peak having an onset temperature at about 252° C. as measured by differential scanning calorimetry in which the temperature is scanned at about 10° C. per minute.

12. A method for preparing solid Form II of the hydrochloride salt of the compound of formula (I) according to claim 8 comprising suspending a free base of the 6-fluorobenzimidazolyl urea compound in an acidic solvent mixture comprising one or more ethereal solvents and water.

13. An amorphous Form III of the 6-fluorobenzimidazolyl urea compound of formula I:

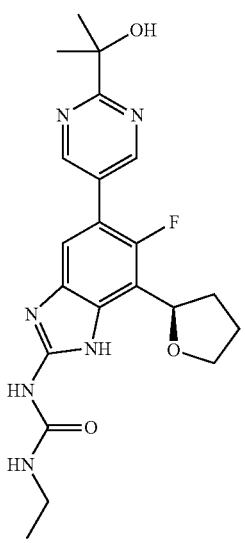

(I)

14. The amorphous Form III of the fluorobenzimidazolyl urea compound according to claim 13, which is characterized by an X-ray powder diffraction pattern (XPRD) using Cu Kα radiation, characterized by a broad halo with no discernable diffraction peak.

15. A method for preparing amorphous Form III of the 6-fluorobenzimidazolyl urea compound according to claim 13 comprising lyophilizing, spray drying, drum drying, or pulse conversion drying a solution of the 6-fluorobenzimidazolyl urea compound.

16. An amorphous Form IV of the mesylate salt of the 6-fluorobenzimidazolyl urea compound of formula I:

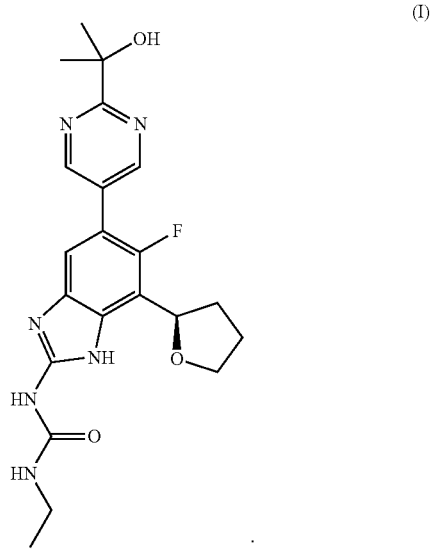 [SMILES: CCNC(=O)Nc1nc2cc(-c3cnc(C(C)(C)O)nc3)c(F)c([C@H]3CCCO3)c2[nH]1]

(I)

17. The amorphous Form IV of the mesylate salt of the 6-fluorobenzimidazolyl urea compound according to claim 16, which is characterized by an X-ray powder diffraction pattern (XPRD) using Cu Kα radiation, characterized by a broad halo with no discernable diffraction peak.

18. The hydrochloric acid salt of claim 8, wherein said Form II solid form is stable for at least one month at 40° C. with relative humidity of up to 75%.

19. The solid Form I of claim 2, wherein said solid is stable for at least one month at 40° C. with relative humidity of up to 75%.

20. A pharmaceutical composition comprising the compound according to claim 1 and a pharmaceutically acceptable carrier, adjuvant, or vehicle.

21. A method for treating a bacterial infection in a patient, wherein the bacterial infection is characterized by the presence of one or more of *Mycobacterium tuberculosis, Streptococcus pneumoniae, Staphylococcus epidermidis, Enterococcus faecalis, Staphylococcus aureus, Clostridium difficile, Moraxella catarrhalis, Neisseria gonorrhoeae, Neisseria meningitidis, Mycobacterium avium* complex, *Mycobacterium abscessus, Mycobacterium kansasii, Mycobacterium ulcerans, Chlamydophila pneumoniae, Chlamydia trachomatis, Haemophilus influenzae, Streptococcus pyogenes* or β-haemolytic streptococci, comprising administering to said patient a pharmaceutical composition according to claim 20.

22. The method according to claim 21, wherein the bacterial infection is selected from one or more of the following: upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections, uncomplicated skin and skin structure infections (uSSSI), complicated skin and skin structure infections (cSSSI), catheter infections, pharyngitis, sinusitis, otitis externa, otitis media, bronchitis, empyema, pneumonia, community-acquired bacterial *pneumoniae* (CABP), hospital-acquired pneumonia (HAP), hospital-acquired bacterial pneumonia, ventilator-associated pneumonia (VAP), diabetic foot infections, vancomycin resistant *enterococci* infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

23. The method according to claim 22, wherein the bacterial infection is selected from one or more of the following: community-acquired bacterial *pneumoniae* (CABP), hospital-acquired pneumonia (HAP), hospital-acquired bacterial pneumonia, ventilator-associated pneumonia (VAP), bacteremia, diabetic foot infections, catheter infections, uncomplicated skin and skin structure infections (uSSSI), complicated skin and skin structure infections (cSSSI), vancomycin resistant enterococci infections or osteomyelitis.

* * * * *